US008629256B2

(12) United States Patent
Looger et al.

(10) Patent No.: US 8,629,256 B2
(45) Date of Patent: Jan. 14, 2014

(54) GENETICALLY ENCODED CALCIUM INDICATOR POLYPEPTIDES AND NUCLEIC ACIDS ENCODING SAME

(75) Inventors: Loren Lee Looger, Madison, AL (US); Lin Tian, Reston, VA (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 134 days.

(21) Appl. No.: 13/192,314

(22) Filed: Jul. 27, 2011

(65) Prior Publication Data
US 2012/0034691 A1    Feb. 9, 2012

Related U.S. Application Data

(63) Continuation of application No. PCT/US2010/055451, filed on Nov. 4, 2010.

(60) Provisional application No. 61/258,738, filed on Nov. 6, 2009.

(51) Int. Cl.
| | | |
|---|---|---|
| *C07H 21/04* | (2006.01) | |
| *C12N 1/20* | (2006.01) | |
| *C12N 15/00* | (2006.01) | |
| *C12N 5/00* | (2006.01) | |
| *C12N 5/02* | (2006.01) | |
| *C12N 15/74* | (2006.01) | |
| *C07K 1/00* | (2006.01) | |
| *C07K 14/00* | (2006.01) | |
| *C07K 17/00* | (2006.01) | |

(52) U.S. Cl.
USPC ............... 536/23.5; 435/252.3; 435/320.1; 435/325; 435/471; 530/350

(58) Field of Classification Search
None
See application file for complete search history.

(56) References Cited

U.S. PATENT DOCUMENTS

| | | | |
|---|---|---|---|
| 6,133,502 A | 10/2000 | Kasuga et al. | |
| 6,175,057 B1 | 1/2001 | Mucke et al. | |
| 6,180,849 B1 | 1/2001 | Streuli et al. | |

FOREIGN PATENT DOCUMENTS

| | | |
|---|---|---|
| WO | WO 2006/110728 | 10/2006 |
| WO | WO 2008/153543 | 12/2008 |

OTHER PUBLICATIONS

GenBank Accession No. ABD36085, Mar. 22, 2006, 2 pages.
Airan et al., "Temporally precise in vivo control of intracellular signaling," *Nature*, 2009, 458(7241): 1025-1029.
Andrade et al., "Adsorption of complex proteins at interfaces," *Pure and Appl. Chem.*, 1992, 64(11):1777-1781.
Baird et al., "Circular permutation and receptor insertion within green fluorescent proteins," *PNAS*, Sep. 1999, 96:11241-11246.
Berkner et al., "Abundant expression of polyomavirus middle T antigen and dihydrofolate reductase in an adenovirus recombinant," *J. Virology*, 1987, 61:1213-1220.
Brand et al., "Ectopic expression in *Drosophila*," *Methods Cell Biol.*, 1994, 44:635-654.
Brinstar et al., "Expression of a microinjected immunoglobulin gene in the spleen of transgenic mice," *Nature*, 1983, 306:332-336.
Chalasani et al., "Dissecting a circuit for olfactory behaviour in *Caenorhabditis elegans*," *Nature*, 2007, 450:63-70.
Choi et al., "Evolutionary conservation in multiple faces of protein interaction," *Proteins: Structure, Function, and Bioinformatics*, 2009, 77(1):14-25.
Costantini et al., "Introduction of a rabbit β-globin gene into the mouse germ line," *Nature*, 1981, 294:92-94.
Davidson et al., "Overproduction of polyomavirus middle T antigen in mammalian cells through the use of an adenovirus vector," *J. Virology*, 1987, 61:1226-1239.
Debacker et al., "Genomic cloning, heterologous expression and pharmacological characterization of a human histamine H1 receptor," *Biochem. Biophys. Res. Commun.*, 1993, 197(3): 1601-1608.
Diez-Garcia et al., "Activation of cerebella parallel fibers monitored in transgenic mice expressing a fluorescent Ca2+ indicator protein," *Eur J Neurosci.*, Aug. 2005, 22(3):627-635.
Garcea and Gissmann, "Virus-like particles as vaccines and vessels for the delivery of small molecules," *Current Opinion in Biotechnology*, 1994, 15:513-517.
Gondi and Rao, "Concepts in in vivo siRNA delivery for cancer therapy," *J. Cell Physiol.*, Aug. 2009, 220(2):285-291
Guo et al., "Protein tolerance to random amino acid change," *Proc. Natl. Acad. Sci. USA*, 2004, 101(25):9205-9210.
Haj-Ahmad et al., "Development of a helper-independent human adenovirus vector and its use in the transfer of the herpes simplex virus thymidine kinase gene," *J. Virology*, 1986, 57:267-274.
Hsu and Luo, "Molecular dissection of G protein preference using Gs{alpha} chimeras reveals novel ligand signaling of GPCRs," *Am J Physiol Endocrinol Metab.*, 2007, 293(4):E1021-E1029.
Huber et al., "Sparse optical microstimulation in barrel cortex drives learned behaviour in freely moving mice," *Nature*, 2008, 451:61-64.
Lacy et al., "A foreign beta-globin gene in transgenic mice: integration at abnormal chromosomal positions and expression in inappropriate tissues," *Cell*, 1983, 34(2):343-358.
Mao et al., "Characterization and Subcellular Targeting of GCaMPType Genetically-Encoded Calcium Indicators," *PLoS One*, 2008, 3:e1796.
Massie et al., "Construction of a helper-free recombinant adenovirus that expresses polyomavirus large T antigen," *Mol. Cell. Biol.*, 1986, 6(8):2872-2883.
McKnight et al., "Expression of the Chicken Transferrin. Gene in Transgenic Mice," *Cell*, 1983, 34:335-341.
Oh and Park, "siRNA delivery systems for cancer treatment," *Adv. Drug. Deliv. Rev.*, 2009, 61(10):850-862.
Palmiter et al., "Differential regulation of metallothionein-thymidine kinase fusion genes in transgenic mice and their offspring," *Cell*, 1982, 29:701-710.
Palmiter et al., "Dramatic growth of mice that develop from eggs microinjected with metallothionein-growth hormone fusion genes," *Nature*, 1982, 300:611-615.

(Continued)

*Primary Examiner* — Robert Landsman
(74) *Attorney, Agent, or Firm* — Fish & Richardson P.C.

(57) ABSTRACT

Provided herein are nucleic acid sequences and polypeptides encoding a genetically encoded calcium indicator (GECI). Also provided are vectors and cells comprising the nucleic acid sequences and/or polypeptides. Kits comprising the nucleic acid sequences, polypeptides, vectors, cells and combinations thereof are also provided. Also provided herein are methods of screening for G-protein coupled receptor (GPCR) agonists and antagonists and methods of monitoring neural activity using the GECIs.

18 Claims, 43 Drawing Sheets

(56) References Cited

OTHER PUBLICATIONS

Palmiter et al., "Metallothionein-human GH fusion genes stimulate growth of mice," *Science*, 1983, 222:809-814.

Park et al., "Prediction of protein-protein interaction types using association rule based classification," *BMC Bioinformatics*, 2009, 10:1471-2105.

Pepperl-Klindworth et al., "Protein delivery by subviral particles of human cytomegalovirus," *Gene Therapy*, 2003, 10:278-284.

Petreanu et al., "Channelrhodopsin-2-assisted circuit mapping of long-range callosal projections," *Nat. Neurosci.*, 2007, 10:663-668.

Pologruto et al., "Monitoring neural activity and [Ca2+] with genetically encoded Ca2+ indicators," *The Journal of Neuroscience*, Jul. 21, 2004, 24(29):6507-6514.

Saito and Nakatsuji, "Efficient gene transfer into the embryonic mouse brain using in vivo electroporation," *Dev. Biol.*, 2001, 240:237-246.

Stewart et al., "Human beta-globin gene sequences injected into mouse eggs, retained in adults, and transmitted to progeny," *Science*, 1982, 217:1046-1048.

Stoppini et al., "A simple method for organotypic cultures of nervous tissue," *J. Neurosci. Methods*, 1991, 37:173-182.

Tallini et al., "Imaging cellular signals in the heart in vivo: cardiac expression of the high-signal Ca2+ indicator GCaMP2," Mar. 21, 2006, *PNAS*, 103(12):4753-4758.

Wagner et al., "The human beta-globin gene and a functional viral thymidine kinase gene in developing mice," *Proc. Nat. Acad. Sci. USA*, 1981, 78:5016-5020.

Whitehead et al., "Knocking down barriers: advances in siRNA delivery," *Nat. Rev. Drug. Discov.*, 2009, 8(2):129-38.

Zhang et al., "Evaluation of FLIPR calcium assay kit-a new no-wash fluorescence calcium indicator reagent," *J Biomol Screen*, 2003, 8(5):571-577.

Zhang et al., "Generation and identification of recombinant adenovirus by liposome-mediated transfection and PCR analysis," *BioTechniques*, 1993, 15:868-872.

Zuker, "On finding all suboptimal foldings of an RNA molecule," *Science*, 1989, 244:48-52.

Authorized Officer Kim Seung Beom, PCT/US2010/055451, International Search Report, mailed Jul. 18, 2011, 3 pages.

Authorized Officer Kim Seung Beom, PCT/US2010/055451, Written Opinion of The International Searching Authority, completed Jul. 18, 2011, 5 pages.

Authorized Officer Yukari Nakamura, PCT/US2010/055451, Preliminary Report on Patentability, issued May 8, 2012, 6 pages.

Extended European Search Report in EP Application No. 10829090.9, dated Aug. 6, 2013, 7 pages.

Akerboom et al., "Crystal structures of the GCaMP calcium sensor reveal the mechanism of fluorescence signal change and aid rational design," *J Biol. Chem.*, Mar. 6, 2009, 284(10):6455-6464.

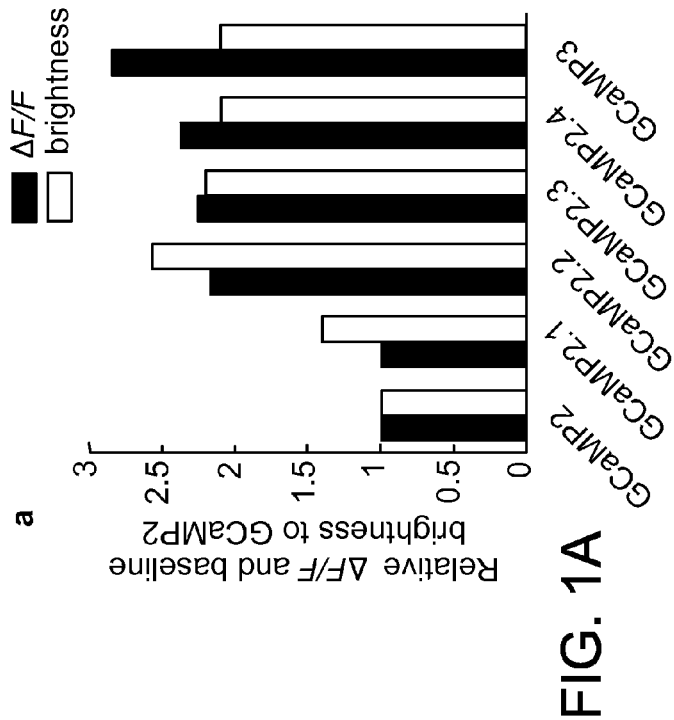
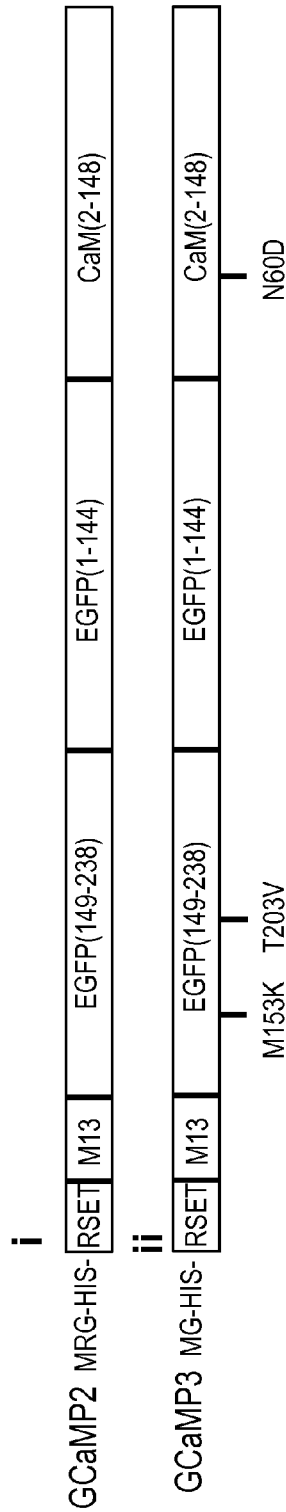
FIG. 1A
FIG. 1B

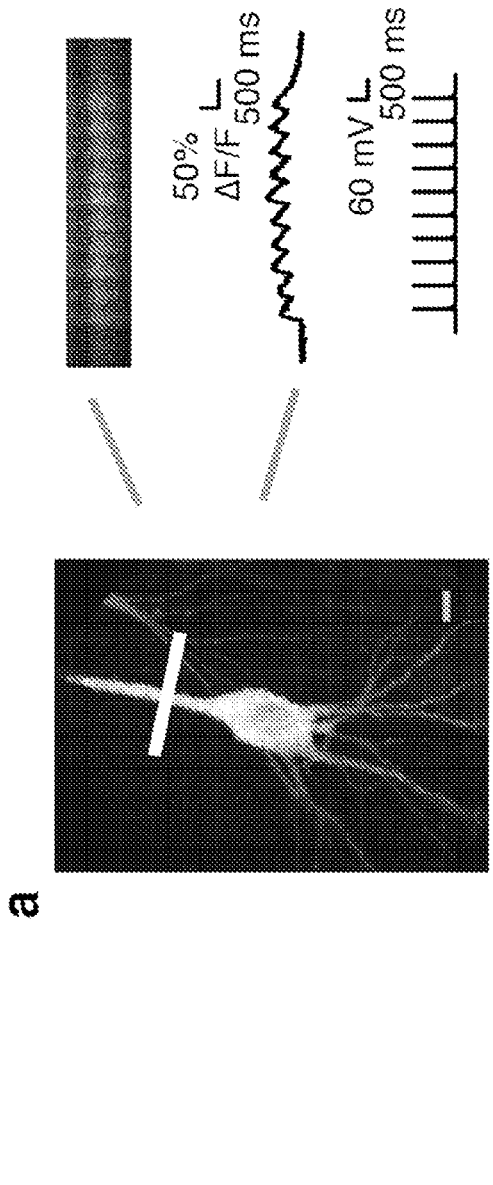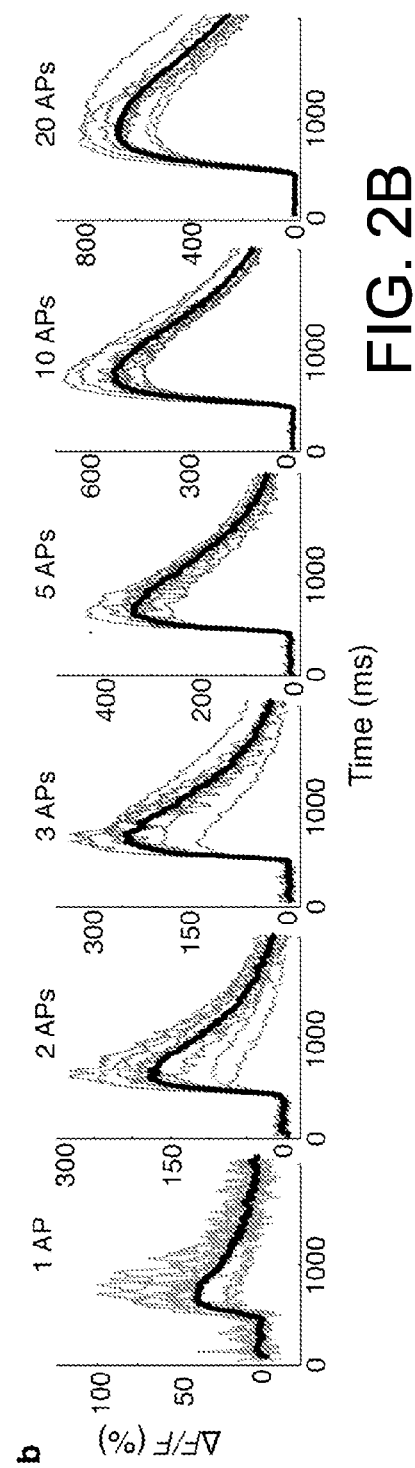
FIG. 2A
FIG. 2B

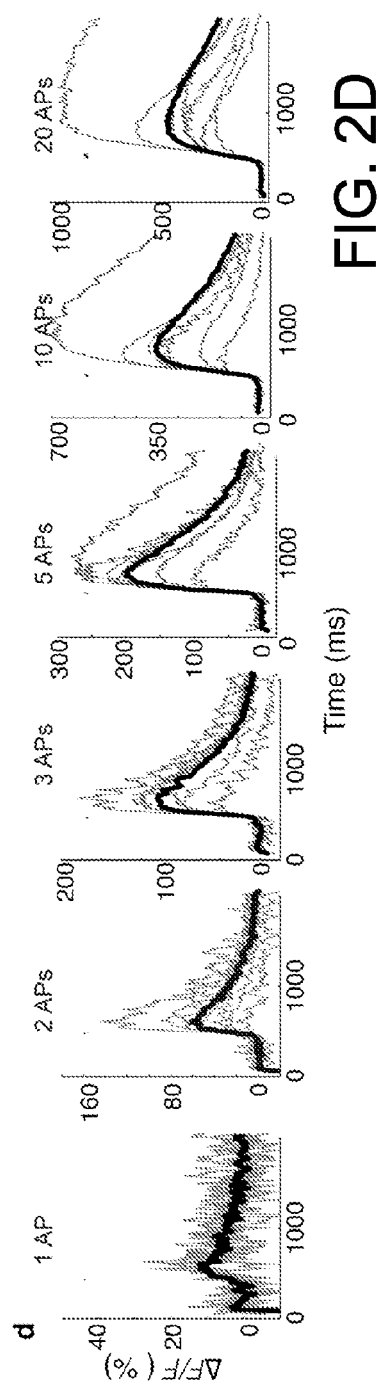
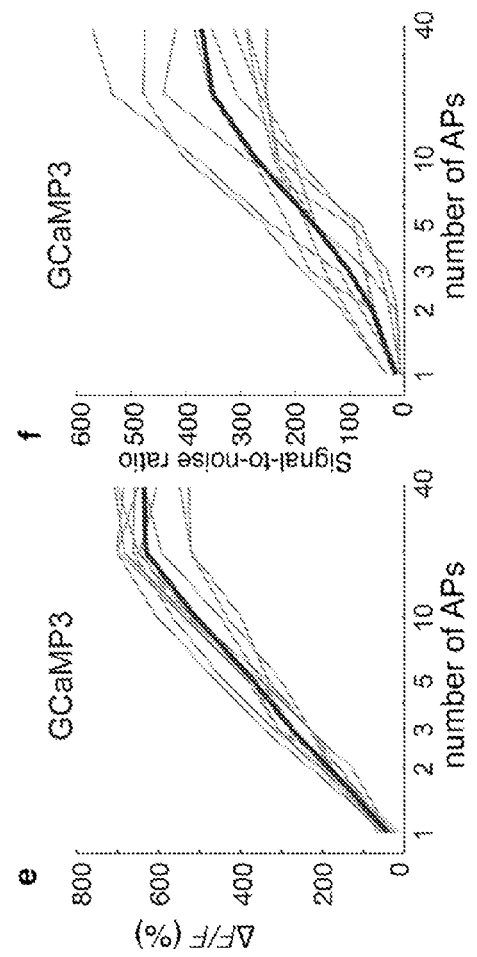
FIG. 2D
FIG. 2E
FIG. 2F

|  | Assay window (response/baseline) | EC50 ±S.E. (nM) | Z' factor |
|---|---|---|---|
| GCaMP3 | 5.523 | 9.27 ± 0.19 | 0.67 |
| BD calcium kit | 4.330 | 15.3 ± 0.11 | 0.82 |
| Calcium 5 | 3.552 | 21.03 ± 0.10 | 0.85 |

FIG. 8C

|  | Assay window (response/baseline) | EC50 ±S.E. (nM) | Z' factor |
| --- | --- | --- | --- |
| GCaMP3 | 4.639 | 18.27 ± 0.06 | 0.89 |
| BD calcium kit | 2.026 | 19.03 ± 0.17 | 0.88 |
| Calcium 5 | 2.23 | 10.29 ± 0.16 | 0.87 |

FIG. 9C

| | IC50 ±S.E. (mM) | |
|---|---|---|
| | Diphenhydramine | Cetirizine |
| GCaMP3 | 0.17 ± 0.15 | 26.34 ± 0.34 |
| Calcium 5 | 0.46 ± 0.14 | 19.65 ± 0.14 |
| BD calcium kit | 0.29 ± 0.24 | 28.74 ± 0.17 |

| | IC50 ±S.E. (mM) | |
|---|---|---|
| | Diphenhydramine | Cetirizine |
| GCaMP3 | 0.12 ± 0.05 | 18.82 ± 0.48 |
| Calcium 5 | 0.65 ± 0.16 | 10.13 ± 0.14 |
| BD calcium kit | 0.34 ± 0.14 | 19.91 ± 0.29 |

GCaMP2  MRGSHHHHHHGMASMTGGQQMGRDLYDDDDKDLATMVDSSRRKWNKTGHA    50

VRAIGRISSLENVYIMADKQKNGIKANFKIRHNIEDGGVQLAYHYQQNTP    100

IGDGPVLLPDNHYLSTQSKLSKDPNEKRDHMVLLEFVTAAGITLGMDELY    150

KGGTGGSMVSKGEELFTGVVPILVELDGDVNGHKFSVSGEGEGDATYGKL    200

TLKFICTTGKLPVPWPTLVTTLTYGVQCFSRYPDHMKQHDFFKSAMPEGY    250

IQERTIFFKDDGNYKTRAEVKFEGDTLVNRIELKGIDFKEDGNILGHKLE    300

YNTRDQLTEEQIAEFKEAFSLFDKDGDGTITTKELGTVMRSLGQNPTEAE    350

LQDMINEVDADGNGTIDFPEFLTMMARKMKDTDSEEEIREAFRVFDKDGN    400

GYISAAELRHVMTNLGEKLTDEEVDEMIREADIDGDGQVNYEEFVQMMTAK*    450

FIG. 13A

SEQUENCE LISTING

```
<160> NUMBER OF SEQ ID NOS: 15

<210> SEQ ID NO 1
<211> LENGTH: 1353
<212> TYPE: DNA
<213> ORGANISM: Artificial Sequence
<220> FEATURE:
<223> OTHER INFORMATION: Oligonucleotide

<400> SEQUENCE: 1
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcactcgag     180
aacgtctata tcaaggccga caagcagaag aacggcatca aggcgaactt caagatccgc     240
cacaacatcg aggacggcgg cgtgcagctc gcctaccact accagcagaa cacccccatc     300
ggcgacggcc ccgtgctgct gcccgacaac cactacctga gcgtgcagtc caaactttcg     360
aaagacccca acgagaagcg cgatcacatg gtcctgctgg agttcgtgac cgccgccggg     420
atcactctcg gcatggacga gctgtacaag ggcggtaccg gagggagcat ggtgagcaag     480
ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
ctgacctacg gcgtgcagtg cttcagccgc taccccgacc acatgaagca gcacgacttc     720
ttcaagtccg ccatgcccga aggctacatc caggagcgca ccatcttctt caaggacgac     780
ggcaactaca agacccgcgc cgaggtgaag ttcgagggcg acaccctggt gaaccgcatc     840
gagctgaagg gcatcgactt caaggaggac ggcaacatcc tggggcacaa gctggagtac     900
aacacgcgtg accaactgac tgaagagcag atcgcagaat ttaaagaggc tttctcccta     960
tttgacaagg acggggatgg gacaataaca accaaggagc tggggacggt gatgcggtct    1020
ctggggcaga accccacaga agcagagctg caggacatga tcaatgaagt agatgccgac    1080
ggtgacggca caatcgactt ccctgagttc ctgacaatga tggcaagaaa aatgaaagac    1140
acagacagtg aagaagaaat tagagaagcg ttccgtgtgt ttgataagga tggcaatggc    1200
tacatcagtg cagcagagct tcgccacgtg atgacaaacc ttggagagaa gttaacagat    1260
gaagaggtta atgaaatgat cagggaagca gacatcgatg gggatggtca ggtaaactac    1320
gaagagtttg tacaaatgat gacagcgaag taa                                1353
```

<210> SEQ ID NO 2
<211> LENGTH: 450
<212> TYPE: PRT
<213> ORGANISM: Artificial Sequence
<220> FEATURE:
<223> OTHER INFORMATION: synthesized peptide

<400> SEQUENCE: 2

```
Met Gly Ser His His His His His Gly Met Ala Ser Met Thr Gly
1               5                   10                  15

Gly Gln Gln Met Gly Arg Asp Leu Tyr Asp Asp Asp Lys Asp Leu
                20                  25                  30

Ala Thr Met Val Asp Ser Ser Arg Lys Trp Asn Lys Thr Gly His
            35                  40                  45

Ala Val Arg Ala Ile Gly Arg Leu Ser Ser Leu Glu Asn Val Tyr Ile
50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365

Glu Phe Leu Thr Met Met Ala Arg Lys Met Lys Asp Thr Asp Ser Glu
```

```
                370             375             380
Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
            405                 410                 415

Lys Leu Thr Asp Glu Glu Val Asp Glu Met Ile Arg Glu Ala Asp Ile
                420                 425                 430

Asp Gly Asp Gly Gln Val Asn Tyr Glu Glu Phe Val Gln Met Met Thr
            435                 440                 445

Ala Lys
    450

<210> SEQ ID NO 3
<211> LENGTH: 488
<212> TYPE: PRT
<213> ORGANISM: Artificial Sequence
<220> FEATURE:
<223> OTHER INFORMATION: synthesized peptide

<400> SEQUENCE: 3

Met Gly Ser Leu Pro Asn Ser Ser Cys Leu Leu Glu Asp Lys Met Cys
1               5                   10                  15

Glu Gly Asn Lys Thr Thr Met Ala Ser Pro Gln Leu Met Pro Leu Val
                20                  25                  30

Val Val Leu Ser Thr Ile Cys Leu Val Thr Val Gly Leu Asn Leu Leu
            35                  40                  45

Val Leu Tyr Ala Val Arg Ser Glu Arg Lys Leu His Thr Val Gly Asn
50                  55                  60

Leu Tyr Ile Val Ser Leu Ser Val Ala Asp Leu Ile Val Gly Ala Val
65                  70                  75                  80

Val Met Pro Met Asn Ile Leu Tyr Leu Leu Met Ser Lys Trp Ser Leu
                85                  90                  95

Gly Arg Pro Leu Cys Leu Phe Trp Leu Ser Met Asp Tyr Val Ala Ser
                100                 105                 110

Thr Ala Ser Ile Phe Ser Val Phe Ile Leu Cys Ile Asp Arg Tyr Arg
            115                 120                 125

Ser Val Gln Gln Pro Leu Arg Tyr Leu Lys Tyr Arg Thr Lys Thr Arg
130                 135                 140

Ala Ser Ala Thr Ile Leu Gly Ala Trp Phe Leu Ser Phe Leu Trp Val
145                 150                 155                 160

Ile Pro Ile Leu Gly Trp Asn His Phe Met Gln Gln Thr Ser Val Arg
                165                 170                 175

Arg Glu Asp Lys Cys Glu Thr Asp Phe Tyr Asp Val Thr Trp Phe Lys
            180                 185                 190

Val Met Thr Ala Ile Ile Asn Phe Tyr Leu Pro Thr Leu Leu Met Leu
            195                 200                 205

Trp Phe Tyr Ala Lys Ile Tyr Lys Ala Val Arg Gln His Cys Gln His
210                 215                 220

Arg Glu Leu Ile Asn Arg Ser Leu Pro Ser Phe Ser Glu Ile Lys Leu
225                 230                 235                 240

Arg Pro Glu Asn Pro Lys Gly Asp Ala Lys Lys Pro Gly Lys Glu Ser
                245                 250                 255

Pro Trp Glu Val Leu Lys Arg Lys Pro Lys Asp Ala Gly Gly Gly Ser
            260                 265                 270

Val Leu Lys Ser Pro Ser Gln Thr Pro Lys Glu Met Lys Ser Pro Val
            275                 280                 285
```

```
Val Phe Ser Gln Glu Asp Asp Arg Glu Val Asp Lys Leu Tyr Cys Phe
    290                 295                 300

Pro Leu Asp Ile Val His Met Gln Ala Ala Glu Gly Ser Ser Arg
305                 310                 315                 320

Asp Tyr Val Ala Val Asn Arg Ser His Gly Gln Leu Lys Thr Asp Glu
                325                 330                 335

Gln Gly Leu Asn Thr His Gly Ala Ser Glu Ile Ser Glu Asp Gln Met
                340                 345                 350

Leu Gly Asp Ser Gln Ser Phe Ser Arg Thr Asp Ser Asp Thr Thr Thr
            355                 360                 365

Glu Thr Ala Pro Gly Lys Gly Lys Leu Arg Ser Gly Ser Asn Thr Gly
370                 375                 380

Leu Asp Tyr Ile Lys Phe Thr Trp Lys Arg Leu Arg Ser His Ser Arg
385                 390                 395                 400

Gln Tyr Val Ser Gly Leu His Met Asn Arg Glu Arg Lys Ala Ala Lys
                405                 410                 415

Gln Leu Gly Phe Ile Met Ala Ala Phe Ile Leu Cys Trp Ile Pro Tyr
                420                 425                 430

Phe Ile Phe Phe Met Val Ile Ala Phe Cys Lys Asn Cys Cys Asn Glu
            435                 440                 445

His Leu His Met Phe Thr Ile Trp Leu Gly Tyr Ile Asn Ser Thr Leu
450                 455                 460

Asn Pro Leu Ile Tyr Pro Leu Cys Asn Glu Asn Phe Lys Lys Thr Phe
465                 470                 475                 480

Lys Arg Ile Leu His Ile Arg Ser
                485

<210> SEQ ID NO 4
<211> LENGTH: 1467
<212> TYPE: DNA
<213> ORGANISM: Artificial Sequence
<220> FEATURE:
<223> OTHER INFORMATION: Oligonucleotide

<400> SEQUENCE: 4
atgggcagtc tcccgaatag ttcctgtctg ctggaagata aaatgtgcga aggaaacaaa      60
accacgatgg ccagcccgca gttgatgcct cttgtcgtgg tgctgtcaac catctgcctg     120
gtcaccgtcg gcctcaatct gcttgtgctg tacgccgttc gctctgagag aaagctgcat     180
accgtgggga tctctacat cgtatccctg tccgtggctg atctgatcgt gggcgctgtt     240
gtgatgccta tgaatattct gtacctgctc atgtctaagt ggagcctcgg tagaccactg     300
tgcctctttt ggttgagcat ggactacgtc gcgtcaaccg caagcatctt cagcgtgttc     360
atcttgtgca ttgatcggta cagatcagtg cagcagccac tgagatacct taagtacagg     420
accaaaacgc gagcttctgc tactattctg ggcgcctggt ttctgtcttt tctgtgggtg     480
attcctatcc ttgggtggaa tcacttcatg cagcagacga gtgttaggcg cgaagacaaa     540
tgcgagacag attttacga cgttacgtgg ttcaaggtga tgcagctat aattaatttt     600 tacctcccca cccttctgat gctttggttc tatgccaaga tttacaaggc cgtgagacag     660
cattgtcaac accgagaact tattaatcgg agcctgccct cttttccga aatcaaactc     720 cgccccgaga acccaaaggg tgacgctaag aaacctggta aggagtctcc ctgggaagtt     780
ctcaagcgca aacctaaaga tgctggaggc ggctccgtgc tgaaatcacc tagccagaca     840
cctaaagaga tgaaaagtcc cgtagtattc tcccaggagg acgaccggga ggtagataaa     900
```

-continued

```
ctttactgtt tcccactgga catcgtacac atgcaagctg ctgccgaagg ttccagccgc    960
gattacgtgg ctgtgaatcg gagtcacggc cagttgaaaa ctgatgagca ggggctgaat   1020
actcacggtg caagtgaaat cagcgaggac caaatgttgg gagattccca atctttcagc   1080
agaaccgact ccgatacaac caccgaaacc gctccaggca agggaaaact taggagtggc   1140
tccaacactg gcctggatta tatcaaattt acttggaaga ggctgagaag ccacagccgg   1200
cagtacgttt ccggtcttca catgaaccga gagcgcaagg cagccaagca gctcggcttc   1260
atcatggctg catttatctt gtgctggata ccctacttta ttttcttcat ggtgatcgcg   1320
ttctgcaaga actgttgtaa cgagcatctg cacatgttta ctatctggct cggctacatt   1380
aactccactc tgaacccact catctacccg ctgtgtaacg agaactttaa gaagacttc    1440 aagcggattc tgcacatccg aagctag                                       1467
```

<210> SEQ ID NO 5
<211> LENGTH: 1350
<212> TYPE: DNA
<213> ORGANISM: Artificial Sequence
<220> FEATURE:
<223> OTHER INFORMATION: Oligonucleotide

<400> SEQUENCE: 5

```
atgggttctc atcatcatca tcatcatggt atggctagca tgactggtgg acagcaaatg     60
ggtcgggatc tgtacgacga tgacgataag gatctcgcca ccatggtcga ctcatcacgt    120
cgtaagtgga ataagacagg tcacgcagtc agagctatag gtcggctgag ctcactcgag    180
aacgtctata tcatggccga caagcagaag aacggcatca aggcgaactt caagatccgc    240
cacaacatcg aggacggcgg cgtgcagctc gcctaccact accagcagaa caccccccatc    300 ggcgacggcc ccgtgctgct gcccgacaac cactacctga gcacccagtc caaactttcg    360
aaagacccca cgagaagcg cgatcacatg gtcctgctgg agttcgtgac cgccgccggg    420
atcactctcg gcatggacga gctgtacaag ggcggtaccg agggagcat ggtgagcaag    480 ggcgaggagc tgttcaccgg ggtggtgccc atcctggtcg agctggacgg cgacgtaaac    540
ggccacaagt tcagcgtgtc cggcgagggt gagggcgatg ccacctacgg caagctgacc    600
ctgaagttca tctgcaccac cggcaagctg cccgtgccct ggcccaccct cgtgaccacc    660
ctgacctacg gcgtgcagtg cttcagccgc taccccgacc acatgaagca gcacgacttc    720
ttcaagtccg ccatgcccga aggctacatc caggagcgca ccatcttctt caaggacgac    780
ggcaactaca agacccgcgc cgaggtgaag ttcgagggcg acaccctggt gaaccgcatc    840
gagctgaagg gcatcgactt caaggaggac ggcaacatcc tggggcacaa gctggagtac    900
aacacgcgtg accaactgac tgaagagcag atcgcagaat ttaaagaggc tttctcccta    960
tttgacaagg acggggatgg acaataaca accaaggagc tggggacggt gatgcggtct    1020
ctggggcaga accccacaga agcagagctg caggacatga tcaatgaagt agatgccgac    1080
ggtaatggca caatcgactt ccctgagttc ctgacaatga tggcaagaaa aatgaaagac    1140
acagacagta agaagaaat tagagaagcg ttccgtgtgt ttgataagga tggcaatggc    1200
tacatcagtg cagcagagct tcgccacgtg atgacaaacc ttggagagaa gttaacagat    1260
gaagaggttg atgaaatgat cagggaagca gacatcgatg gggatggtca ggtaaactac    1320
gaagagtttg tacaaatgat gacagcgaag                                    1350
```

<210> SEQ ID NO 6
<211> LENGTH: 450
<212> TYPE: PRT

<213> ORGANISM: Artificial Sequence
<220> FEATURE:
<223> OTHER INFORMATION: synthesized peptide

<400> SEQUENCE: 6

| | | | | | | | | | | | | | | |
|---|---|---|---|---|---|---|---|---|---|---|---|---|---|---|
| Met | Gly | Ser | His | His | His | His | His | Gly | Met | Ala | Ser | Met | Thr | Gly |
| 1 | | | | 5 | | | | | 10 | | | | | 15 |
| Gly | Gln | Gln | Met | Gly | Arg | Asp | Leu | Tyr | Asp | Asp | Asp | Lys | Asp | Leu |
| | | | 20 | | | | | 25 | | | | | 30 | |
| Ala | Thr | Met | Val | Asp | Ser | Ser | Arg | Arg | Lys | Trp | Asn | Lys | Thr | Gly |  His |
| | | | 35 | | | | | 40 | | | | | 45 | |
| Ala | Val | Arg | Ala | Ile | Gly | Arg | Leu | Ser | Ser | Leu | Glu | Asn | Val | Tyr | Ile |
| | 50 | | | | | 55 | | | | | 60 | | | | |
| Met | Ala | Asp | Lys | Gln | Lys | Asn | Gly | Ile | Lys | Ala | Asn | Phe | Lys | Ile | Arg |
| 65 | | | | | 70 | | | | | 75 | | | | | 80 |
| His | Asn | Ile | Glu | Asp | Gly | Gly | Val | Gln | Leu | Ala | Tyr | His | Tyr | Gln | Gln |
| | | | | 85 | | | | | 90 | | | | | 95 | |
| Asn | Thr | Pro | Ile | Gly | Asp | Gly | Pro | Val | Leu | Leu | Pro | Asp | Asn | His | Tyr |
| | | | 100 | | | | | 105 | | | | | 110 | | |
| Leu | Ser | Thr | Gln | Ser | Lys | Leu | Ser | Lys | Asp | Pro | Asn | Glu | Lys | Arg | Asp |
| | | | 115 | | | | | 120 | | | | | 125 | | |
| His | Met | Val | Leu | Leu | Glu | Phe | Val | Thr | Ala | Ala | Gly | Ile | Thr | Leu | Gly |
| | 130 | | | | | 135 | | | | | 140 | | | | |
| Met | Asp | Glu | Leu | Tyr | Lys | Gly | Gly | Thr | Gly | Gly | Ser | Met | Val | Ser | Lys |
| 145 | | | | | 150 | | | | | 155 | | | | | 160 |
| Gly | Glu | Glu | Leu | Phe | Thr | Gly | Val | Val | Pro | Ile | Leu | Val | Glu | Leu | Asp |
| | | | | 165 | | | | | 170 | | | | | 175 | |
| Gly | Asp | Val | Asn | Gly | His | Lys | Phe | Ser | Val | Ser | Gly | Glu | Gly | Glu | Gly |
| | | | 180 | | | | | 185 | | | | | 190 | | |
| Asp | Ala | Thr | Tyr | Gly | Lys | Leu | Thr | Leu | Lys | Phe | Ile | Cys | Thr | Thr | Gly |
| | | | 195 | | | | | 200 | | | | | 205 | | |
| Lys | Leu | Pro | Val | Pro | Trp | Pro | Thr | Leu | Val | Thr | Thr | Leu | Thr | Tyr | Gly |
| | 210 | | | | | 215 | | | | | 220 | | | | |
| Val | Gln | Cys | Phe | Ser | Arg | Tyr | Pro | Asp | His | Met | Lys | Gln | His | Asp | Phe |
| 225 | | | | | 230 | | | | | 235 | | | | | 240 |
| Phe | Lys | Ser | Ala | Met | Pro | Glu | Gly | Tyr | Ile | Gln | Glu | Arg | Thr | Ile | Phe |
| | | | | 245 | | | | | 250 | | | | | 255 | |
| Phe | Lys | Asp | Asp | Gly | Asn | Tyr | Lys | Thr | Arg | Ala | Glu | Val | Lys | Phe | Glu |
| | | | 260 | | | | | 265 | | | | | 270 | | |
| Gly | Asp | Thr | Leu | Val | Asn | Arg | Ile | Glu | Leu | Lys | Gly | Ile | Asp | Phe | Lys |
| | | | 275 | | | | | 280 | | | | | 285 | | |
| Glu | Asp | Gly | Asn | Ile | Leu | Gly | His | Lys | Leu | Glu | Tyr | Asn | Thr | Arg | Asp |
| | 290 | | | | | 295 | | | | | 300 | | | | |
| Gln | Leu | Thr | Glu | Glu | Gln | Ile | Ala | Glu | Phe | Lys | Glu | Ala | Phe | Ser | Leu |
| 305 | | | | | 310 | | | | | 315 | | | | | 320 |
| Phe | Asp | Lys | Asp | Gly | Asp | Gly | Thr | Ile | Thr | Thr | Lys | Glu | Leu | Gly | Thr |
| | | | | 325 | | | | | 330 | | | | | 335 | |
| Val | Met | Arg | Ser | Leu | Gly | Gln | Asn | Pro | Thr | Glu | Ala | Glu | Leu | Gln | Asp |
| | | | 340 | | | | | 345 | | | | | 350 | | |
| Met | Ile | Asn | Glu | Val | Asp | Ala | Asp | Gly | Asn | Gly | Thr | Ile | Asp | Phe | Pro |
| | | | 355 | | | | | 360 | | | | | 365 | | |
| Glu | Phe | Leu | Thr | Met | Met | Ala | Arg | Lys | Met | Lys | Asp | Thr | Asp | Ser | Glu |
| | 370 | | | | | 375 | | | | | 380 | | | | |
| Glu | Glu | Ile | Arg | Glu | Ala | Phe | Arg | Val | Phe | Asp | Lys | Asp | Gly | Asn | Gly |
| 385 | | | | | 390 | | | | | 395 | | | | | 400 |

Tyr Ile Ser Ala Ala Glu Leu Arg His Val Met Thr Asn Leu Gly Glu
            405                 410                 415

Lys Leu Thr Asp Glu Glu Val Asp Glu Met Ile Arg Glu Ala Asp Ile
        420                 425                 430

Asp Gly Asp Gly Gln Val Asn Tyr Glu Glu Phe Val Gln Met Met Thr
        435                 440                 445

Ala Lys
    450

<210> SEQ ID NO 7
<211> LENGTH: 1350
<212> TYPE: DNA
<213> ORGANISM: Artificial Sequence
<220> FEATURE:
<223> OTHER INFORMATION: Oligonucleotide

<400> SEQUENCE: 7
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcactcgag     180
aacgtctata tcatggccga caagcagaag aacggcatca aggcgaactt caagatccgc     240
cacaacatcg aggacggcgg cgtgcagctc gcctaccact accagcagaa cacccccatc     300
ggcgacggcc ccgtgctgct gcccgacaac cactacctga gcgtgcagtc caaactttcg     360
aaagacccca cgagaagcg cgatcacatg gtcctgctgg agttcgtgac cgccgccggg     420
atcactctcg gcatggacga gctgtacaag ggcggtaccg agggagcat ggtgagcaag     480 ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
ctgacctacg gcgtgcagtg cttcagccgc taccccgacc acatgaagca gcacgacttc     720
ttcaagtccg ccatgcccga aggctacatc caggagcgca ccatcttctt caaggacgac     780
ggcaactaca agacccgcgc cgaggtgaag ttcgagggcg acaccctggt gaaccgcatc     840
gagctgaagg gcatcgactt caaggaggac ggcaacatcc tggggcacaa gctggagtac     900
aacacgcgtg accaactgac tgaagagcag atcgcagaat ttaaagaggc tttctcccta     960
tttgacaagg acggggatgg gacaataaca accaaggagc tggggacggt gatgcggtct    1020
ctggggcaga accccacaga agcagagctg caggacatga tcaatgaagt agatgccgac    1080
ggtaatggca atcgactt ccctgagttc ctgacaatga tggcaagaaa aatgaaagac    1140
acagacagtg aagaagaaat tagagaagcg ttccgtgtgt ttgataagga tggcaatggc    1200
tacatcagtg cagcagagct tcgccacgtg atgacaaacc ttggagagaa gttaacagat    1260
gaagaggttg atgaaatgat cagggaagca gacatcgatg gggatggtca ggtaaactac    1320
gaagagtttg tacaaatgat gacagcgaag                                   1350

<210> SEQ ID NO 8
<211> LENGTH: 450
<212> TYPE: PRT
<213> ORGANISM: Artificial Sequence
<220> FEATURE:
<223> OTHER INFORMATION: synthesized peptide

<400> SEQUENCE: 8

Met Gly Ser His His His His His His Gly Met Ala Ser Met Thr Gly

-continued

```
1               5               10              15
Gly Gln Gln Met Gly Arg Asp Leu Tyr Asp Asp Asp Lys Asp Leu
                20              25              30

Ala Thr Met Val Asp Ser Ser Arg Arg Lys Trp Asn Lys Thr Gly His
        35              40              45

Ala Val Arg Ala Ile Gly Arg Leu Ser Ser Leu Glu Asn Val Tyr Ile
50              55              60

Met Ala Asp Lys Gln Lys Asn Gly Ile Lys Ala Asn Phe Lys Ile Arg
65              70              75              80

His Asn Ile Glu Asp Gly Gly Val Gln Leu Ala Tyr His Tyr Gln Gln
                85              90              95

Asn Thr Pro Ile Gly Asp Gly Pro Val Leu Leu Pro Asp Asn His Tyr
            100             105             110

Leu Ser Val Gln Ser Lys Leu Ser Lys Asp Pro Asn Glu Lys Arg Asp
            115             120             125

His Met Val Leu Leu Glu Phe Val Thr Ala Ala Gly Ile Thr Leu Gly
            130             135             140

Met Asp Glu Leu Tyr Lys Gly Thr Gly Gly Ser Met Val Ser Lys
145             150             155             160

Gly Glu Glu Leu Phe Thr Gly Val Val Pro Ile Leu Val Glu Leu Asp
                165             170             175

Gly Asp Val Asn Gly His Lys Phe Ser Val Ser Gly Glu Gly Glu Gly
                180             185             190

Asp Ala Thr Tyr Gly Lys Leu Thr Leu Lys Phe Ile Cys Thr Thr Gly
                195             200             205

Lys Leu Pro Val Pro Trp Pro Thr Leu Val Thr Thr Leu Thr Tyr Gly
210             215             220

Val Gln Cys Phe Ser Arg Tyr Pro Asp His Met Lys Gln His Asp Phe
225             230             235             240

Phe Lys Ser Ala Met Pro Glu Gly Tyr Ile Gln Glu Arg Thr Ile Phe
                245             250             255

Phe Lys Asp Asp Gly Asn Tyr Lys Thr Arg Ala Glu Val Lys Phe Glu
                260             265             270

Gly Asp Thr Leu Val Asn Arg Ile Glu Leu Lys Gly Ile Asp Phe Lys
                275             280             285

Glu Asp Gly Asn Ile Leu Gly His Lys Leu Glu Tyr Asn Thr Arg Asp
            290             295             300

Gln Leu Thr Glu Glu Gln Ile Ala Glu Phe Lys Glu Ala Phe Ser Leu
305             310             315             320

Phe Asp Lys Asp Gly Asp Gly Thr Ile Thr Thr Lys Glu Leu Gly Thr
                325             330             335

Val Met Arg Ser Leu Gly Gln Asn Pro Thr Glu Ala Glu Leu Gln Asp
                340             345             350

Met Ile Asn Glu Val Asp Ala Asp Gly Asn Gly Thr Ile Asp Phe Pro
            355             360             365

Glu Phe Leu Thr Met Met Ala Arg Lys Met Lys Asp Thr Asp Ser Glu
            370             375             380

Glu Glu Ile Arg Glu Ala Phe Arg Val Phe Asp Lys Asp Gly Asn Gly
385             390             395             400

Tyr Ile Ser Ala Ala Glu Leu Arg His Val Met Thr Asn Leu Gly Glu
                405             410             415

Lys Leu Thr Asp Glu Glu Val Asp Glu Met Ile Arg Glu Ala Asp Ile
            420             425             430
```

```
Asp Gly Asp Gly Gln Val Asn Tyr Glu Glu Phe Val Gln Met Met Thr
        435                 440                 445

Ala Lys
    450

<210> SEQ ID NO 9
<211> LENGTH: 1350
<212> TYPE: DNA
<213> ORGANISM: Artificial Sequence
<220> FEATURE:
<223> OTHER INFORMATION: Oligonucleotide

<400> SEQUENCE: 9
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcactcgag     180
aacgtctata tcatggccga caagcagaag aacggcatca aggcgaactt caagatccgc     240
cacaacatcg aggacggcgg cgtgcagctc gcctaccact accagcagaa cacccccatc     300
ggcgacggcc ccgtgctgct gcccgacaac cactacctga gcacccagtg caaactttcg     360
aaagacccca cgagaagcg cgatcacatg gtcctgctgg agttcgtgac cgccgccggg     420
atcactctcg gcatggacga gctgtacaag gcggtaccg agggagcat ggtgagcaag     480 ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
ctgacctacg gcgtgcagtg cttcagccgc taccccgacc acatgaagca gcacgacttc     720
ttcaagtccg ccatgcccga aggctacatc caggagcgca ccatcttctt caaggacgac     780
ggcaactaca agacccgcgc cgaggtgaag ttcgagggcg acaccctggt gaaccgcatc     840
gagctgaagg gcatcgactt caaggaggac ggcaacatcc tggggcacaa gctggagtac     900
aacacgcgtg accaactgac tgaagagcag atcgcagaat ttaaagaggc tttctcccta     960
tttgacaagg acgggatgg acaataaca ccaaggagc tggggacggt gatgcggtct    1020
ctggggcaga acccccacaga agcagagctg caggacatga tcaatgaagt agatgccgac    1080
ggtaatggca caatcgactt ccctgagttc ctgacaatga tggcaagaaa atgaaagac    1140 acagacagtg aagaagaaat tagagaagcg ttccgtgtgt ttgataagga tggcaatggc    1200
tacatcagtg cagcagagct tcgccacgtg atgacaaacc ttggagagaa gttaacagat    1260
gaagaggttg atgaaatgat cagggaagca gacatcgatg gggatggtca ggtaaactac    1320
gaagagtttg tacaaatgat gacagcgaag                                     1350

<210> SEQ ID NO 10
<211> LENGTH: 450
<212> TYPE: PRT
<213> ORGANISM: Artificial Sequence
<220> FEATURE:
<223> OTHER INFORMATION: synthesized peptide

<400> SEQUENCE: 10

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45
```

```
Ala Val Arg Ala Ile Gly Arg Leu Ser Ser Leu Glu Asn Val Tyr Ile
         50                  55                  60
Met Ala Asp Lys Gln Lys Asn Gly Ile Lys Ala Asn Phe Lys Ile Arg
 65                  70                  75                  80
His Asn Ile Glu Asp Gly Gly Val Gln Leu Ala Tyr His Tyr Gln Gln
                 85                  90                  95
Asn Thr Pro Ile Gly Asp Gly Pro Val Leu Leu Pro Asp Asn His Tyr
                100                 105                 110
Leu Ser Thr Gln Cys Lys Leu Ser Lys Asp Pro Asn Glu Lys Arg Asp
                115                 120                 125
His Met Val Leu Leu Glu Phe Val Thr Ala Ala Gly Ile Thr Leu Gly
        130                 135                 140
Met Asp Glu Leu Tyr Lys Gly Gly Thr Gly Gly Ser Met Val Ser Lys
145                 150                 155                 160
Gly Glu Glu Leu Phe Thr Gly Val Val Pro Ile Leu Val Glu Leu Asp
                165                 170                 175
Gly Asp Val Asn Gly His Lys Phe Ser Val Ser Gly Glu Gly Glu Gly
                180                 185                 190
Asp Ala Thr Tyr Gly Lys Leu Thr Leu Lys Phe Ile Cys Thr Thr Gly
                195                 200                 205
Lys Leu Pro Val Pro Trp Pro Thr Leu Val Thr Thr Leu Thr Tyr Gly
        210                 215                 220
Val Gln Cys Phe Ser Arg Tyr Pro Asp His Met Lys Gln His Asp Phe
225                 230                 235                 240
Phe Lys Ser Ala Met Pro Glu Gly Tyr Ile Gln Glu Arg Thr Ile Phe
                245                 250                 255
Phe Lys Asp Asp Gly Asn Tyr Lys Thr Arg Ala Glu Val Lys Phe Glu
                260                 265                 270
Gly Asp Thr Leu Val Asn Arg Ile Glu Leu Lys Gly Ile Asp Phe Lys
                275                 280                 285
Glu Asp Gly Asn Ile Leu Gly His Lys Leu Glu Tyr Asn Thr Arg Asp
        290                 295                 300
Gln Leu Thr Glu Glu Gln Ile Ala Glu Phe Lys Glu Ala Phe Ser Leu
305                 310                 315                 320
Phe Asp Lys Asp Gly Asp Gly Thr Ile Thr Thr Lys Glu Leu Gly Thr
                325                 330                 335
Val Met Arg Ser Leu Gly Gln Asn Pro Thr Glu Ala Glu Leu Gln Asp
                340                 345                 350
Met Ile Asn Glu Val Asp Ala Asp Gly Asn Gly Thr Ile Asp Phe Pro
        355                 360                 365
Glu Phe Leu Thr Met Met Ala Arg Lys Met Lys Asp Thr Asp Ser Glu
        370                 375                 380
Glu Glu Ile Arg Glu Ala Phe Arg Val Phe Asp Lys Asp Gly Asn Gly
385                 390                 395                 400
Tyr Ile Ser Ala Ala Glu Leu Arg His Val Met Thr Asn Leu Gly Glu
                405                 410                 415
Lys Leu Thr Asp Glu Glu Val Asp Glu Met Ile Arg Glu Ala Asp Ile
                420                 425                 430
Asp Gly Asp Gly Gln Val Asn Tyr Glu Glu Phe Val Gln Met Met Thr
                435                 440                 445
Ala Lys
450
```

<210> SEQ ID NO 11
<211> LENGTH: 1350
<212> TYPE: DNA
<213> ORGANISM: Artificial Sequence
<220> FEATURE:
<223> OTHER INFORMATION: Oligonucleotide

<400> SEQUENCE: 11

```
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcactcgag     180
aacgtctata tcaaggccga caagcagaag aacggcatca aggcgaactt caagatccgc     240
cacaacatcg aggacggcgg cgtgcagctc gcctaccact accagcagaa cacccccatc     300
ggcgacggcc ccgtgctgct gcccgacaac cactacctga gcgtgcagtc caaactttcg     360
aaagacccca cgagaagcg cgatcacatg gtcctgctgg agttcgtgac cgccgccggg     420
atcactctcg gcatggacga gctgtacaag gcggtaccg agggagcat ggtgagcaag     480
ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
ctgacctacg gcgtgcagtg cttcagccgc taccccgacc acatgaagca gcacgacttc     720
ttcaagtccg ccatgcccga aggctacatc caggagcgca ccatcttctt caaggacgac     780
ggcaactaca agacccgcgc cgaggtgaag ttcgagggcg acaccctggt gaaccgcatc     840
gagctgaagg gcatcgactt caaggaggac ggcaacatcc tggggcacaa gctggagtac     900
aacacgcgtg accaactgac tgaagagcag atcgcagaat ttaaagaggc tttctcccta     960
tttgacaagg acggggatgg gacaataaca accaaggagc tggggacggt gatgcggtct    1020
ctggggcaga accccacaga gcagagctg caggacatga tcaatgaagt agatgccgac    1080
ggtaatggca caatcgactt ccctgagttc ctgacaatga tggcaagaaa aatgaaagac    1140
acagacagta agaagaaat tagagaagcg ttccgtgtgt ttgataagga tggcaatggc    1200
tacatcagtg cagcagagct tcgccacgtg atgacaaacc ttggagagaa gttaacagat    1260
gaagaggttg atgaaatgat cagggaagca gacatcgatg gggatggtca ggtaaactac    1320
gaagagtttg tacaaatgat gacagcgaag                                    1350
```

<210> SEQ ID NO 12
<211> LENGTH: 450
<212> TYPE: PRT
<213> ORGANISM: Artificial Sequence
<220> FEATURE:
<223> OTHER INFORMATION: synthesized peptide

<400> SEQUENCE: 12

```
Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80
```

His Asn Ile Glu Asp Gly Gly Val Gln Leu Ala Tyr His Tyr Gln Gln
                    85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asn Gly Thr Ile Asp Phe Pro
        355                 360                 365

Glu Phe Leu Thr Met Met Ala Arg Lys Met Lys Asp Thr Asp Ser Glu
    370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 13
<211> LENGTH: 1350
<212> TYPE: DNA
<213> ORGANISM: Artificial Sequence
<220> FEATURE:
<223> OTHER INFORMATION: Oligonucleotide -continued

```
<400> SEQUENCE: 13
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcactcgag     180
aacgtctata tcatggccga caagcagaag aacggcatca aggcgaactt caagatccgc     240
cacaacatcg aggacggcgg cgtgcagctc gcctaccact accagcagaa cccccccatc     300
ggcgacggcc ccgtgctgct gcccgacaac cactacctga gcgtgcagtc caaactttcg     360
aaagacccca cgagaagcg cgatcacatg gtcctgctgg agttcgtgac cgccgccggg      420
atcactctcg gcatggacga gctgtacaag ggcggtaccg agggagcat ggtgagcaag      480 ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
ctgacctacg gcgtgcagtg cttcagccgc taccccgacc acatgaagca gcacgacttc     720
ttcaagtccg ccatgcccga aggctacatc caggagcgca ccatcttctt caaggacgac     780
ggcaactaca agacccgcgc cgaggtgaag ttcgagggcg acaccctggt gaaccgcatc     840
gagctgaagg gcatcgactt caaggaggac ggcaacatcc tggggcacaa gctggagtac     900
aacacgcgtg accaactgac tgaagagcag atcgcagaat ttaaagaggc tttctcccta     960
tttgacaagg acggggatgg gacaataaca accaaggagc tggggacggt gatgcggtct    1020
ctggggcaga accccacaga agcagagctg caggacatga tcaatgaagt agatgccgac    1080
ggtgacggca caatcgactt ccctgagttc ctgacaatga tggcaagaaa aatgaaagac    1140
acagacagtg aagaagaaat tagagaagcg ttccgtgtgt ttgataagga tggcaatggc    1200
tacatcagtg cagcagagct tcgccacgtg atgacaaacc ttggagagaa gttaacagat    1260
gaagaggttg atgaaatgat cagggaagca gacatcgatg gggatggtca ggtaaactac    1320
gaagagtttg tacaaatgat gacagcgaag                                     1350

<210> SEQ ID NO 14
<211> LENGTH: 450
<212> TYPE: PRT
<213> ORGANISM: Artificial Sequence
<220> FEATURE:
<223> OTHER INFORMATION: synthesized peptide

<400> SEQUENCE: 14

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Met Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
```

```
                    115                 120                 125
    His Met Val Leu Leu Glu Phe Val Thr Ala Ala Gly Ile Thr Leu Gly
        130                 135                 140

Met Asp Glu Leu Tyr Lys Gly Thr Gly Gly Ser Met Val Ser Lys
145                 150                 155                 160

Gly Glu Glu Leu Phe Thr Gly Val Val Pro Ile Leu Val Glu Leu Asp
                    165                 170                 175

Gly Asp Val Asn Gly His Lys Phe Ser Val Ser Gly Glu Gly Glu Gly
                    180                 185                 190

Asp Ala Thr Tyr Gly Lys Leu Thr Leu Lys Phe Ile Cys Thr Thr Gly
                    195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
    225                 230                 235                 240

Phe Lys Ser Ala Met Pro Glu Gly Tyr Ile Gln Glu Arg Thr Ile Phe
                    245                 250                 255

Phe Lys Asp Asp Gly Asn Tyr Lys Thr Arg Ala Glu Val Lys Phe Glu
                    260                 265                 270

Gly Asp Thr Leu Val Asn Arg Ile Glu Leu Lys Gly Ile Asp Phe Lys
                    275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
    305                 310                 315                 320

Phe Asp Lys Asp Gly Asp Gly Thr Ile Thr Thr Lys Glu Leu Gly Thr
                    325                 330                 335

Val Met Arg Ser Leu Gly Gln Asn Pro Thr Glu Ala Glu Leu Gln Asp
                    340                 345                 350

Met Ile Asn Glu Val Asp Ala Asp Gly Asp Gly Thr Ile Asp Phe Pro
                    355                 360                 365

Glu Phe Leu Thr Met Met Ala Arg Lys Met Lys Asp Thr Asp Ser Glu
    370                 375                 380

Glu Glu Ile Arg Glu Ala Phe Arg Val Phe Asp Lys Asp Gly Asn Gly
    385                 390                 395                 400

Tyr Ile Ser Ala Ala Glu Leu Arg His Val Met Thr Asn Leu Gly Glu
                    405                 410                 415

Lys Leu Thr Asp Glu Glu Val Asp Glu Met Ile Arg Glu Ala Asp Ile
                    420                 425                 430

Asp Gly Asp Gly Gln Val Asn Tyr Glu Glu Phe Val Gln Met Met Thr
                    435                 440                 445

Ala Lys
        450

<210> SEQ ID NO 15
<211> LENGTH: 451
<212> TYPE: PRT
<213> ORGANISM: Artificial Sequence
<220> FEATURE:
<223> OTHER INFORMATION: synthesized peptide

<400> SEQUENCE: 15

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30
```

```
Leu Ala Thr Met Val Asp Ser Ser Arg Arg Lys Trp Asn Lys Thr Gly
             35                  40                  45

His Ala Val Arg Ala Ile Gly Arg Leu Ser Ser Leu Glu Asn Val Tyr
 50                  55                  60

Ile Met Ala Asp Lys Gln Lys Asn Gly Ile Lys Ala Asn Phe Lys Ile
 65                  70                  75                  80

Arg His Asn Ile Glu Asp Gly Val Gln Leu Ala Tyr His Tyr Gln
                 85                  90                  95

Gln Asn Thr Pro Ile Gly Asp Gly Pro Val Leu Leu Pro Asp Asn His
                100                 105                 110

Tyr Leu Ser Thr Gln Ser Lys Leu Ser Lys Asp Pro Asn Glu Lys Arg
                115                 120                 125

Asp His Met Val Leu Leu Glu Phe Val Thr Ala Ala Gly Ile Thr Leu
                130                 135                 140

Gly Met Asp Glu Leu Tyr Lys Gly Gly Thr Gly Gly Ser Met Val Ser
145                 150                 155                 160

Lys Gly Glu Glu Leu Phe Thr Gly Val Val Pro Ile Leu Val Glu Leu
                165                 170                 175

Asp Gly Asp Val Asn Gly His Lys Phe Ser Val Ser Gly Glu Gly Glu
                180                 185                 190

Gly Asp Ala Thr Tyr Gly Lys Leu Thr Leu Lys Phe Ile Cys Thr Thr
                195                 200                 205

Gly Lys Leu Pro Val Pro Trp Pro Thr Leu Val Thr Thr Leu Thr Tyr
210                 215                 220

Gly Val Gln Cys Phe Ser Arg Tyr Pro Asp His Met Lys Gln His Asp
225                 230                 235                 240

Phe Phe Lys Ser Ala Met Pro Glu Gly Tyr Ile Gln Glu Arg Thr Ile
                245                 250                 255

Phe Phe Lys Asp Asp Gly Asn Tyr Lys Thr Arg Ala Glu Val Lys Phe
                260                 265                 270

Glu Gly Asp Thr Leu Val Asn Arg Ile Glu Leu Lys Gly Ile Asp Phe
                275                 280                 285

Lys Glu Asp Gly Asn Ile Leu Gly His Lys Leu Glu Tyr Asn Thr Arg
290                 295                 300

Asp Gln Leu Thr Glu Glu Gln Ile Ala Glu Phe Lys Glu Ala Phe Ser
305                 310                 315                 320

Leu Phe Asp Lys Asp Gly Asp Gly Thr Ile Thr Thr Lys Glu Leu Gly
                325                 330                 335

Thr Val Met Arg Ser Leu Gly Gln Asn Pro Thr Glu Ala Glu Leu Gln
                340                 345                 350

Asp Met Ile Asn Glu Val Asp Ala Asp Gly Asn Gly Thr Ile Asp Phe
                355                 360                 365

Pro Glu Phe Leu Thr Met Met Ala Arg Lys Met Lys Asp Thr Asp Ser
370                 375                 380

Glu Glu Glu Ile Arg Glu Ala Phe Arg Val Phe Asp Lys Asp Gly Asn
385                 390                 395                 400

Gly Tyr Ile Ser Ala Ala Glu Leu Arg His Val Met Thr Asn Leu Gly
                405                 410                 415

Glu Lys Leu Thr Asp Glu Glu Val Asp Glu Met Ile Arg Glu Ala Asp
                420                 425                 430
```

```
Ile Asp Gly Asp Gly Gln Val Asn Tyr Glu Glu Phe Val Gln Met Met
        435                 440                 445
Thr Ala Lys
    450
```

GENETICALLY ENCODED CALCIUM INDICATOR POLYPEPTIDES AND NUCLEIC ACIDS ENCODING SAME

CLAIM OF PRIORITY

This application is a continuation of International Application Number PCT/US2010/055451, filed Nov. 4, 2010, which claims benefit U.S. Provisional Application No. 61/258,738, filed Nov. 6, 2009, the entire contents of which applications are hereby incorporated by reference in their entireties.

BACKGROUND

Almost half of pharmaceuticals on the market target G-protein coupled receptors (GPCRs). A large portion of GPCRs signal through Gq proteins, which activate phospholipase C and result in flux of $Ca^{2+}$ ions through calcium channels. Initial screens of candidate GPCR agonists or antagonists are routinely performed by fluorescence imaging of a small molecule $Ca^{2+}$ signaling dye. The target (Gq-signaling) receptor is over-expressed in a cell line and the cells are incubated with a $Ca^{2+}$ dye. Addition of an agonist increases, and an antagonist decreases, dye fluorescence. Titration of this effect, and/or competition with endogenous agonist, reveals an apparent Ki of inhibition of the receptor. Another large (and growing) class of drug targets is ion channels themselves (many of which conduct $Ca^{2+}$). Imaging $[Ca^{2+}]$ is a direct measurement of the activity of Gq GPCRs and cation channels, and visualization of $[Ca^{2+}]$ flux is useful for assaying the effect of potential drugs on such protein targets.

Calcium is a universal second messenger regulating essential cellular signaling events in a broad range of tissues and organisms. In neurons, action potentials (APs) trigger large and rapid changes in cytoplasmic free calcium. Similarly, activation of synaptic glutamate receptors during synaptic transmission produces $[Ca^{2+}]$ transients in dendritic spines. Calcium imaging using synthetic calcium indicators has been used to measure neuronal spiking and synaptic input across populations of neurons in vitro and in vivo. However, synthetic indicators are difficult to target to specific cell types or sub-cellular locations. The loading procedures are invasive and damaging to neural tissue, precluding repeated, chronic in vivo measurements.

SUMMARY

Provided herein are nucleic acid sequences and polypeptides encoding a genetically encoded calcium indicator (GECI). Also provided are vectors and cells comprising the nucleic acid sequences and/or polypeptides. Kits comprising the nucleic acid sequences, polypeptides, vectors, cells and combinations thereof are also provided. Also provided herein are methods of screening for G-protein coupled receptor (GPCR) agonists and antagonists and methods of monitoring neural activity using the GECIs.

The details of one or more embodiments are set forth in the accompanying drawings and the description below. Other features, objects, and advantages will be apparent from the description and drawings, and from the claims.

BRIEF DESCRIPTION OF THE DRAWINGS

FIGS. 1A-1E show the in vitro characterization of GCaMP3. FIG. 1A is a graph showing screening resulted in several mutants with improved baseline brightness and signal change in HEK293 cells. FIG. 1B is a schematic representation of GCaMP2 and GCaMP3. Mutated residues are shown below GCaMP3. FIG. 1C is a graph of the fluorescence spectra of GCaMP3 and GCaMP2 (1 μM protein) with 1 mM $Ca^{2+}$ or 10 mM EGTA in MOPS buffer (30 mM MOPS, 100 mM KCl, pH 7.5) (average of three independent measurements). The fluorescence intensity of each indicator was normalized to the peak of the calcium-saturated spectrum. The inset shows the un-normalized fluorescence emission spectra (485 nm excitation). FIG. 1D is a graph of the $Ca^{2+}$ titration curve (1 μM protein) in MOPS buffer. Inset shows the dynamic range of the two indicators. FIG. 1E is images (left) and a graph (right) showing the improved baseline fluorescence of GCaMP3 compared to GCaMP2. Both indicators were either transfected to HEK293 cells or virally delivered to layer 2/3 cortical neurons. Images were taken either 48 hours post-transfection or 12 days post-viral injection, then analyzed with VOLOCITY® 5.0 (Improvision Imaging Processing & Vision Co., Coventry, England). 50 μm scale bar. Error bars indicate standard deviation of the mean.

FIGS. 2A-2H show the action potential-evoked response of GCaMP3 in hippocampal pyramidal and layer 2/3 cortical neurons. FIG. 2A is an image showing the linescan location at the base of the apical dendrite and evoked action potentials in the soma. 10 μm scale bar. Raw linescan images showing fluorescence baseline and single action potential-evoked responses. FIG. 2B shows images of the average-trial responses of GCaMP3 for individual hippocampal pyramidal cells in organotypic slices (n=9 cells, thin gray lines) and mean across all cells (thick black line) for each stimulus. Note different y-axis scales for each panel. FIG. 2C is an image showing expression of GCaMP3 in layer 2/3 cortical neurons (S1) via in utero electroporation. 20 μm scale bar. FIG. 2D shows images of average-trial responses of GCaMP3 for individual layer 2/3 cortical cells (n=9 cells, thin gray lines) in response to trains of action potentials given at 83 Hz, and the mean across cells (thick black line). Note different y-axis scales for each panel. FIGS. 2E and 2F are graphs showing amplitudes (FIG. 2E) and SNR (FIG. 2F) of GCaMP3 responses for individual hippocampal pyramidal cells (thin gray lines) in response to trains of action potentials given at 83 Hz, and the mean across cells (thick black line). FIG. 2G is a graph showing the average response of GCaMP3 is greater than GCaMP2. FIG. 2H is a graph showing the SNR of GCaMP3 is also greater than GCaMP2. Error bars indicate standard deviation of the mean.

FIG. 3A is a schematic representation of the FRET-based calcium indicators D3cpV and TN-XXL. FIG. 3B shows graphs of the mean of fluorescence responses for action potential trains across cells (n=7 cells, 1 trial each cell). Traces from bottom to top represent the response to trains of 1, 2, 3, 5, 10, 20 and 40 APs. FIG. 3C shows graphs of the ratio change of D3cpV and TN-XXL for individual hippocampal pyramidal cells (thin gray lines) in response to trains of action potentials given at 83 Hz, and the mean across cells (thick black line). FIG. 3D shows graphs of signal-to-noise ratio (SNR) of D3cpV and TN-XXL. FIGS. 3E and 3F shows graphs of the comparison of mean responses (ΔF/F or ΔR/R) and SNR of GCaMP3, D3cpV and TN-XXL. Zoom of lower stimuli is shown in inset. FIG. 3G is a graph showing the mean cellular fluorescence during periodic two-photon frame scans (n=3-4 cells per GECI). FIG. 3H shows graphs of the rise and decay time comparison of all three indicators at 10 APs. Error bars indicate standard deviation of the mean.

FIGS. 4A and 4B show graphs of the effect of odour presentation on fluorescence intensity. Upon odour presentation, GCaMP3 and GCaMP2 showed a similar decrease in fluorescence intensity. FIGS. 4C and 4D show graphs of the effect of odour removal on fluorescence intensity. Upon odour removal, GCaMP3 showed a 4- to 5-fold increase of fluorescence response compared to GCaMP2 and GCaMP1. Grey bars denote odour presence. Shading of each trace and error bars indicate standard error of the mean (S.E.M., n=12 animals for each genotype).

FIG. 5A shows images of GCaMP1.6 and GCaMP3 expression in DM2 glomeruli of the AL. DM2 ROI, circled with dashed line, was used for framescans. 10 µm scale bar. FIG. 5B shows graphs of DM2 framescan responses of GCaMP1.6 and GCaMP3 to presentations of vinegar. 5-trial average response of a single animal each, expressing GCaMP1.6 (left panel) or GCaMP3 (right panel). FIG. 5C is a graph showing peak response of GCaMP1.6 (4ALs from 3 animals) and GCaMP3 (4ALs from 4 animals) across all trials and animals. The response of GCaMP3 was increased ~4-fold compared to GCaMP1.6. Comparisons shown here are significant (p=6.80e-08, Mann-Whitney Test). Error bars indicate standard deviation of the mean.

FIG. 6A is a schematic illustrating simultaneous two-photon imaging and electrophysiology in virally infected L2/3 neurons in vivo. FIG. 6B shows examples of single-trial responses (gray line) and average across 10 trials (black line) of evoked (50 Hz) APs in three neurons under anesthesia. FIG. 6C is a graph of GCaMP3 (linear ΔF/F) with evoked APs (n=9 cells, thin gray lines; average of 10 trials per neuron, thick black line). FIG. 6D is a graph showing cumulative distribution of the decay times ($T_{1/2}$, single-exponential fit from last fluorescence maximum). Decay times of neurons with nuclear exclusion are similar at 10 to 120 days (p=0.22, Kolmogorov-Smirnov test). Nuclear-filled neurons have significantly longer decay times (black line, p=5.78e-10, Kolmogorov-Smirnov test). FIG. 6E and FIG. 6F are graphs with images showing GCaMP3 expression in L2/3 neurons of the primary motor cortex at 72 days post injection (6E, top, 30 µm scale bar) and ΔF/F traces of individual cells (6F, bottom, black lines). Relative treadmill movement indicated by the top line (see 6F, F: forward, B: backward). Images show expression at 120 days post injection.

FIGS. 8A-8C show GCaMP3 outperformed the BD calcium-kit ("BD Calcium Kit") and the FLIPR calcium-5-kit ("Calcium 5") in HEK293 cells. FIG. 8A is a graph showing the kinetic data of HEK293 cells assayed using GCaMP3, the BD calcium-kit and the FLIPR calcium-5-kit. Histamine or buffer was added after reading baseline for 10 seconds at 1 second intervals. Fluorescence was measured for another 140 seconds. FIG. 8B is a graph showing the concentration-dependent response of histamine in HEK293 cells using GCaMP3, the BD calcium-kit and the FLIPR calcium-5-kit. FIG. 8C is a table showing the EC50 values and Z' factor measured from the data of FIG. 8B.

FIGS. 9A-9C show GCaMP3 outperformed the BD calcium-kit ("BD Calcium Kit") and the FLIPR calcium-5-kit ("Calcium 5") in HeLa cells. FIG. 9A is a graph showing the kinetic data of HeLa cells assayed using GCaMP3, the BD calcium-kit and the FLIPR calcium-5-kit. Histamine or buffer was added after reading baseline for 10 seconds at 1 second intervals. Fluorescence was measured for another 140 seconds. FIG. 9B is a graph showing the concentration-dependent response of histamine in HeLa cells using GCaMP3, the BD calcium-kit and the FLIPR calcium-5-kit. FIG. 9C is a table showing the EC50 values and Z' factor measured from the data of FIG. 9B.

FIG. 10A is a graph showing the concentration-dependent response of the antagonists, diphenhydramine and cetirizine, in HEK293 cells in the presence of 10 nM histamine using GCaMP3. FIG. 10B is a graph showing the concentration-dependent response of the antagonists, diphenhydramine and cetirizine, in HEK293 cells in the presence of 10 nM histamine using the FLIPR calcium-5-kit. FIG. 10C is a graph showing the concentration-dependent response of the antagonists, diphenhydramine and cetirizine, in HEK293 cells in the presence of 10 nM histamine using the BD calcium-kit.

FIG. 11A is a graph showing the concentration-dependent response of the antagonists, diphenhydramine and cetirizine, in HeLa cells in the presence of 10 nM histamine using GCaMP3. FIG. 11B is a graph showing the concentration-dependent response of the antagonists, diphenhydramine and cetirizine, in HeLa cells in the presence of 10 nM histamine using the FLIPR calcium-5-kit. FIG. 11C is a graph showing the concentration-dependent response of the antagonists, diphenhydramine and cetirizine, in HeLa cells in the presence of 10 nM histamine using the BD calcium-kit.

FIG. 12A is a graph showing the comparison of baseline brightness in various biological systems. Fluorescence intensity was measured with 10 mM EGTA. FIG. 12B shows images of cells expressing GCaMP2 in the presence or absence of lactacystin (top panel) or cells expressing GCaMP2 or GCaMP2.1 (bottom panel). FIG. 12C is a graph showing quantitation of the brightness of GCaMP2 plus lactacystin or GCaMP2.1 relative to GCaMP2. Error bars indicate standard deviation of the mean.

FIG. 13A shows the amino acid sequence of GCaMP2 (SEQ ID NO:15). The sites of site-directed mutagenesis are shown in boxes. The arginine at position 2 was deleted.

FIG. 16A are graphs of automated detection probability of GCaMP3, D3cpV and TN-XXL at given action potential trains at 83 Hz (left panel). Human blind-scoring detection probability of GCaMP3, D3cpV and TN-XXL (right panel). For blind-scoring test, the false positive rate is less than 2%. Error bars indicate standard deviation of the mean. FIG. 16B is a graph of automated detection probability of GCaMP3 in vivo (n=9 cells). Each neuron is shown in a thin gray line. The mean of 9 cells is shown in a thick gray line.

DETAILED DESCRIPTION

Figure 1C:
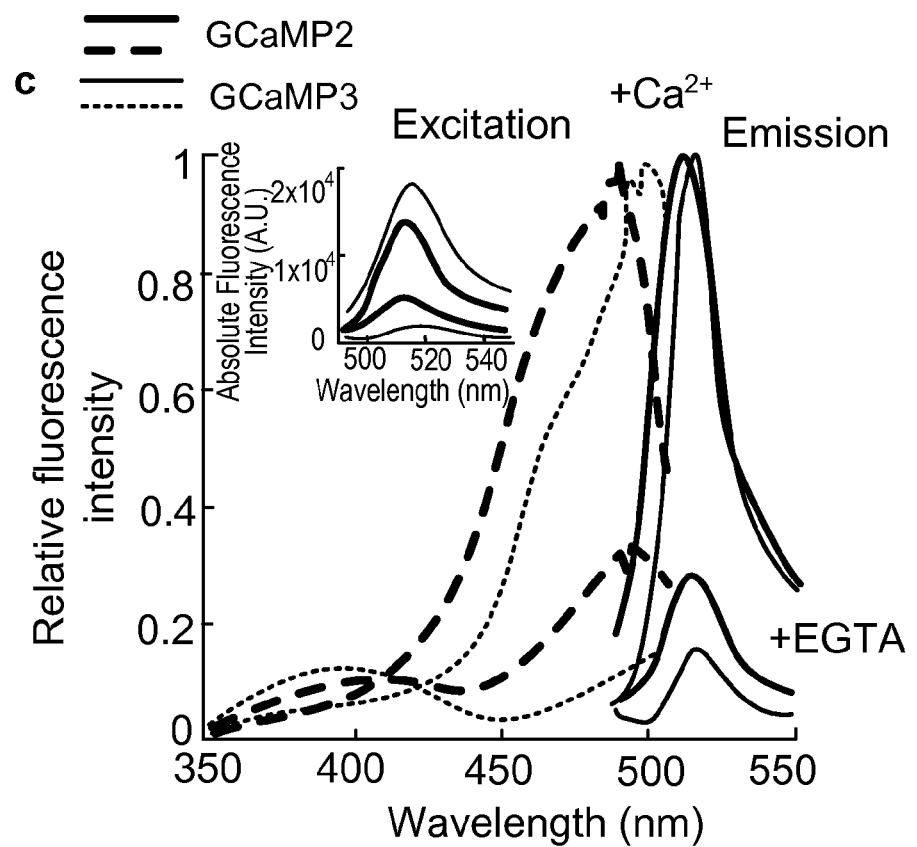

Genetically encoded calcium indicators (GECIs) (also called fluorescent calcium indicator proteins; FCIPs) provide an alternative to synthetic indicators. GECIs can be easily targeted to specific cell types or sub-cellular compartments. They are compatible with long-term, repeated in vivo measurements. GECIs consist of a calcium-binding domain such as calmodulin or troponin C, fused to one or more (e.g., one, two, three, four, or more) fluorescent proteins (FPs). In single-FP GECIs, the fluorescence intensity of a circularly permuted FP (cpFP) is modulated by calcium binding-dependent changes in the chromophore environment. In two-FP GECIs, and multiple-FP GECIs, calcium binding modulates fluorescence resonance energy transfer (FRET) between FPs.

The calmodulin-based FRET indicator D3cpVenus (D3cpV) 13 has recently been reported to detect single APs in pyramidal neurons in organotypic mouse brain slices and in vivo. The troponin C-based indicator TN-XXL has been used for chronic in vivo activity imaging in the mouse brain. Among single-FP based GECIs, the GCaMP family has found the broadest use across multiple model organisms. However, the properties of all available GECIs are still inferior to synthetic indicators in terms of signal-to-noise ratio (SNR), response linearity, photostability, and properly tuned calcium affinity. The GCaMP indicators further suffer from poor protein stability.

As described herein, GCaMP variants were developed. As shown in the examples below, GCaMP3, is brighter, possesses greater protein stability, and has a larger dynamic range and higher affinity for calcium compared to GCaMP2. GCaMP3 is more photostable than the FRET indicators D3cpV and TN-XXL and displays significantly greater sensitivity and faster kinetics, especially at higher levels of activity. GCaMP3 showed improved sensitivity in mammalian cell culture, pyramidal neurons in brain slices, and worms, flies, and mice in vivo.

Described herein are genetically encoded calcium indicators (GECIs) with signal-to-noise ratios that, in some embodiments, exceed those of commercial dyes and kits. Furthermore, the GECIs can be integrated into a cell line of interest, lowering assay-to-assay variability and obviating the need to purchase the extraordinarily expensive (and batch-to-batch variable) membrane-permeable Ca2+ dyes. As described in the examples below, using the histamine H1 receptor, the target of most antihistamine drugs, HeLa and HEK293 cell lines, and an array of agonists and antagonists, the examples show the GECIs outperform fluo-4-AM (Invitrogen, Carlsbad, Calif.), BD Calcium Kit (BD Biosciences, San Jose, Calif.), and FLIPR Calcium 5 Kit (Molecular Devices, Sunnyvale, Calif.). Using the methods described herein, it is possible to adapt the reagents to assays for a variety of classes of receptors and biomolecules. The provided materials and methods facilitate the discovery of new compounds targeting a wide array of protein targets, including but not limited to: endogenous targets responsible for disease state progression, targets on pathogens for treating infectious diseases, and endogenous targets to be avoided (thus screening early for potential drug side effects and toxicity).

Provided herein are nucleic acid sequences encoding a genetically encoded calcium indicator (GECI). Optionally, the GECI is GCaMP3. Optionally, the encoded GECI comprises SEQ ID NO: 2, SEQ ID NO:6, SEQ ID NO:8, SEQ ID NO:10, SEQ ID NO:12 or SEQ ID NO:14, optionally with one or more conservative amino acid substitutions (e.g., with one, two, three, four, five, six, seven, eight, nine, ten, fifteen, twenty, or a range between any two of the aforementioned numbers, or more than twenty conservative amino acid substitutions, so long as the desired function of the peptide is maintained (e.g., substantially maintained). In some embodiments, the number of amino acid substitutions in SEQ ID NO: 2, SEQ ID NO:6, SEQ ID NO:8, SEQ ID NO:10, SEQ ID NO:12 or SEQ ID NO:14 is expressed as a percentage of the total number of amino acids present. For example, about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 2.0%, 2.5%, 3.0%, 3.5%, 4.0%, 4.5%, 5.0%, 5.5%, 6.0%, 6.5%, 7%, 7.5%, 8.0%, 8.5%, 9.0%, 9.5%, 10.0%, 15%, 20%, 25%, 30%, 40%, 50%, or a range between any two of the aforementioned numbers, of the amino acids present in SEQ ID NO: 2, SEQ ID NO:6, SEQ ID NO:8, SEQ ID NO:10, SEQ ID NO:12 or SEQ ID NO:14 can be substituted with a conservative amino acid(s), so long as the desired function of the peptide is maintained (e.g., substantially maintained)). For example, in some instances, the nucleic acid sequence can comprise SEQ ID NO:1, SEQ ID NO:5, SEQ ID NO:7, SEQ ID NO:9, SEQ ID NO:11 or SEQ ID NO:13. In some embodiments, the nucleic acid sequence can consist or consist essentially of SEQ ID NO:1, SEQ ID NO:5, SEQ ID NO:7, SEQ ID NO:9, SEQ ID NO:11 or SEQ ID NO:13. Also provided are nucleic acid sequences encoding the GECI comprising a nucleic acid sequence at least about 70%, 75%, 80%, 85%, 90%, 95%, 98%, 99% or more identical to SEQ ID NO:1, SEQ ID NO:5, SEQ ID NO:7, SEQ ID NO:9, SEQ ID NO:11 or SEQ ID NO:13.

Also provided are polypeptides comprising a GECI (e.g., GCaMP3). Optionally, the GECI comprises SEQ ID NO: 2, SEQ ID NO:6, SEQ ID NO:8, SEQ ID NO:10, SEQ ID NO:12 or SEQ ID NO:14, optionally with one or more conservative amino acid substitutions (e.g., with one, two, three, four, five, six, seven, eight, nine, ten, fifteen, twenty, or a range between any two of the aforementioned numbers, or more than twenty conservative amino acid substitutions, so long as the desired function of the peptide is maintained (e.g., substantially maintained). In some embodiments, the number of amino acid substitutions in SEQ ID NO: 2, SEQ ID NO:6, SEQ ID NO:8, SEQ ID NO:10, SEQ ID NO:12 or SEQ ID NO:14 is expressed as a percentage of the total number of amino acids present. For example, about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 2.0%, 2.5%, 3.0%, 3.5%, 4.0%, 4.5%, 5.0%, 5.5%, 6.0%, 6.5%, 7%, 7.5%, 8.0%, 8.5%, 9.0%, 9.5%, 10.0%, 15%, 20%, 25%, 30%, 40%, 50%, or a range between any two of the aforementioned numbers, of the amino acids present in SEQ ID NO: 2, SEQ ID NO:6, SEQ ID NO:8, SEQ ID NO:10, SEQ ID NO:12 or SEQ ID NO:14 can be substituted with a conservative amino acid(s), so long as the desired function of the peptide is maintained (e.g., substantially maintained)). Also provided herein are amino acid sequences of the GECI comprising an amino acid sequence at least about 70%, 75%, 80%, 85%, 90%, 95%, 98%, 99% or more identical to SEQ ID NO: 2, SEQ ID NO:6, SEQ ID NO:8, SEQ ID NO:10, SEQ ID NO:12 or SEQ ID NO:14.

As with all peptides, polypeptides, and proteins, including fragments thereof, it is understood that additional modifications in the amino acid sequence of the GECI can occur that do not alter the nature or function of the peptides, polypeptides, or proteins. Such modifications include conservative amino acids substitutions and are discussed in greater detail below. The peptides, polypeptides, and proteins, including fragments thereof, provided herein are calcium indicators and can be tested for their desired activity using the in vitro assays described herein.

Nucleic acids that encode the polypeptide sequences, variants, and fragments thereof are disclosed. These sequences include all degenerate sequences related to the specific polypeptide sequence, i.e., all nucleic acids having a sequence that encodes one particular polypeptide sequence as well as all nucleic acids, including degenerate nucleic acids, encoding the disclosed variants and derivatives of the polypeptide sequences. Thus, while each particular nucleic acid sequence may not be written out herein, it is understood that each and every sequence is in fact disclosed and described herein through the disclosed polypeptide sequences.

The polypeptides described herein can be further modified and varied so long as the desired function is maintained. For example, the polypeptides can be further modified as long as the polypeptide variants have the same or better characteristics as GCaMP3. For example, the variants have the same or better affinity for calcium as GCaMP3. It is understood that one way to define any known modifications and derivatives or those that might arise, of the disclosed genes and proteins herein is through defining the modifications and derivatives in terms of identity to specific known sequences. In some embodiments, the interacting face of a modified peptide should be the same (e.g., substantially the same) as an unmodified peptide (methods for identifying the interacting face of a peptide are known in the art (Gong et al., BMC: Bioinformatics, 6:1471-2105 (2007); Andrade and Wei et al., Pure and Appl. Chem., 64(11):1777-1781 (1992); Choi et al., Proteins: Structure, Function, and Bioinformatics, 77(1):14-25 (2009); Park et al., BMC: and Bioinformatics, 10:1471-2105 (2009)). The interacting face of a peptide is the region of the peptide that interacts or associates with other molecules (e.g., other proteins). Generally, amino acids within the interacting face are more highly conserved than those amino acids located outside the interacting face or interface regions of a protein. In some instances the interacting face of a GECI includes those amino acids that interact with a GPCR. In some embodiments, an amino acid within the interacting face region of a GECI can be the same as the amino acid shown in SEQ ID NO: 2, SEQ ID NO:6, SEQ ID NO:8, SEQ ID NO:10, SEQ ID NO:12 or SEQ ID NO:14 or can be a conservative substitution. In some embodiments, an amino acid within the interacting face region of SEQ ID NO: 2, SEQ ID NO:6, SEQ ID NO:8, SEQ ID NO:10, SEQ ID NO:12 or SEQ ID NO:14 can be substituted with an amino acid that increases the interaction between the GECI and GPCR.

As noted above, disclosed polypeptides include those which have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the GECI and variants provided herein. Those of skill in the art readily understand how to determine the identity of two polypeptides. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman, Adv. Appl. Math, 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-10 (1989); Jaeger et al., Methods Enzymol. 183: 281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

Protein modifications include amino acid sequence modifications. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at lease one residue has been removed and a different residue inserted in its place. Such substitutions generally are made in accordance with the following Table 1 and are referred to as conservative substitutions. Methods for predicting tolerance to protein modification are known in the art (see, e.g., Guo et al., Proc. Natl. Acad. Sci., USA, 101(25):9205-9210 (2004)).

TABLE 1

Amino Acid Substitutions

| Amino Acid | Substitutions (others are known in the art) |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

Modifications, including the specific amino acid substitutions, are made by known methods. By way of example, modifications are made by site-specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

As described above, the GCaMP3 variants provided herein have the same or better characteristics than GCaMP3. For example, the GCaMP3 variants have one or more of the following characteristics: the GCaMP3 variants have the same or better affinity for calcium than GCaMP3, have the same or better protein stability as GCaMP3, have the same or better photostability as GCaMP3, have the same or better sensitivity, and/or the same or better kinetics as GCaMP3. The GCaMP3 variants can be compared to GCaMP3 using the methods described in the examples.

Also provided herein are vectors comprising GECI-encoding nucleic acid sequences. Optionally the GECI-encoding nucleic acid sequences comprise SEQ ID NO:1, SEQ ID NO:5, SEQ ID NO:7, SEQ ID NO:9, SEQ ID NO:11 or SEQ ID NO:13 and sequences with identity thereto, as noted above. Optionally, the GECI comprises SEQ ID NO: 2, SEQ ID NO:6, SEQ ID NO:8, SEQ ID NO:10, SEQ ID NO:12 or SEQ ID NO:14, and sequences with identity thereto, as noted above. Examples of suitable vectors include, but are not limited to, plasmids, artificial chromosomes, such as BACs, YACs, or PACs, and viral vectors. As used herein, vectors are agents that transport the disclosed nucleic acids into a cell without degradation and, optionally, include a promoter yielding expression of the nucleic acid molecule in the cells into which it is delivered.

Viral vectors are, for example, Adenovirus, Adeno-associated virus, herpes virus, Vaccinia virus, Polio virus, Sindbis, and other RNA viruses, including these viruses with the HIV backbone. Any viral families which share the properties of these viruses which make them suitable for use as vectors are suitable. Retroviral vectors, in general are described by Coffin et al., Retorviruses, Cold Spring Harbor Laboratory Press (1997), which is incorporated by reference herein for the vectors and methods of making them. The construction of replication-defective adenoviruses has been described (Berkner et al., J. Virology 61:1213-20 (1987); Massie et al., Mol. Cell. Biol. 6:2872-83 (1986); Haj-Ahmad et al., J. Virology 57:267-74 (1986); Davidson et al., J. Virology 61:1226-39 (1987); Zhang et al., BioTechniques 15:868-72 (1993)). Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors.

Non-viral based vectors, can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Pal Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. β-actin promoter or EF1α promoter, or from hybrid or chimeric promoters (e.g., CMV promoter fused to the β-actin promoter). Of course, promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the β-actin promoter, the EF1α promoter, and the retroviral long terminal repeat (LTR).

The provided vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the *E. coli* lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

Cells comprising the provided GECIs, the GECI-encoding nucleic acid sequences or vectors comprising the GECI-encoding nucleic acid sequence are provided. The cell can be, for example, a eukaryotic or prokaryotic cell. Suitable cells include, but are not limited to cells of *E. coli, Pseudomonas, Bacillus, Streptomyces*; fungi cells such as yeasts (*Saccharomyces*, and methylotrophic yeast such as *Pichia, Candida, Hansenula*, and *Torulopsis*); and animal cells, such as CHO, R1.1, B-W and LM cells, African Green Monkey kidney cells (for example, COS 1, COS 7, BSC1, BSC40, and BMT10), insect cells (for example, Sf9), human cells and plant cells. Suitable human cells include, for example, HeLa cells or human embryonic kidney (HEK) cells. Cells that can be used herein are commercially available from, for example, the American Type Culture Collection (ATCC), P.O. Box 1549, Manassas, Va. 20108. See also F. Ausubel et al., Current Protocols in Molecular Biology, John Wiley & Sons, New York, N.Y., (1998). Optionally, the GECI-encoding nucleic acid sequence is located in the genome of the cell. Optionally, the cell further comprises a G-protein coupled receptor (GPCR). Optionally, the cell further comprises a nucleic acid sequence encoding the GPCR. Optionally, the nucleic acid sequence encoding the GPCR is located on a vector or in the genome of the cell. Optionally, the cell is a Hela cell or a HEK cell. Optionally, the HEK cell is a HEK293 cell or a HEK293T cell. Optionally, the cell is a human rhabdomyosarcoma cell, for example, a RMS13 cell or a 6D9 cell. Optionally, the cell is a Chinese hamster ovary (CHO) cell, a COS-7 cell, a PC12 cell. Optionally, the cell is a primary cultured neuron, a cardiomyocte or a myocyte. Optionally, the cell is a genetically modified variant of a standard cell line expressing a target protein (e.g., a GPCR) by genomic integration or transient transfection.

Methods of making the provided cells are known and the method of transformation and choice of expression vector will depend on the host system selected. Transformation and transfection methods are described, e.g., in F. Ausubel et al., Current Protocols in Molecular Biology, John Wiley & Sons, New York, N.Y., (1998), and, as described above, expression vectors may be chosen from examples known in the art. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based deliver systems. Such methods are well known in the art and readily adaptable for use with the compositions and methods described herein.

By way of example, the provided polypeptides and/or nucleic acid molecules can be delivered via virus like particles. Virus like particles (VLPs) consist of viral protein(s) derived from the structural proteins of a virus. Methods for making and using virus like particles are described in, for example, Garcea and Gissmann, Current Opinion in Biotechnology 15:513-7 (2004). The provided polypeptides can be delivered by subviral dense bodies (DBs). DBs transport proteins into target cells by membrane fusion. Methods for making and using DBs are described in, for example, Pepperl-Klindworth et al., Gene Therapy 10:278-84 (2003). The provided polypeptides can be delivered by tegument aggregates. Methods for making and using tegument aggregates are described in International Publication No. WO 2006/110728.

Also provided are transgenic animals comprising one or more cells comprising the provided GECIs or GECI-encoding nucleic acid sequence. Optionally, the GECI comprises SEQ ID NO: 2, SEQ ID NO:6, SEQ ID NO:8, SEQ ID NO:10, SEQ ID NO:12 or SEQ ID NO:14, and sequences with identity thereto, as noted above, e.g., optionally with one or more conservative amino acid substitutions. Optionally, the GECI-encoding nucleic acid sequence comprises SEQ ID NO:1, SEQ ID NO:5, SEQ ID NO:7, SEQ ID NO:9, SEQ ID NO:11 or SEQ ID NO:13, and sequences with identity thereto, as noted above. As used herein, the term animal refers to non-human animals, including, mammals, amphibians and birds. Specifically, examples include sheep, feline, bovines, ovines, pigs, horses, rabbits, guinea pigs, mice, hamsters, rats, non-human primates, and the like. As used herein, transgenic animal refers to any animal, in which one or more of the cells of the animal contain a heterologous nucleic acid. The heterologous nucleic acid can be introduced using known transgenic techniques. The nucleic acid is introduced into the cell, directly or indirectly. For example, the nucleic acid can be introduced into a precursor of the cell or by way of deliberate genetic manipulation, such as by microinjection or by infection with a recombinant virus. The nucleic acid may be integrated within a chromosome, or it may be an extrachromosomally replicating DNA.

Methods for making transgenic animals using a variety of transgenes have been described in Wagner et al. (1981) Proc. Nat. Acad. Sci. USA, 78:5016-5020; Stewart et al. (1982) Science, 217:1046-1048; Constantini et al. (1981) Nature, 294:92-94; Lacy et al. (1983) Cell, 34:343-358; McKnight et al. (1983) Cell, 34:335-341; Brinstar et al. (1983) Nature, 306:332-336; Palmiter et al. (1982) Nature, 300:611-615; Palmiter et al. (1982) Cell, 29:701-710; and Palmiter et al. (1983) Science, 222:809-814. Such methods are also described in U.S. Pat. Nos. 6,175,057; 6,180,849; and 6,133,502.

By way of example, the transgenic animal can be created by introducing a nucleic acid into, for example, an embryonic stem cell, an unfertilized egg, a fertilized egg, a spermatozoon or a germinal cell containing a primordial germinal cell thereof, preferably in the embryogenic stage in the development of a non-human mammal (more preferably in the single-cell or fertilized cell stage and generally before the 8-cell phase). The nucleic acid can be introduced by known means, including, for example, the calcium phosphate method, the electric pulse method, the lipofection method, the agglutination method, the microinjection method, the particle gun method, the DEAE-dextran method and other such method. Optionally, the nucleic acid is introduced into a somatic cell, a living organ, a tissue cell or other cell by gene transformation methods. Cells including the nucleic acid may be fused with the above-described germinal cell by a commonly known cell fusion method to create a transgenic animal.

For embryonic stem (ES) cells, an ES cell line may be employed, or embryonic cells may be obtained freshly from a host, e.g., mouse, rat, guinea pig, and the like. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the nucleic acid. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. The chimeric animals are screened for the presence of the nucleic acid, and males and females having the modification are mated to produce homozygous progeny transgenic animals.

Kits comprising one or more containers and the provided nucleic acid sequences, polypeptides, vectors, cells or combinations thereof are also provided. For example, provided is a kit comprising (i) a nucleic acid sequence encoding a GECI, wherein the GECI comprises SEQ ID NO: 2, SEQ ID NO:6, SEQ ID NO:8, SEQ ID NO:10, SEQ ID NO:12 or SEQ ID NO:14, optionally with one or more conservative amino acid substitutions, (ii) a polypeptide comprising a GECI, wherein the GECI comprises SEQ ID NO: 2, SEQ ID NO:6, SEQ ID NO:8, SEQ ID NO:10, SEQ ID NO:12 or SEQ ID NO:14, optionally with one or more conservative amino acid substitutions, (iii) a vector comprising the GECI-encoding nucleic acid sequence, (iv) a cell comprising the GECI-encoding nucleic acid sequence, (v) a cell comprising a vector comprising the GECI-encoding nucleic acid sequence, or (vi) a cell comprising the GECI. The kit can comprise any combination of (i)-(vi). Optionally, the GECI is GCaMP3. For example, the kit can comprise the vector comprising the GECI-encoding nucleic acid sequence and a cell comprising the vector. Optionally, the cells of (iv), (v) or (vi) further comprises a GPCR or a GPCR-encoding nucleic acid sequence. Optionally, the kit further comprises reagents for using the nucleic acid sequences, polypeptides, vectors, and cells. For example, if the kit comprises cells, the kit may also comprise cell culture medium. Optionally, the kit further comprises instructions for use. Optionally, the kit further comprises a GPCR, a GPCR-encoding nucleic acid sequence.

Provided is a method of screening for G-protein coupled receptor (GPCR) agonists and antagonists. The method includes contacting an agent to be tested with a cell comprises the GPCR and a genetically encoded calcium indicator (GECI) comprising SEQ ID NO: 2, SEQ ID NO:6, SEQ ID NO:8, SEQ ID NO:10, SEQ ID NO:12 or SEQ ID NO:14, and sequences with identity thereto, as noted above, e.g., optionally with one or more conservative amino acid substitutions. The method further comprises determining the level of fluorescence. An increase in fluorescence as compared to a control indicates the agent is a GPCR agonist and a decrease in fluorescence as compared to a control indicates the agent is a GPCR antagonist. Optionally, the GECI is GCaMP3. The cell can be in vivo or in vitro. Optionally, the cell is in an animal, for example, a mouse, a worm, a rat, or a fly.

Optionally, prior to contacting an agent to be tested with the cell, the cell is transformed with a first vector comprising a nucleic acid sequence encoding the GECI. The cell can further be transformed with a nucleic acid sequence encoding the GPCR wherein the GPCR-encoding nucleic acid is present within the first vector or within a second vector. The first and second vector optionally comprises additional elements. Optionally, the cell is transformed with a second vector comprising a nucleic acid sequence encoding the GPCR. Optionally, the cell is transformed with the first vector before, after or at the same time as the second vector.

As used herein, a modulator refers to a compound which modulates a receptor, including agonists, antagonists, allosteric modulators, and the like. Typically, the modulator binds to the receptor (i.e. acts as a ligand for the GPCR), but can also act upstream or downstream of the receptor. GPCR modulators thus refer to agents that modulate (e.g., stimulate or inhibit) the activity of G-protein-coupled receptors. Inhibitors can bind reversibly, in which case they can usually be "competed off" by increasing the levels of the normal agonist, or they can bind irreversibly, in which case the inhibitory effect is observed to be non-competitive.

As used throughout, a control or control value includes the level of fluorescence in a control cell (e.g., a cell before or after the effect of a treatment or in the absence of treatment) or a control sample obtained from a subject (e.g., from the same subject before or after the effect of treatment, or from a second subject without a disorder and/or without treatment) or can comprise a known standard. The level of fluorescence is determined, for example, from a biological sample obtained from a subject in vitro or in vivo. As used herein, a change in the level of fluorescence means at least 1.5 times the magnitude of the background fluorescence level. As used throughout, higher, increases, enhances or elevates as compared to a control refer to increases above a control. As used throughout, lower or decreases as compared to a control refer to decreases below a control.

As used herein, an agent to be screened or tested includes, for example, a polypeptide, a small molecule, a nucleic acid molecule, a peptidomimetic, and combinations thereof Optionally, the agent is a polypeptide. Optionally, the polypeptide is an antibody. Optionally, the agent is a nucleic acid molecule. The nucleic acid molecule can, for example, be an inhibitory nucleic acid molecule. Inhibitory nucleic acid molecules include, for example, a triplex forming oligonucleotide, an aptamer, a ribozyme, a short interfering RNA (siRNA), or a micro-RNA (miRNA).

A 21-25 nucleotide siRNA or miRNA sequence can, for example, be produced from an expression vector by transcription of a short-hairpin RNA (shRNA) sequence, a 60-80 nucleotide precursor sequence, which is subsequently processed by the cellular RNAi machinery to produce either an siRNA or miRNA sequence. Alternatively, a 21-25-nucleotide siRNA or miRNA sequence can, for example, be synthesized chemically. Chemical synthesis of siRNA or miRNA sequences is commercially available from such corporations as Dharmacon, Inc. (Lafayette, Colo.), Qiagen (Valencia, Calif.), and Ambion (Austin, Tex.). A siRNA sequence preferably binds a unique sequence within the target mRNA with exact complementarity and results in the degradation of the target mRNA molecule. A siRNA sequence can bind anywhere within the target mRNA molecule. A miRNA sequence preferably binds a unique sequence within the target mRNA with exact or less than exact complementarity and results in the translational repression of the target mRNA molecule. A miRNA sequence can bind anywhere within the target mRNA sequence, but preferably binds within the 3' untranslated region of the target mRNA molecule. Methods of delivering siRNA or miRNA molecules are known in the art, e.g., see, Oh and Park, Adv. Drug. Deliv. Rev. 61(10):850-62 (2009); Gondi and Rao, J. Cell Physiol. 220(2):285-91; and Whitehead et al., Nat. Rev. Drug. Discov. 8(2):129-38 (2009).

As used herein, an inhibitory nucleic acid sequence can be an antisense nucleic acid sequence. Antisense nucleic acid sequences can, for example, be transcribed from an expression vector to produce an RNA which is complementary to at least a unique portion of the target mRNA and/or the endogenous gene which encodes the target. Hybridization of an antisense nucleic acid under specific cellular conditions results in inhibition of the target protein expression by inhibiting transcription and/or translation.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

The term antibody is used herein in a broad sense and includes both polyclonal and monoclonal antibodies. The term can also refer to a human antibody and/or a humanized antibody.

As used throughout, a G-protein coupled receptor (GPCR) refers to any member of a superfamily of receptors that mediates signal transduction by coupling with a G protein and is associated with a change in Ca2+ signaling and/or concentration. This class of GPCRs work through the Gq type of G proteins, which activate a phospholipase C (PLC) pathway, resulting in the hydrolysis of phosphoinositides to generate two classes of different second messengers, namely, diacylglycerol and inositol phosphates. Diacylglycerol activates certain protein kinase Cs (PKCs) and certain inositol phosphates stimulate the mobilization of calcium from intracellular stores.

Exemplary GPCRs include, but are not limited to alpha-1 adrenegic receptors ($\alpha$1-AR), urotensin (UT) receptors, 5-HT2 and 5-HT6 serotonin receptors, hypocretic (orexin) receptors, histamine H1 receptors, bradykinin B1 and B2 receptors, bombesin BB2 receptors, P2Y purinergic receptors, acetycholine receptors (e.g., M1, M3 and M5), mGluR5 glutamate receptors, vasopressin V2 and V1 receptors, angiotensin AGTR1 receptors, cholecystokinin CCKAR and CCKBR receptors, endothelin ENDRA receptors, ghrelin GHSR1a receptors, melatonin MTNR1A receptors, neurotensin NTSR1 receptors, platelet-activating factor PTAFR receptors, and prolactin releasing peptide receptor PRLHR receptors.

It is also possible to study $G_s$- and $G_i$-coupled receptors by co-expressing a cAMP-gated Ca2+ channel, which has been described in Airan et al., Nature (2009) 458(7241):1025-1029. This is carried out by taking advantage of the promiscuous G-protein G15/16 (Zhang et al., "Evaluation of FLIPR calcium assay kit-a new no-wash fluorescence calcium indicator reagent" J Biomol Screen, 8(5):571-577 (2003)), or by using chimeric G-proteins (Hsu and Luo, "Molecular dissection of G protein preference using Gs{alpha} chimeras reveals novel ligand signaling of GPCRs" Am J Physiol Endocrinol Metab 293(4):E1021-E1029 (2007)). Such receptors include, but are not limited to, G-coupled 5-HT6 and 5-HT7 serotonin receptors, Gi-coupled GABA-B, histamine H3, and mGluR2/4 glutamate receptors.

Methods of monitoring neural activity are provided. The methods include the step of determining the level of fluorescence in a neuronal cell comprising a GECI. Optionally, the GECI comprises SEQ ID NO: 2, SEQ ID NO:6, SEQ ID NO:8, SEQ ID NO:10, SEQ ID NO:12 or SEQ ID NO:14, and sequences with identity thereto, as noted above, e.g., optionally with one or more conservative amino acid substitutions. The cell can be in vivo or in vitro. Optionally, the cell is in an animal, for example, a mouse, a worm, a rat, or a fly. Optionally, prior to the determining step the cell is transformed with a nucleic acid sequence encoding the GECI. Optionally, the nucleic acid sequence is located on a vector.

Also provided is a method of monitoring neural activity of a non-human subject. The method includes the steps of obtaining from the non-human subject a biological sample comprising one or more neuronal cells, wherein the neuronal cells comprise a GECI comprising SEQ ID NO: 2, SEQ ID NO:6, SEQ ID NO:8, SEQ ID NO:10, SEQ ID NO:12 or SEQ ID NO:14, and sequences with identity thereto, as noted above, e.g., optionally with one or more conservative amino acid substitutions, and determining the level of fluorescence in the one or more neuronal cells comprising the GECI. Optionally, the subject is a mouse, a worm or a fly. Neural activity is used herein as an example, but other cells types can be used. For example, GCaMP3 can be used to detect the activity of muscle cells or cardiomyocytes.

As used herein a biological sample which is subjected to testing is a sample derived from and includes, but is not limited to, a biological fluid, preferably a bodily fluid. The biological fluid may be a cell culture medium or supernatant of cultured cells. For example, the sample can be a brain tissue sample or primary cultured neurons. Optionally, the biological sample comprises muscle cells, cardiomyoctes or myocytes.

As used throughout, subject can be a vertebrate, more specifically a mammal (e.g. a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g., an infectious disease). The term patient or subject includes human and veterinary subjects.

Optional or optionally means that the subsequently described event or circumstance can or cannot occur, and that the description includes instances where the event or circumstance occurs and instances where it does not.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

In some embodiments, one or more of the compositions disclosed herein can be used in the manufacture of a diagnostic marker, a medicament for treatment of disease, or a kit.

Publications cited herein and the material for which they are cited are hereby specifically incorporated by reference in their entireties.

EXAMPLES

Example 1

Improved GCaMP Calcium Indicators

Materials and Methods

Construct and Virus Production.

GCaMPs were sub-cloned into pRSETa for expression and purification in E. coli. GCaMPs were sub-cloned into pCMV for HEK293 cell assays and cultured brain slice experiments. GCaMP variants, TN-XXL and D3cpV were sub-cloned into the pCAGGS vector with a CAG promoter (CMV-enhancer, β-actin promoter, and regulatory element from the woodchuck hepatitis virus4 (WPRE)) for in utero electroporation (Saito and Nakatsuji, Dev. Biol. 240:237-246 (2001)). pCAG-mCherry was co-transfected with GCaMPs for cultured hippocampal slices and in utero electroporation for better control of expression level. To make transgenic worms and flies, GCaMPs were sub-cloned into pSM under control of the str-2 promoter and pMUH, respectively. pMUH-GCaMPs were incorporated into an attP40 integrase site on the second Drosophila chromosome (Genetic Services, Inc., Cambridge, Mass.). For in vivo calcium imaging in mice, GCaMP2 and GCaMP3 were expressed using an adeno-associated virus 2/1 (AAV2/1) driving the sensor under control of the pan-neuronal human synapsin-1 promoter 8. GCaMP2 and GCaMP3 were sub-cloned into the rAAV-hSYN expression vector, and live virus was produced (University of Pennsylvania Vector Core Services, Philadelphia, Pa.). All constructs were verified by sequencing.

Bacterial Protein Expression, Purification, and Testing.

GCaMPs in pRSETa were transformed into chemically competent BL21(DE3)-pLysS, and purified via the N-terminal His tag. Protein concentration was determined by intrinsic tryptophan fluorescence. Calcium clamping was performed at pH 7.2 with 10 mM blends of K2H2EGTA and Ca2EGTA from the Calcium Calibration Kit #1 (Invitrogen, Carlsbad, Calif.). Free [Ca2+] levels were calculated using the MAXCHELATOR program (Stanford, Calif.). Fluorescence spectra were recorded on a Safire2 fluorescence plate reader (Tecan, Switzerland). The dynamic range here is calculated as Fmax/Fmin. Fmax is the fluorescence intensity at saturating $[Ca^{2+}]$ and Fmin is the fluorescence intensity at zero $[Ca^{2+}]$.

HEK293 Cell-Based Screen.

GCaMPs in pCMV were transfected into HEK293 cells using Lipofectamine 2000 (Invitrogen, Carlsbad, Calif.), and imaging experiments were performed 48 hours post transfection. 293 cells transfected with GCaMPs in 96-well plate were imaged on an FDSS plate reader (Hamamatsu, Japan). Acetylcholine (Ach) was automatically added 10 seconds after read initiation. Brightness was quantified using VOLOCITY® 5.0 (Improvision).

Calcium Imaging in Worms.

Calcium imaging of GCaMP-expressing worms was performed as described previously (Chalasani et al., Nature 450: 63-70 (2007)). A total of 12 animals for each genotype were studied in a custom-designed microfluidic device, and the fluorescence response to odour stimulation was averaged. For odour presentation, each animal was first starved for 20 min. Odours were presented, at t=10 seconds in a 60 second recording, and removed five minutes later, at t=10 seconds in a second 60 second recording.

Mice Brain Slice Preparation.

Hippocampal slice cultures were prepared using standard methods (Stoppini et al., J. Neurosci. Methods 37:173-182 (1991); Mao et al., PLoS ONE 3:e1796 (2008)). For biolistic gene transfer, 10 μg of DNA were used per full tube. Imaging experiments were performed 24-48 hours after biolistic transfection. For acute slice experiments, GECIs were introduced into E-16 mouse embryos by in utero electroporation, and acute slices were prepared at P14-17 as described before (Mao et al., PLoS ONE 3:e1796 (2008)).

Fly Stocks, Preparation and Odour Delivery.

Flies were reared on standard cornmeal agar medium. The Gal4/UAS system (Brand et al., Methods Cell Biol. 44:635-654 (1994)) was used to direct the expression of the calcium sensors to projection neurons (PNs). GH146-Gal4 flies were obtained from Stanford University, Stanford, Calif. UAS-GCaMP1.6 flies were obtained from MPI, Martinsried, Germany. All experimental animals were adult females, 3-5 days after eclosion. Adult flies were dissected using previously described methods (Mao et al., PLoS ONE 3:e1796 (2008)). Flies were anaesthetized in a vial on ice just until movement stopped (~15 second) and then gently inserted into a hole in a piece of aluminum foil. Small drops of wax (55° C.) were used to suspend the fly in the hole, with the edge of foil defining a horizontal plane around the head and thorax, from the first antennal segment anteriorly to the scutellum posteriorly. The dorsal side of the foil was bathed in saline, while the ventral side (including antennae and maxillary palps) remained dry and accessible to odours. A window was cut in the dorsal head cuticle between the eyes, extending from the ocelli to the first antennal segment. Fat and air sacs dorsal and anterior to the brain were removed, but the perineural sheath was left intact. The proboscis was affixed with a small drop of wax to a strand of human hair to limit brain movement. Spontaneous leg movements were typically observed in this preparation for the duration of the recording (1.5-3 hr). The saline composition used in all experiments was (in mM): 103 NaCl, 3 KCl, 5 N-tris(hydroxymethyl)methyl-2-aminoethane-sulfonic acid, 10 trehalose, 10 glucose, 2 sucrose, 26 $NaHCO_3$, 1 $NaH_2PO_4$, 1.5 $CaCl_2$, and 4 $MgCl_2$, adjusted to 275 mOsm, pH 7.3 when bubbled with 95% $O_2$/5% $CO_2$.

Odours (cis-3-hexen-1-ol (cis), and isoamyl acetate (ia)) were delivered using a custom-made odour-delivery system and a Teflon nozzle (entry diameter ⅛") directed towards the antennae. Odours were delivered in a constant stream of air (1 l/min) at final concentrations of ca. 15%. Odour delivery times were measured using a mini-PID (Aurora Scientific Inc., Ontario, Canada). Odours were presented for either 3 seconds or 5 seconds. All comparisons of sensor performance were made using experiments with identical odour presentation times. The results reported are based on data obtained from 3 GCaMP1.6-expressing flies (4 ALs) and 4 GCaMP3-expressing flies (4 ALs).

Calcium Imaging in Fly.

A two-photon laser-scanning microscope (Prairie Technologies, Middleton, Wis.) using an Olympus 0.8 NA LUMP1FI40XW/IR2 objective was used for imaging. A mode-locked Ti:Sapphire Chameleon Ultra II laser (Coherent, Santa Clara, Calif.) tuned to 920 nm was used as excitation source. Fluorescence was collected using photomultiplier tubes (Hamamatsu, Hamamatsu City, Japan) after bandpass filtering using a 525/70 nm emission filter. Images were acquired using PrairieView software in framescan mode (4-16 Hz) for a single plane of one antennal lobe.

Electrophysiology and Calcium Imaging in Brain Slice.

Recordings were made from CA1 cells in hippocampal slice culture, and cortical layer 2/3 pyramidal cells (S1) in acute brain slices at room temperature (22-24° C.). Patch pipettes were pulled from borosilicate glass (standard wall with filament) and had 4-6 MΩ resistance when filled with internal solution (128 K-methylsulfate or K-gluconate, 10 HEPES, 10 Na-phosphocreatine, 4 $MgCl_2$, 4 $Na_2ATP$, 0.4 $Na_2GTP$, 3 ascorbic acid (pH 7.25, 290 mOsm), in mM). Slice recording and simultaneous line scan imaging were performed as before (Mao et al., PLoS ONE 3:31796 (2008)). During recording, slices were bathed in ACSF (127 NaCl, 25 $NaHCO_3$, 1.25 $NaH_2PO_4$, 25 glucose, 2.5 KCl, 2 $CaCl_2$, 1 $MgCl_2$, in mM) bubbled with carbogen. Cells were selected for data analysis if they had nuclear exclusion of GECI fluorescence, input resistances of at least 100 MΩ, and resting potentials ≤−50 mV in cultured slice, or ≤−65 mV in acute slice. For experiments with evoked-action potential stimuli, 10 µM (R)-CPP (Tocris, Ellisville, Mo.) and 10 µM NBQX (Sigma, St. Louis, Mo.) were added to the bath to block glutamate receptors. Action potentials were triggered at 83 Hz by current injection (1-4 nA, 2 ms) through the patch pipette.

Imaging was performed in line-scan mode (500 Hz) across the apical dendrite, 20-50 µm from the base (FIG. 2A). The Ti:Sapphire laser (Mai Tai, Spectro-Physics, CA) was tuned to 910 nm for GCaMPs imaging and 860 nm to excite FRET indicators. For GCaMPs co-expressed with the fluorescent protein mCherry, fluorescence was separated into green and red channels with a 565 nm dichroic, and BG22 (green channel) and HQ620/90 (red channel) emission filters. For the FRET-based GECIs, fluorescence was separated with a 505 nm dichroic, HQ480/80 (cyan channel) and HQ535/50 (yellow channel) emission filters. The PMT dark current was subtracted from all traces. In slice culture recordings, mean baseline fluorescence (F0) was calculated from the filter raw trace (20 Hz) prior to the action potential stimuli, as in (Mao et al., PLoS ONE 3:e1746 (2008)). Peak fluorescence was determined by averaging 30 ms of the raw fluorescence time series about the peak of the trace linearly filtered at 20 Hz. For acute slices, response baseline was defined as the mean of the 250 ms window immediately prior to stimulation. Peak response was calculated as the maximum value of the filtered trace (100 ms moving window) within 500 ms of stimulation cessation. This method gave ~3% ΔF/F for 0 AP traces. Noise was calculated on a per cell level, as the mean standard deviation of stimulation-free, one second, bleach-corrected trace segments. For display, example traces were filtered with a Savitzky-Golay filter (2nd order, 50 ms span). Action potential detection was quantified both by a double blind psychometric test and by algorithmic template-matching. In the psychometric test, eight volunteers were shown a response template and asked if it was present in randomly ordered, sequentially presented traces. False positive rate was determined by the response to 0 AP traces. The algorithmic method computed the maximum cross-correlation between a template and the fluorescence trace lagged 200 ms about the stimulus onset. Detection success was defined as a cross-correlation value greater than 95% of baseline traces. The baseline trace set consisted of all recorded 0 AP traces plus those traces reversed and/or inverted. The template was the first 1.5 seconds of the mean 3AP response (GCaMP3) or the mean 5AP response (D3cpV, TN-XXL). Rise T1/2 of hippocampal neurons was measured as the time between the onset of current injection and the half peak response. Decay T1/2 was measured as the time of half decay of a single exponential fit of the recovery from peak response to baseline. All analysis was performed with MATLAB (Mathworks, Natick, Mass.).

In Vivo Calcium Imaging and Electrophysiology in Mice.

rAAVs (AAV2/1; synapsin-1 promoter) were injected into the primary somatosensory cortex (S1) of 2-3 week old C57B1/6Crl wild-type mice. Two weeks after injection, mice were anaesthetized with 2% isoflurane, and a 1.5 mm circular craniotomy was performed over the injection site as previously described (Huber et al., Nature 451:61-64 (2008)). Cells were recorded with a patch pipette containing (in mM): 10.0 KCl, 140 K-gluconate, 10.0 HEPES, 2.0 $MgCl_2$, 2.0 $CaCl_2$, 0.05 Alexa 594, pH 7.25, 290 mOsm. For recording and stimulation a MultiClamp 700B amplifier (Molecular Devices, Sunnyvale, Calif.) was used. In whole cell mode, action potentials were evoked by 2-5 ms long current injections; in cell attached mode currents up to 100 nA were necessary. The Ti:Sapphire laser (Mai Tai, Spectro-Physics, CA) was tuned to 910 nm for GCaMP3 imaging. Fluorescence images were simultaneously acquired using a custom-built, two-photon laser-scanning microscope equipped with a 40×, 0.8 NA objective (Olympus, Tokyo, Japan). Frame scans were acquired at 15 Hz (256×32 pixels) for a period of 3 seconds.

For imaging awake, head-fixed running mice, virus injection and surgery were identical to the anesthetized condition, except that the injection and craniotomy were performed over the primary whisker and forelimb motor area (M1). In addition, local (Marcaine) and general (Buprenorphine, 0.1 mg/kg IP, and Ketoprofen, 5 mg/kg SC) anesthetics were administered. After full recovery on a heating pad, the animals were head restrained but allowed to run freely on a linear treadmill. Action potentials were recorded using a loose-seal cell attached configuration with patch pipettes filled with buffer (in mM: 125 NaCl, 2.5 KCl, 25.0 glucose, 10.0 HEPES, 2.0 $CaCl_2$, 2.0 $MgSO_4$, 0.05 Alexa 594; pH 7.4, 285 mOsm), and signals were amplified using a MultiClamp 700B (Molecular Devices, Sunnyvale, Calif.). To confirm the identity of recorded neurons, each recording was terminated by breaking into the cell and filling with red pipette solution. During the imaging sessions, the animals were kept alert by sporadic acoustic stimuli (clapping) or by presenting a pole or mild air puffs to the whisker field. Images were acquired at frame rates of 4-8 Hz at a resolution of 256×512 pixels using a 16×, 0.8 NA water immersion objective (Nikon USA, Lewisville, Tex.). All images acquired while awake were corrected for movement artifacts using the ImageJ plug-in TurboReg program. ΔF/F was calculated by subtracting the baseline fluorescence level (F0, 35th percentile of total fluorescence) from the actual fluorescence level and normalized to F0.

Chronic Calcium Imaging in Behaving Mice.

For chronic imaging, surgery and craniotomy were carried out as described above, but the GCaMP3-AAV was injected into the cortex directly prior to sealing the imaging window with dental acrylic. Chronic imaging was performed on C57BL/6Crl wild-type (infected with AAV2/1-hsyn1-GCaMP2) and PV-CRE mice (infected with CRE-dependent AAV2/1-hsyn1-GCaMP2) over periods from 10 to 120 days post infection. To keep the animals alert and active during imaging sessions, mice were water restricted and trained to lick for water rewards upon whisker deflection. Decay times (τ ½, time at half maximum) were calculated by fitting to a single exponential. All data analysis was performed with MATLAB (Mathworks, Natick, Mass.).

Imaging Data Analysis.

For in vivo imaging in worms, fluorescence signals in the AWC cell body were analyzed using automated tracking software and MATLAB scripts as described (Chalasani et al., Nature 450:63-70 (2007)).

In flies, fluorescence time series were then obtained by averaging across the spatial extent of the glomerulus in the frame. In all cases fluorescence changes were calculated relative to baseline fluorescence levels as determined by averaging over 2 seconds just before odour presentation.

For imaging data analysis in mice in vivo, the cell body without nucleus was used as ROI for fluorescent transient analysis. Recordings with spontaneous spikes were excluded. ΔF/F was the peak fluorescence increase within 500 ms of stimulus onset divided by the mean of the three frames preceding stimulus onset. Action potential detection was quantified using cross-correlation template-matching with the first six frames of the mean response to 3 APs as a template and the second half of 1 AP and 2 AP traces (1.5-2.83 s post stimulus, 100 total traces) as the baseline. In awake behaving mice, the ΔF/F of spontaneous fluorescence transients was calculated as the peak fluorescence increase divided by the mean of the 5th-10th percentile of fluorescent intensities. All data analysis was performed with MATLAB (MathWorks, Natick, Mass.).

Characterizing Intrinsic and Circuit Properties of GCaMP3 Expressing Neurons.

L2/3 progenitor cells were transfected via in utero electroporation in C57BL/6Crl E16 time pregnant mice with a plasmid expressing CRE recombinase under the CAGS promoter as previously described (Saito and Nakatsuji, Dev. Biol. 240:237-246 (2001); Petreanu et al., Nat. Neurosci. 10:663-668 (2007)). At postnatal day P14, a CRE-dependent AAV virus expressing GCaMP3 under the human synapsin-1 promoter was injected into the neocortex. This combinatorial method allowed labeling of a sparse subpopulation of L2/3 pyramidal neurons with GCaMP3. Cells were recorded at a depth of 50 to 95 µm Immediately after breaking in, cells were depolarized by injection of graded current pulses. Fourteen (14) to twenty-one (21) days after the viral infection (P28 to P34), animals were anesthetized with an intraperitoneal injection of a ketamine/xylazine mixture (0.13 mg ketamine/ 0.01 mg xylazine/g body weight) and perfused through the heart with a small volume of ice cold ACSF containing (in mM): 130 NaCl, 25 NaHCO$_3$, 25 D-glucose, 2.5 KCl, 1.0 MgCl$_2$, 2.0 CaCl$_2$, and 1.25 NaH$_2$PO$_4$, aerated with 95% O$_2$/5% CO$_2$. The brain was removed and place in an ice-cold cutting solution containing (in mM): 110 choline chloride, 25 NaHCO$_3$, 25 D-glucose, 11.6 sodium ascorbate, 7.0 MgCl$_2$, 3.1 sodium pyruvate, 2.5 KCl, 1.25 NaH$_2$PO$_4$, and 0.5 CaCl$_2$. 400 µm thick coronal slices of the barrel cortex were cut with a vibrating slicer (Microm, Walldorf, Germany) and incubated in oxygenated ACSF for 45 min at 37° C. before the recordings. Pairs of L2/3 pyramidal neurons (within <100 µm; one GCaMP3+, the other GCaMP3−) were recorded sequentially. The synaptic input impinging onto GCaMP3+ and GCaMP3− neurons was compared by measuring the total excitatory input onto both recorded cells using laser-scanning photo-stimulation by glutamate uncaging. Briefly, stimulation was with an ultraviolet laser (DPSS Lasers, Santa Clara, Calif.) on a grid (16×16, spacing 75 µm). This area included the entire thickness of the cortical grey matter and adjacent barrel columns. MNI-glutamate was uncaged for 1 ms with 20 mW of laser power at the specimen plane. It was verified that, under experimental conditions, these stimulation parameters elicited action potentials only when the laser beam was close to the soma of the neurons. Only excitatory inputs were mapped as cells were held at −70 mV, close to the reversal for fast inhibition. Responses were analyzed within 100 ms after the UV stimulus. Direct and synaptic responses were separated according to their different onset time. Responses with an onset time below 7 ms were categorized as direct (i.e. purely postsynaptic) and later responses as synaptic. Synaptic input maps were calculated as the mean current in a response window from 7 to 75 ms.

Signal-to-Noise (SNR) Calculation.

SNR was calculated as the ratio of ΔF/F or ΔR/R to standard deviation of the filtered trace (100 ms moving window), 250 ms before the stimulus up to stimulus onset.

Statistical Analysis.

P-values were computed by a Mann-Whitney algorithm in MATLAB. All value ranges are given as mean±standard deviation (SD), unless otherwise noted.

Results

Structure-Guided Engineering of GCaMP3

Figure 12A:
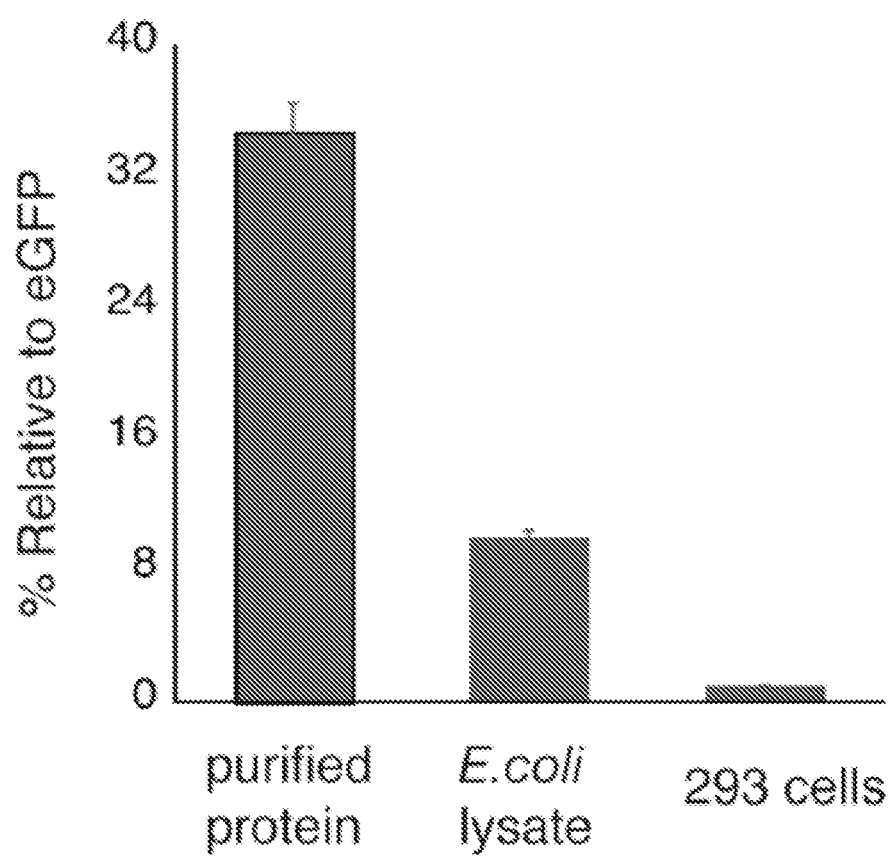
FIGS. 12A-12C show improved protein stability of GCaMP2.1.
Figure 12B:
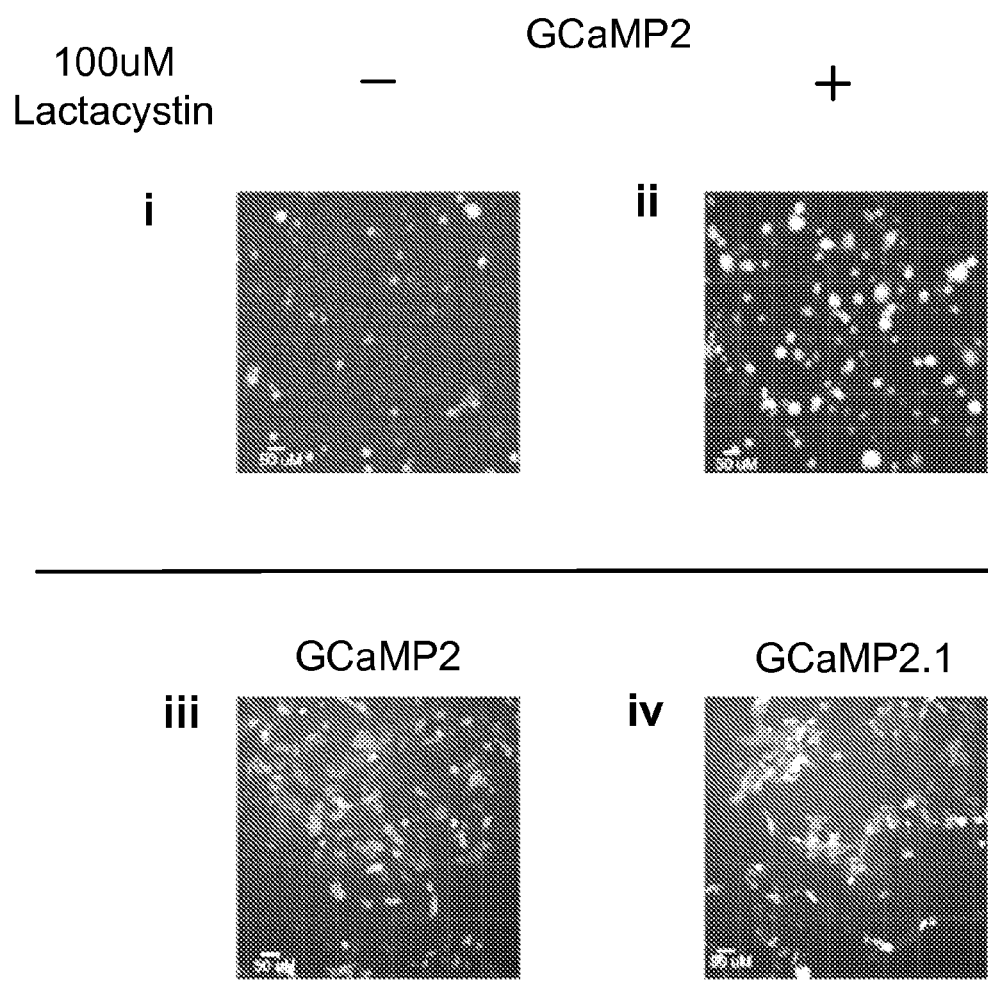
Figure 12C:
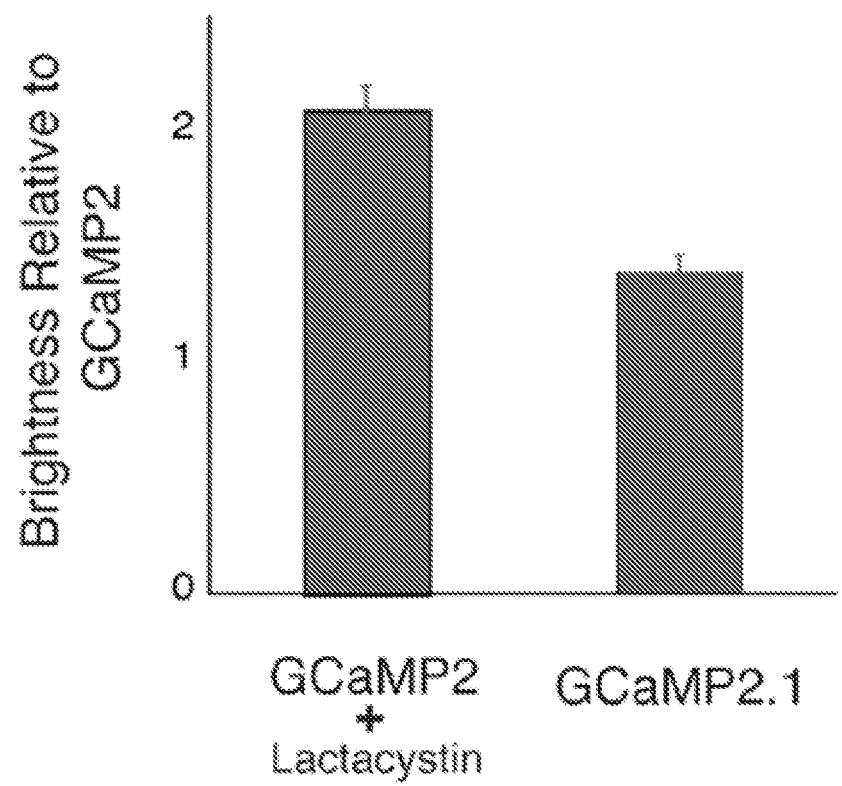

In HEK293 cells the fluorescence of GCaMP2 is one hundred fold lower than EGFP (FIG. 12A). Addition of a proteasome inhibitor (10 µM lactacystin) increased the baseline fluorescence of HEK293 cells expressing GCaMP2 (FIGS. 12B and 12C). It was determined that an N-terminal arginine, found immediately after the initiator methionine of GCaMP2, might destabilize the protein. Indeed, HEK293 cells transfected with a mutant lacking the arginine, named GCaMP2.1, showed 40% higher baseline fluorescence than those transfected with GCaMP2 (FIGS. 12B and 12C). The nucleic acid and amino acid sequences of GCaMP2.1 are provided as SEQ ID NO:5 and SEQ ID NO:6, respectively.

Figure 13B:
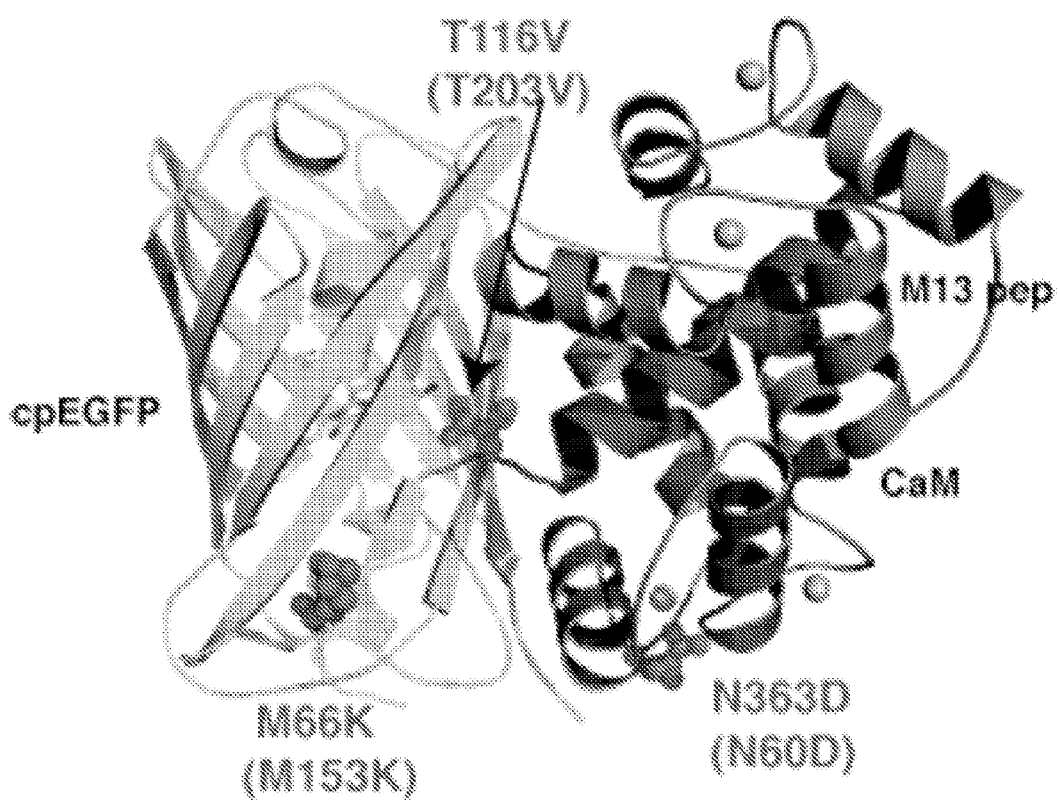
FIG. 13B is a schematic of the structural model of GCaMP3 based on the structure of GCaMP2.
Figure 14:
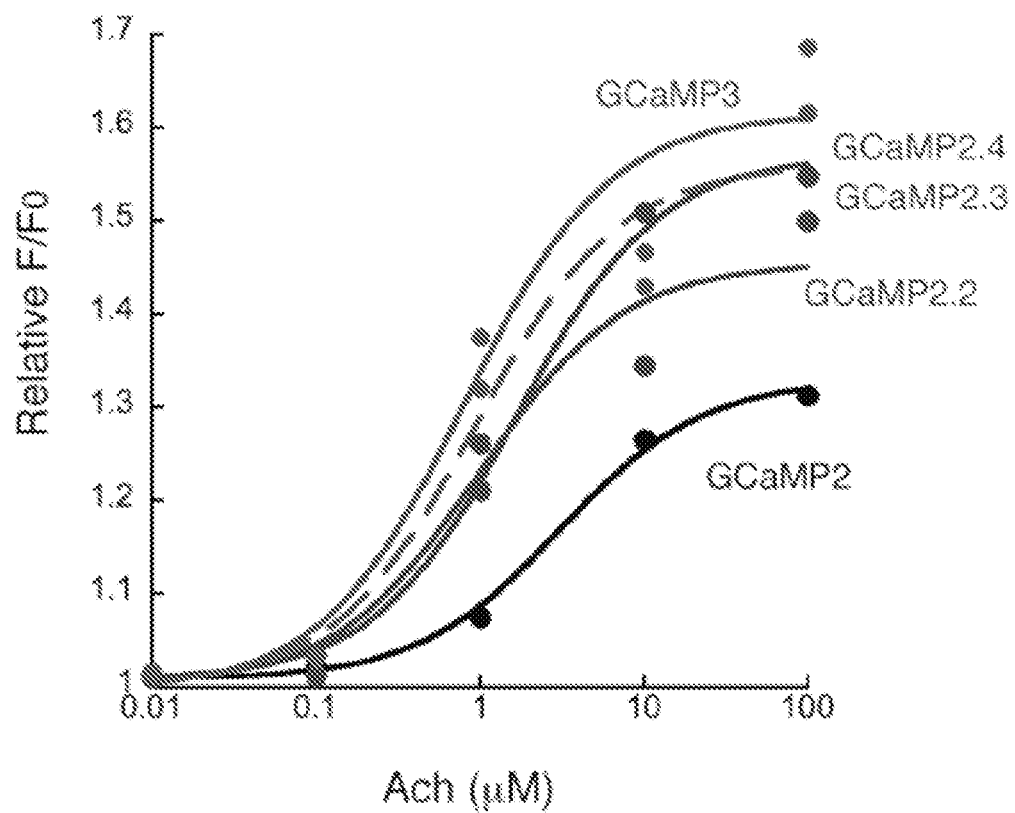
FIG. 14 is a graph showing screening resulted in several mutants with improved baseline brightness and signal change in HEK293 cells.

Small libraries of GCaMP2.1 variants were created via site-directed mutagenesis at many sites, both near the EGFP chromophore and at "superfolder GFP" positions (FIGS. 13A and 13B). A medium-throughput mammalian cell-based assay in HEK293 cells was designed. Calcium transients were induced by activating endogenous muscarinic receptors with acetylcholine. Acetylcholine titrations of GCaMP-transfected HEK293 cells revealed two point mutants with increased dynamic range and baseline fluorescence (T116V; GFP T203V and M66K; GFP M153K). One single (T116V) mutant and a double mutant (T116V and M66K) were named GCaMP2.2a and GCaMP2.3, respectively (FIG. 1A and FIG. 14). The nucleic acid and amino acid sequences of GCaMP2.2a are provided as SEQ ID NO:7 and SEQ ID NO:8, respectively. The nucleic acid and amino acid sequences of GCaMP2.3 are provided as SEQ ID NO:11 and SEQ ID NO:12, respectively. An additional variant named GCaMP2.2b is also provided, the nucleic acid and amino acid sequences of which are provided as SEQ ID NO:9 and SEQ ID NO:10, respectively.

To increase GCaMP's affinity for calcium to allow better detection of the small and rapid calcium increases associated with individual APs, mutations were analyzed in the EF-hands of GCaMP2 and in the interface between the M13 peptide and the calmodulin (CaM) domain of GCaMP2 (FIGS. 13A and 13B). The amino acid substitution N363D (CaM N60D) to both GCaMP2.2a and GCaMP2.3 increased the fluorescence change for small calcium transients, with little effect on baseline fluorescence (FIG. 1A and FIG. 14). GCaMP2.2a-N363D and GCaMP2.3-N363D were named GCaMP2.4 and GCaMP3, respectively (FIGS. 1A and 1B). The nucleic acid and amino acid sequences of GCaMP2.4 are provided as SEQ ID NO:13 and SEQ ID NO:14, respectively. GCaMP3 showed the largest signal change in the acetylcholine assay (FIGS. 1A and 1B) and was further characterized.

Figure 1D:
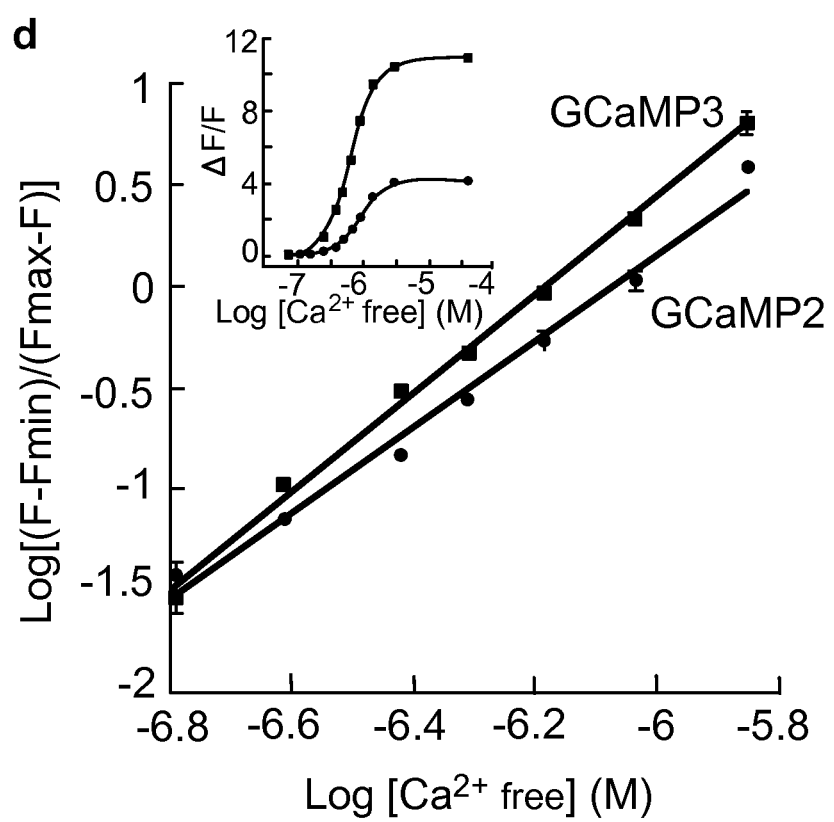

The fluorescence spectra of purified GCaMP3 were similar to those of GCaMP2, with a slight red-shifting of the excitation maximum (FIG. 1C). GCaMP3 protein assayed in 3-(N-morpholino)propanesulfonic acid (MOPS) buffer had a dynamic range (Fmax/Fmin) of ~12, 3-fold larger than GCaMP2 (FIG. 1D—inset). This results from a 2-fold decrease of calcium-free fluorescence and a 1.5-fold increase of calcium-saturated fluorescence (FIG. 1C—inset). The affinity of GCaMP3 for Ca2+ was ~1.3-fold higher than GCaMP2 ($660\pm19$ nM versus $840\pm25$ nM, (p=0.0017, paired t-test)) (FIG. 1D).

Figure 1E:
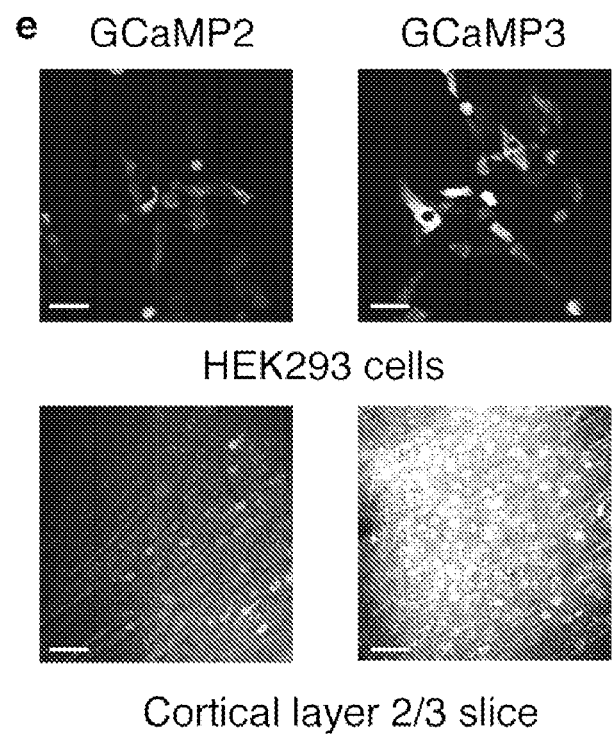
Figure 1E:
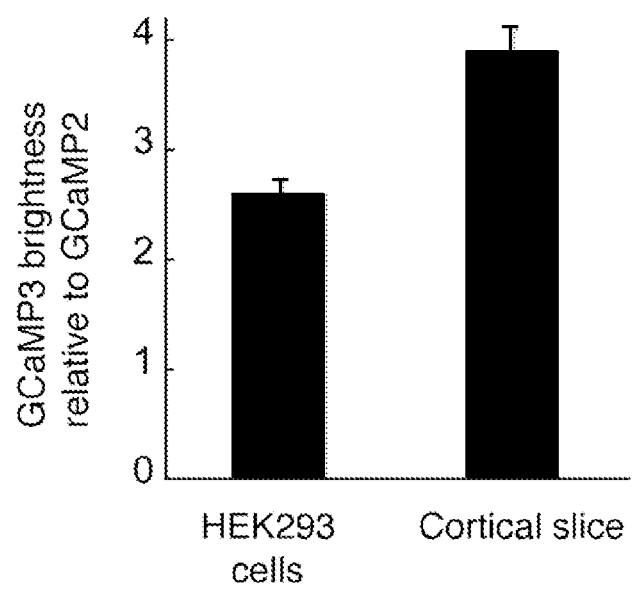

In HEK293 cells GCaMP3 showed ~2.6-fold higher baseline fluorescence than GCaMP2 (FIG. 1E—top). When expressed via viral gene transduction in cortical layer 2/3 neurons, baseline fluorescence was ~3.9-fold higher than GCaMP2 (FIG. 1E—bottom). Given the lower fluorescence of purified GCaMP3, the increase in baseline fluorescence is likely caused by increased protein expression and stability at 37° C.

Characterization of GCaMP3 in Brain Slice

Figure 2C:
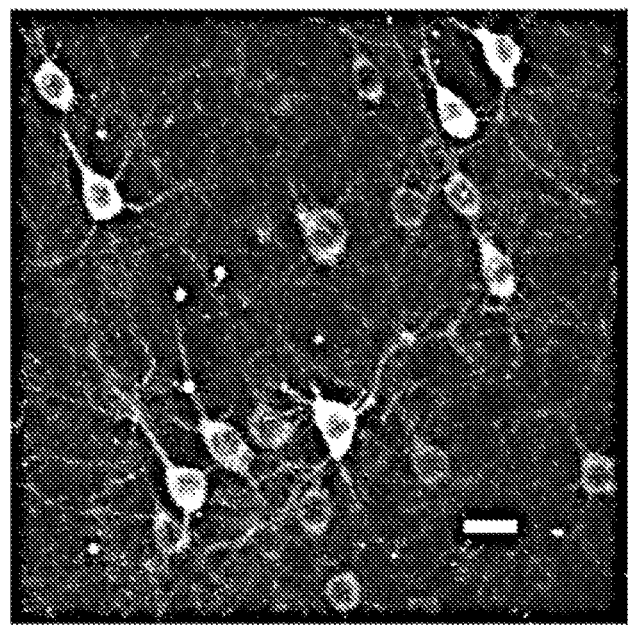
Figure 15:
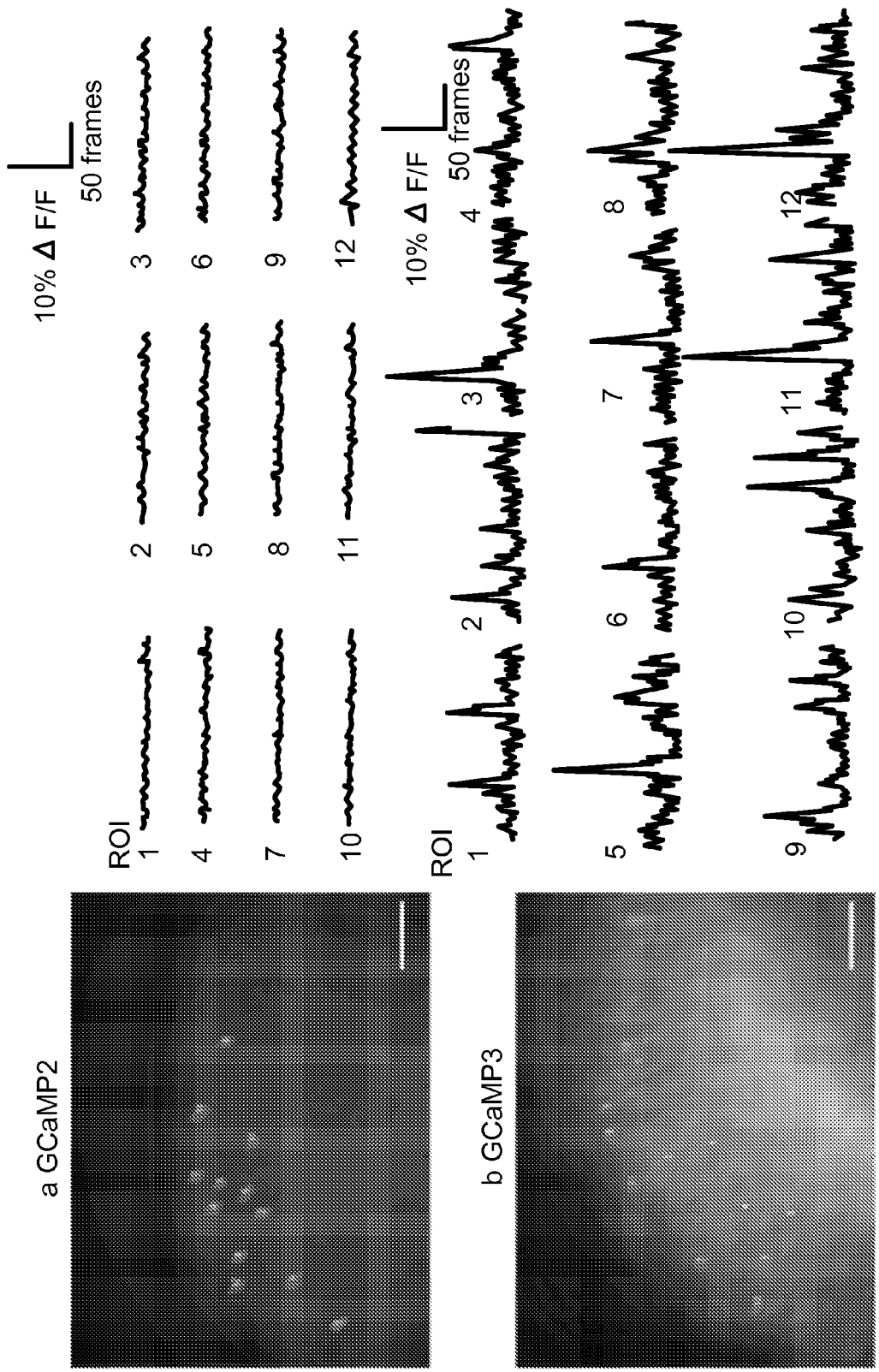
FIG. 15 shows images of spontaneous activity of neurons in hippocampal slice using GCaMP2 and GCaMP3. Scale bar, 200 μm.
Figure 16A:
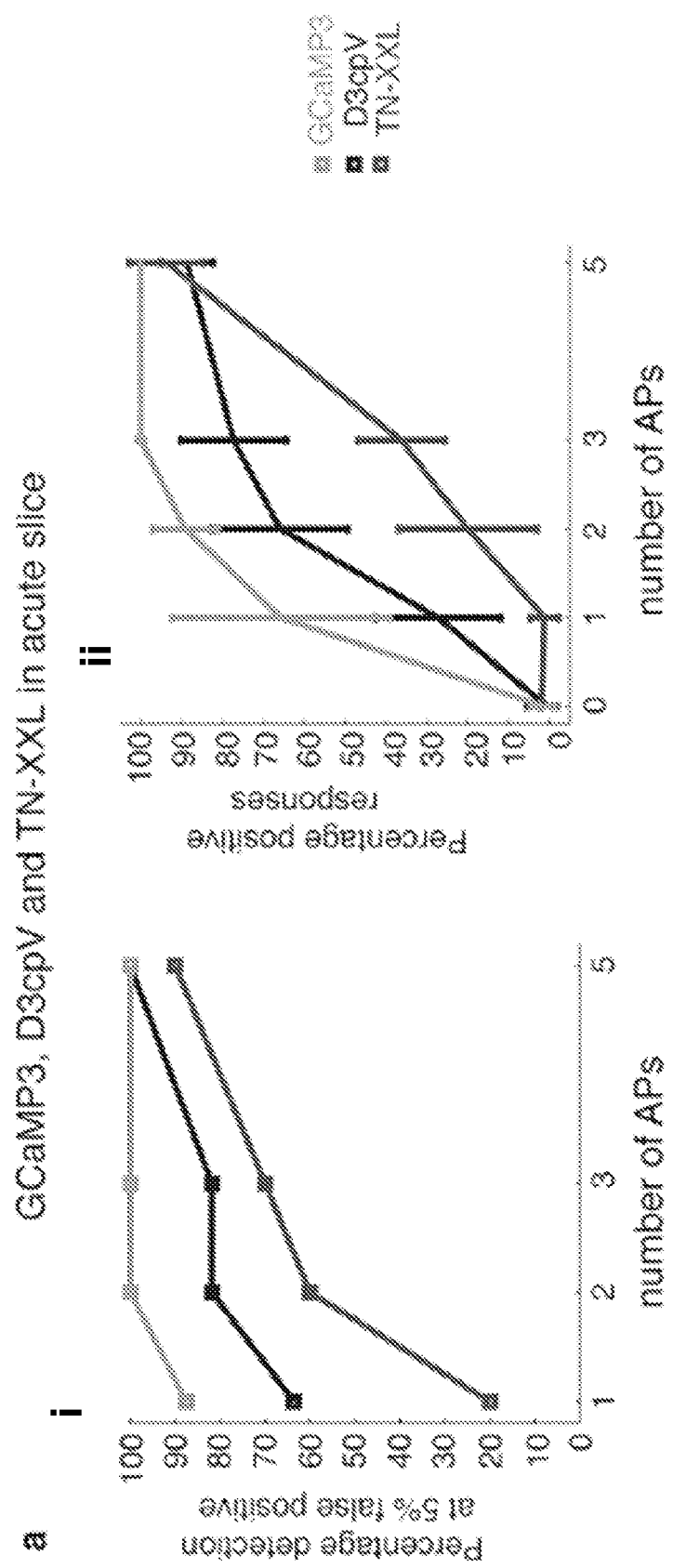
FIGS. 16A and 16B show action potential (AC) detection probability.
Figure 16B:
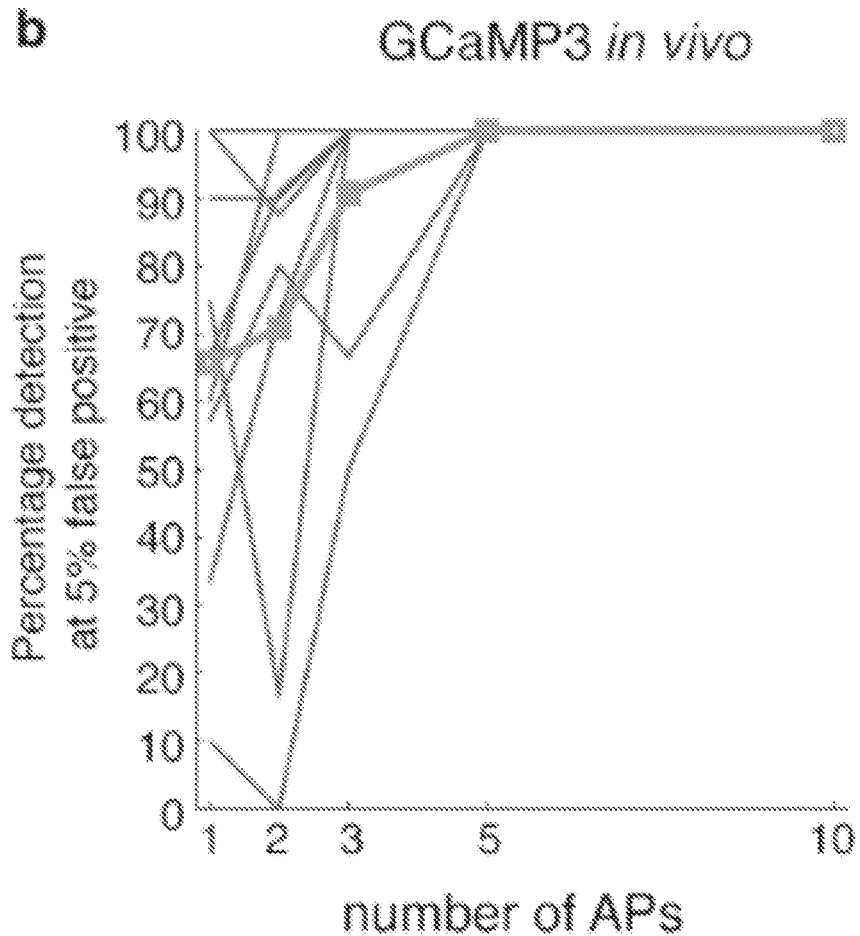

The AP-triggered fluorescence responses were measured of GCaMP3 in pyramidal neurons in cultured brain slices (FIGS. 2A and 2B) and acute neocortical brain slices at room temperature (FIGS. 2C and 2D). In cultured slice, GCaMP3 was delivered by biolistic transfection. Increases in GCaMP3 fluorescence intensity ($\Delta F/F=46\pm4.2\%$, n=9 cells) at the base of the apical dendrite were detected reliably in response to single APs in all cells (100% single-trial detection). The average $\Delta F/F$ of GCaMP3 (n=9 cells) was $185\pm13\%$, $250\pm27\%$, $320\pm35\%$, $480\pm50\%$, $600\pm100\%$, and $620\pm130\%$ for 2, 3, 5, 10, 20 and 40 AP, respectively (FIGS. 2B and 2E). The signal-to-noise ratio (SNR) of GCaMP3 was $16.3\pm10.9$, $167.1\pm65.1$ and $371.4\pm102.8$ for 1 AP, 5 AP and 40 AP, respectively (FIG. 2F). The fluorescence increase and single AP detection efficiency are significantly improved over GCaMP2 (1 AP $\Delta F/F=17\pm10\%$; 38% single-trial detection). The kinetics of GCaMP3 in cultured hippocampal slice are similar to those of GCaMP2 (GCaMP3: rise T1/2=$83\pm2$ ms; decay T1/2=$610\pm32$ ms; GCaMP2: rise T1/2=$95\pm15$ ms; decay T1/2=$480\pm130$ ms24; all measurements for 10 AP stimulus). The improved properties of GCaMP3 allow imaging spontaneous population activities in cultured hippocampal slice, as opposed to GCaMP2 (FIG. 15).

Figures 2G, 2H:
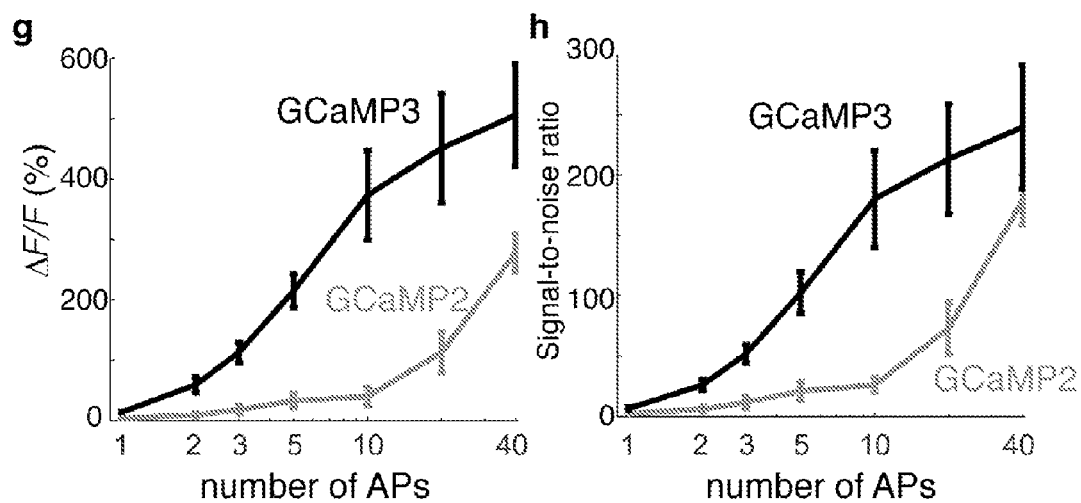

Next, the performance of GCaMP3 in layer 2/3 (L2/3) somatosensory cortical pyramidal neurons was tested following long-term expression driven by the CAG promoter via in utero electroporation (FIG. 2C). The average $\Delta F/F$ of GCaMP3 at the base of the apical dendrite was $14\pm2.7\%$ (n=9 cells) for single action potentials and $505\pm220\%$ for 40 APs (FIGS. 2D and 2G). Compared to GCaMP2 (n=8 cells), the $\Delta F/F$ and SNR of GCaMP3 were 2-5 fold larger (FIGS. 2G and 2H). Individual action potentials in single trials could be resolved at rates up to 6 Hz. The threshold for 100% spike detection in acute brain slices was 2 APs, with a 1 AP detection rate of ~90%, slightly inferior to the performance in cultured brain slices.

Comparison of GCaMP3 and FRET-based GECIs

Figure 3A:
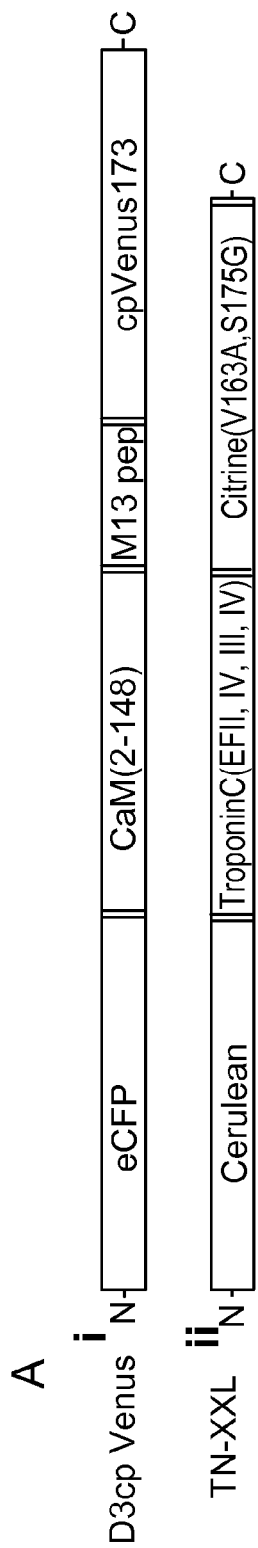
FIGS. 3A-3H show the comparison of GECI responses in pyramidal cell principal dendrites in acute cortical slices to back-propagating action potentials.
Figure 3B:
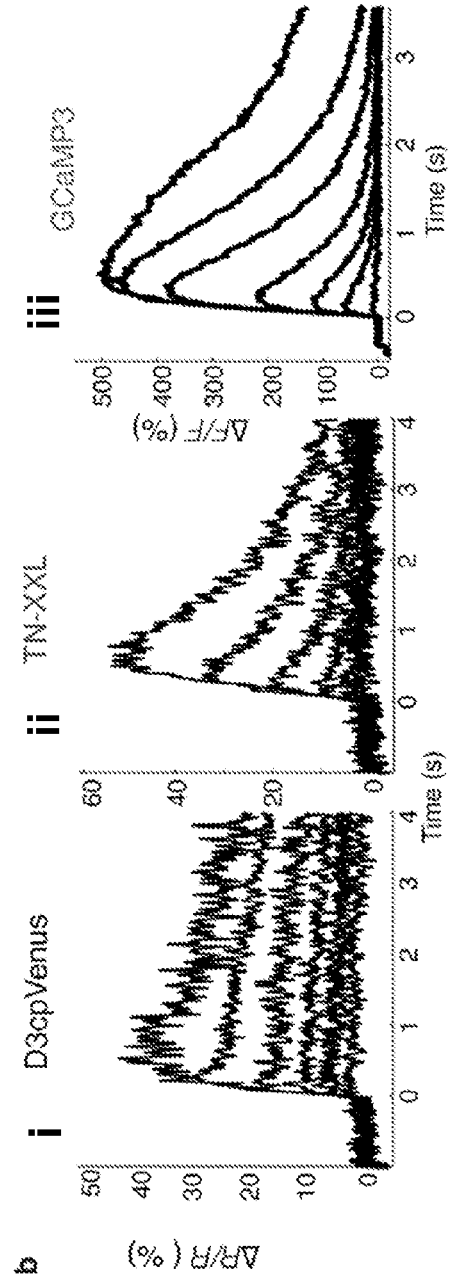
Figure 3C:
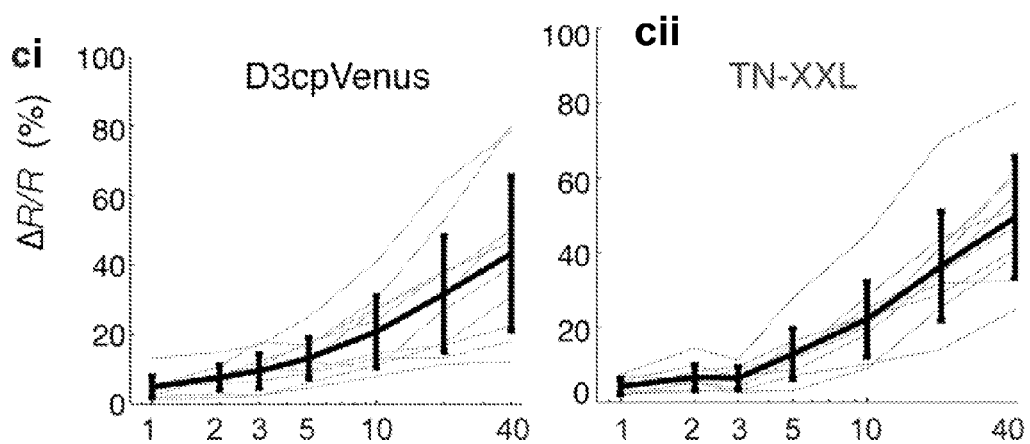
Figure 3D:
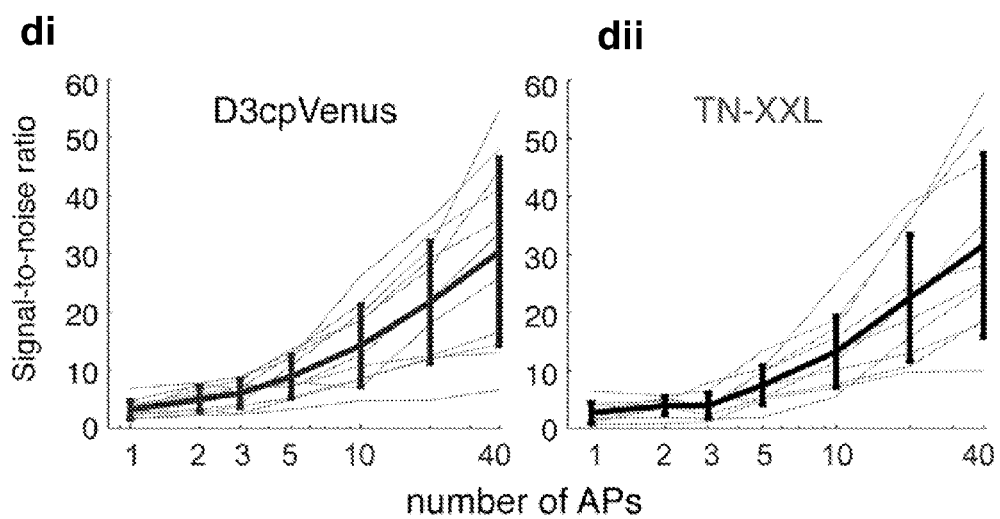
Figure 3E:
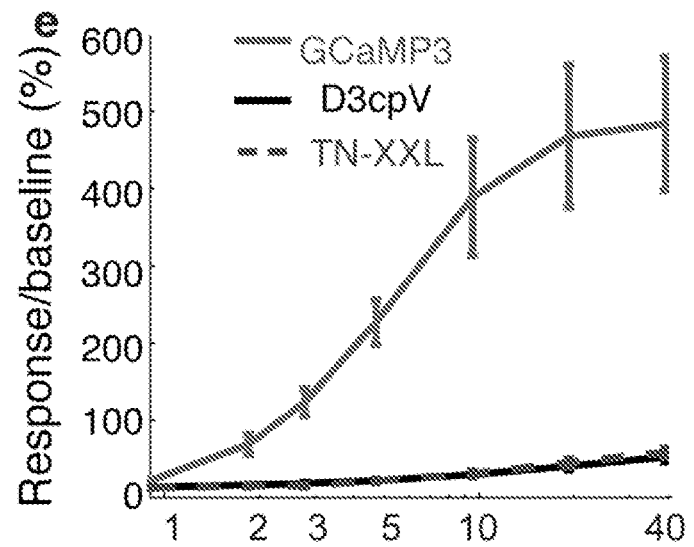
Figure 3F:
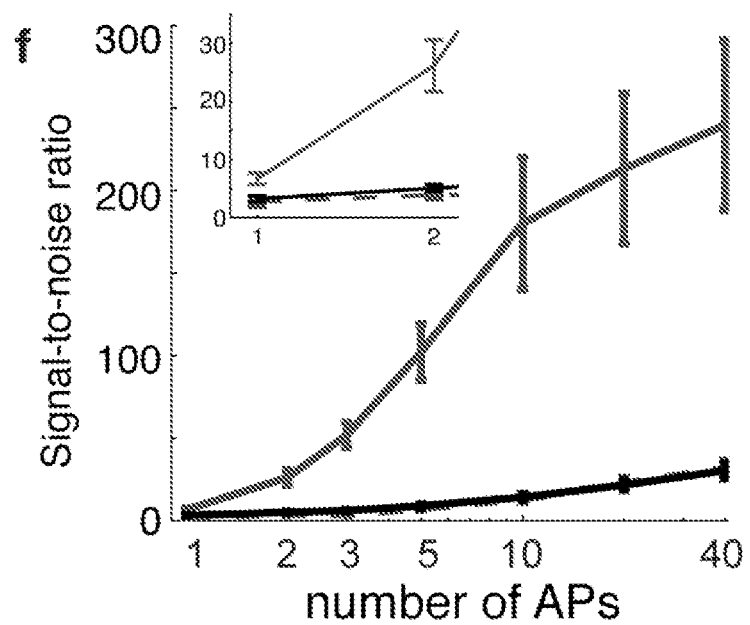
Figure 3G:
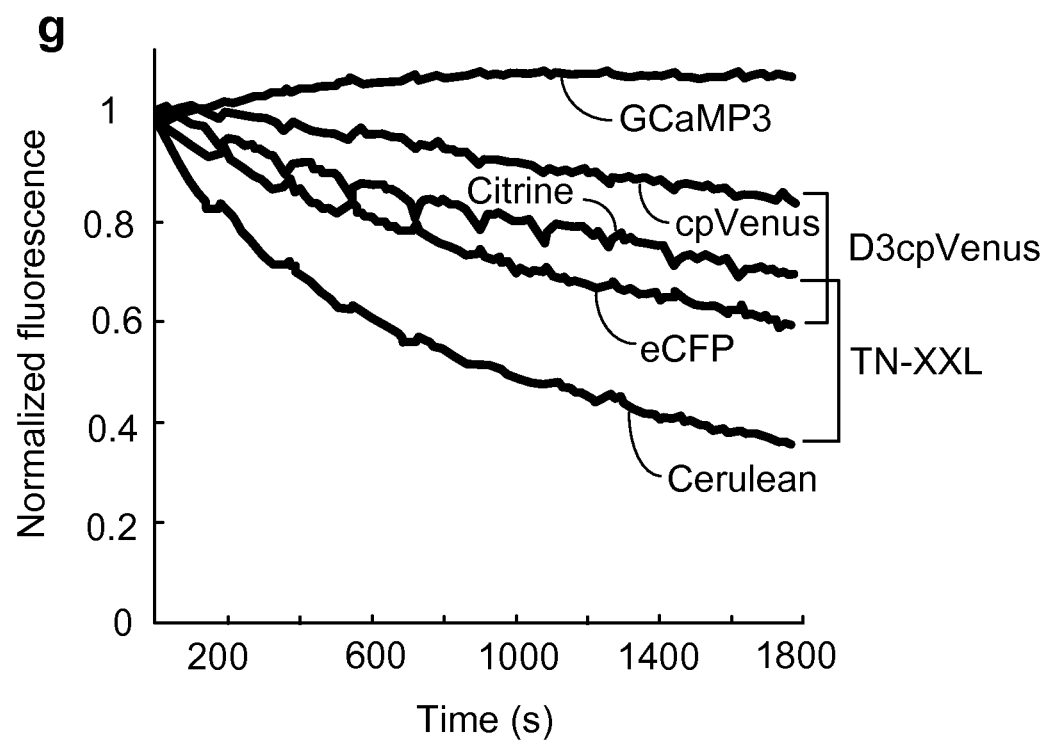
Figure 3H:
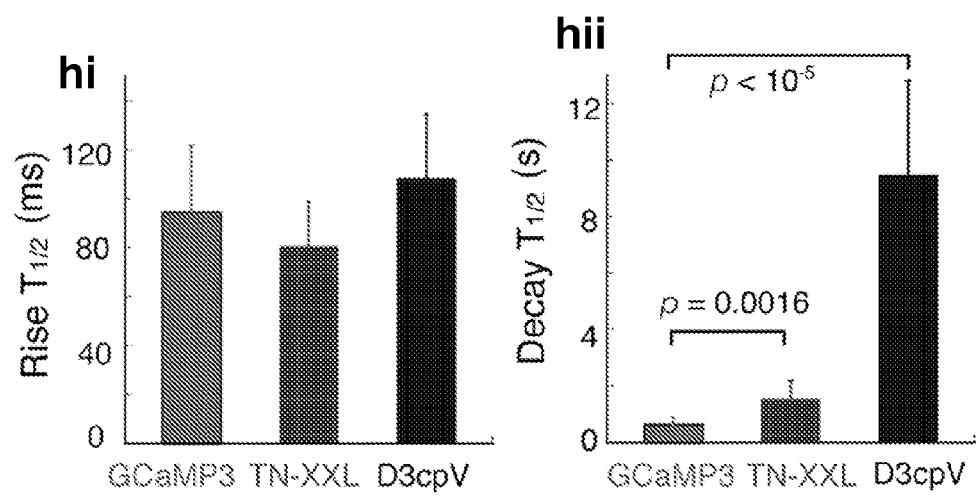

The performance of D3cpV and TN-XXL (FIG. 3A) to GCaMP3 under identical experimental conditions was compared. At baseline calcium levels, the FRET indicators (based on intact fluorescent proteins) were brighter than GCaMP3. However, the smaller fluorescence changes produced by the FRET indicators (FIGS. 3B and 3C and FIGS. 16A and 16B) resulted in lower SNR compared to GCaMP3 (FIGS. 3D-3F). Furthermore, GCaMP3 was more photostable than the FRET indicators. Following 10 cycles of 150 seconds of frame-scan illumination of the soma and proximal dendrite (10 mW at the sample), interspersed by 30 seconds of darkness, GCaMP3 fluorescence remained unchanged (109% of starting fluorescence), whereas TN-XXL (36% CFP; 70% YFP) and D3cpV (59% CFP; 84% YFP) showed reduced fluorescence (FIG. 3G). The mean fluorescence rise times were similar: $95\pm27$ ms, $80\pm18$ ms, and $108\pm26$ ms for GCaMP3, TN-XXL and D3cpV (FIG. 3H—left). The fluorescence decay time of GCaMP3 ($650\pm230$ ms, n=7 cells), was significantly shorter than for the FRET indicators (TN-XXL, $1550\pm640$ ms, n=10 cells (p=0.0016, paired t-test); D3cpV, $9500\pm3400$ ms, n=10 cells (p=1.7e-05, paired t-test)) (FIG. 3H—right).

In terms of absolute response and SNR, GCaMP3 performed better than both FRET indicators over the entire stimulus range, particularly from 2-20 APs (FIG. 3F and Table 2).

GCaMP3 also showed greater photostability and faster kinetics (FIGS. 3G and 3H). These factors translate into improved detection and measurement of physiologically relevant calcium signals.

Imaging Sensory-Evoked Ca2+ Transients in Worms

Figure 4A:
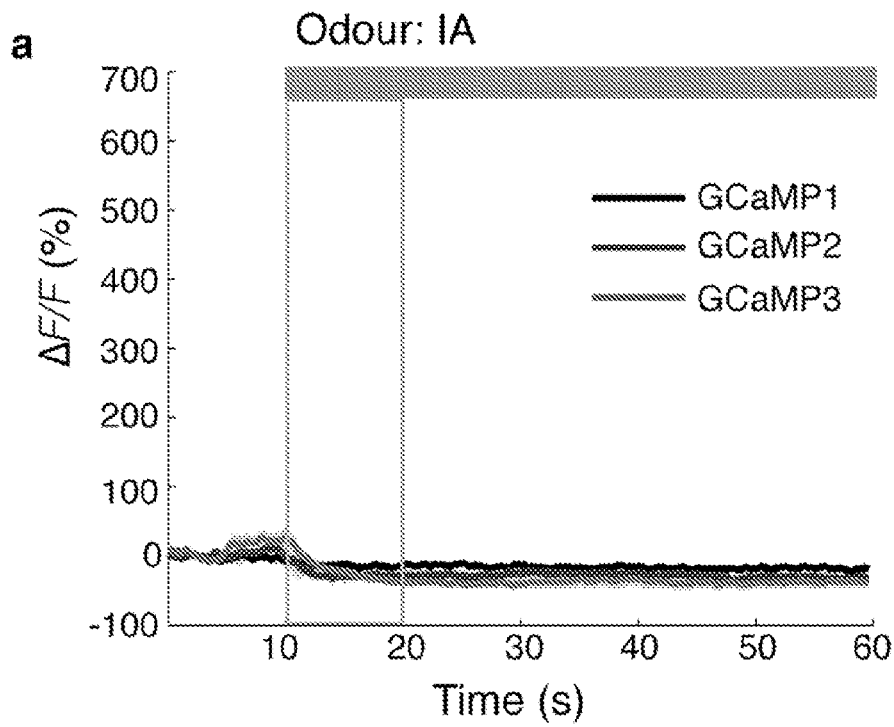
FIGS. 4A-4D show in vivo imaging of sensory-evoked $Ca^{2+}$ transients with GCaMPs in *C. elegans*. Odour-evoked responses of GCaMP1, GCaMP2 and GCaMP3 in *C. elegans* olfactory neurons. Transgenic worm lines expressing GCaMPs were imaged following an odour addition-removal sequence.
Figure 4B:
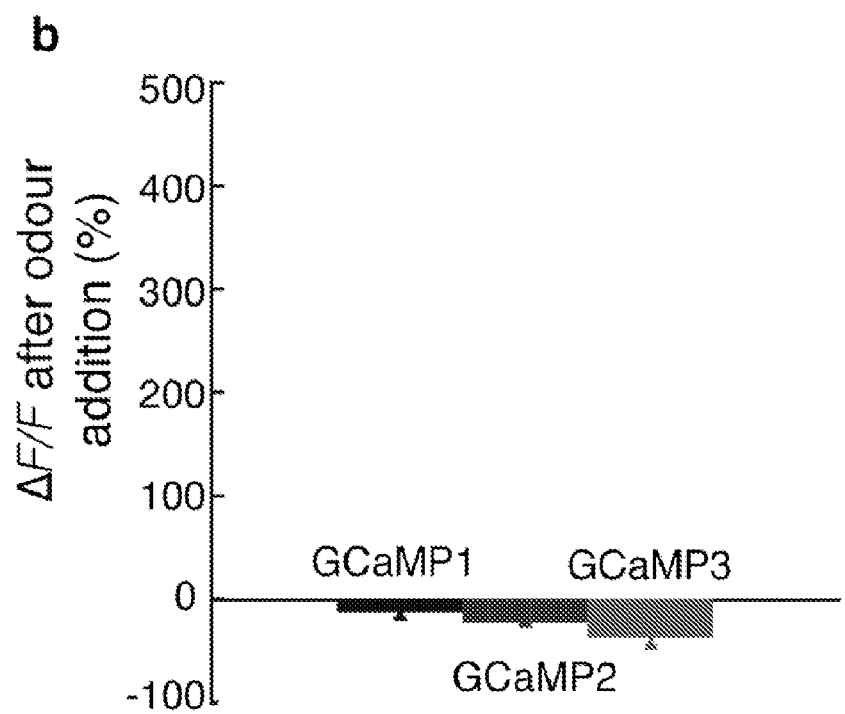
Figure 4C:
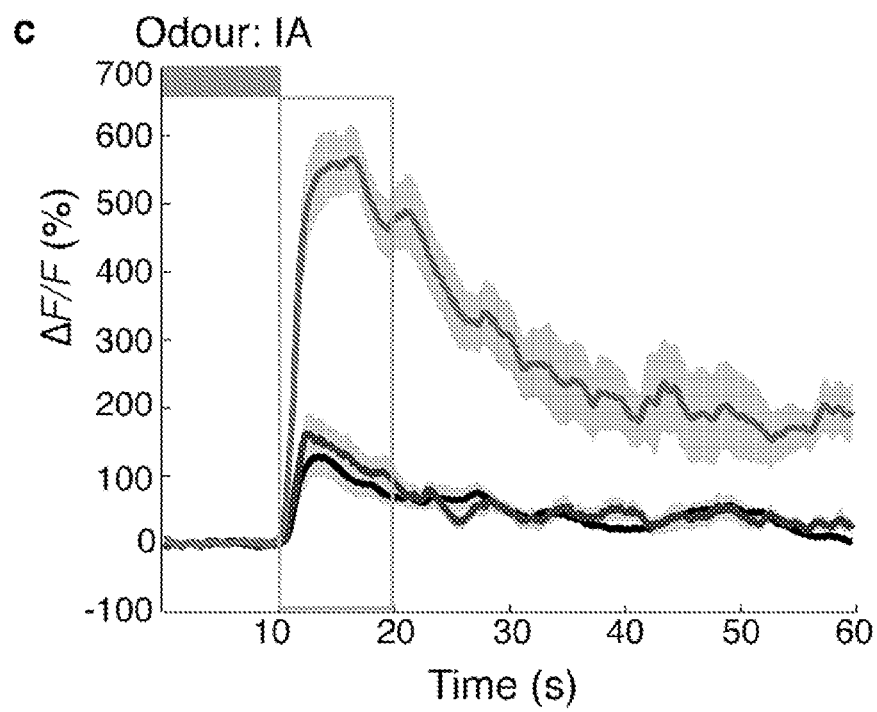
Figure 4D:
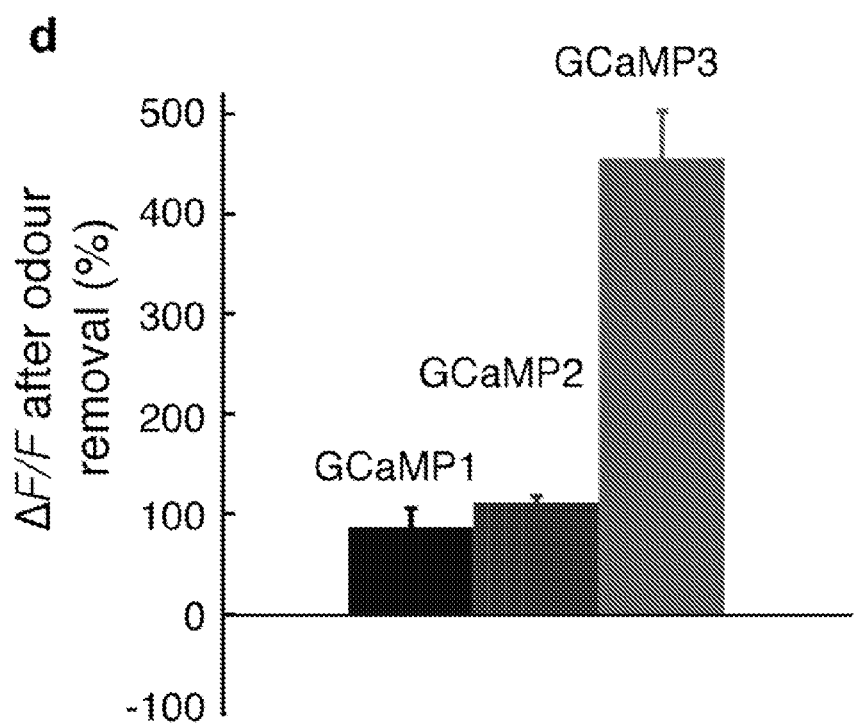
Figure 17:
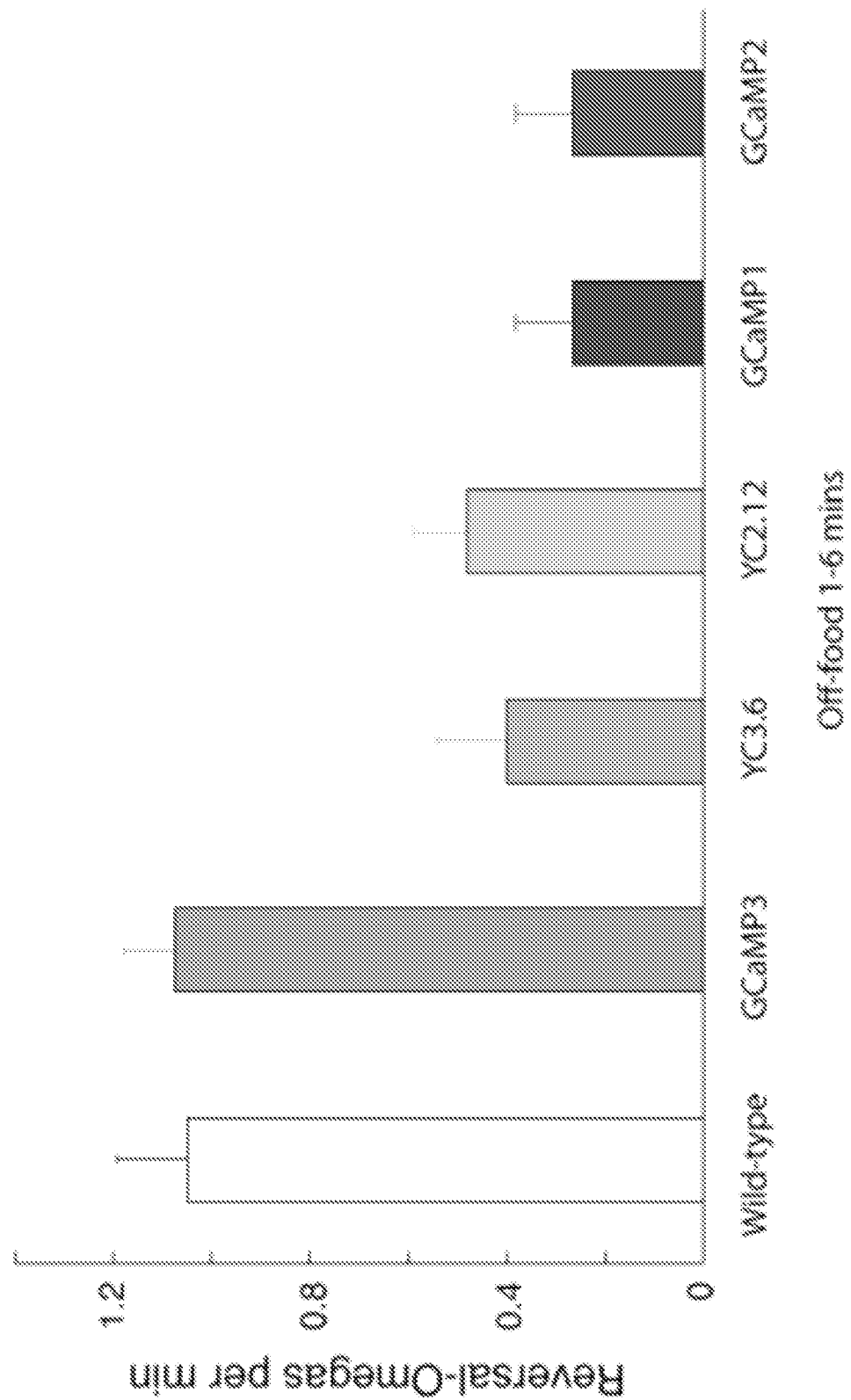
FIG. 17 is a graph showing C. elegans expressing GCaMP3 in AWC neurons showed similar local search turning behavior as wild-type animals. Decreased turning was observed in animals expressing YC3.6, YC2.12, GCaMP1 and GCaMP2 in AWC neurons. In C. elegans, local search turning behavior is triggered by AWC olfactory neurons, ASK gustatory neurons and AIB interneurons after they are removed from food. Here, animals of wild-type strain or AWC:GCaMP3 were first observed in food plates and then transferred to a food-free plate. Animals were scored at 1-6 minutes off food. Reversal-omega, paired reversal-omega turning sequences. Error bars indicate standard deviation of the mean.

To compare the performance of GCaMP3 with previous GCaMPs in response to sensory stimulation-evoked activity in sensory neurons, stable worm lines were created expressing GCaMP1, GCaMP2 and GCaMP3 in one of the two AWC neurons ($AWC^{ON}$). Expression of GCaMP1 and GCaMP2 in AWC neurons caused behavioral perturbations in some of transgenic lines, reflected by decreased local search turning. In contrast, GCaMP3-expressing worms showed no detectable cytotoxicity or behavioral perturbation (FIG. 17). Individual worms were imaged following an odour addition-removal sequence. Presentation of isoamyl alcohol inhibited $AWC^{ON}$, causing a decrease in fluorescence for all three GCaMP indicators (FIGS. 4A and 4B). The fluorescence change was larger for the two newer GCaMPs relative to GCaMP1 ($-13\pm6\%$ for GCaMP1, $-27\pm8\%$ for GCaMP2, $-38\pm8\%$ for GCaMP3). Subsequent removal of the attractive odour resulted in an average of $455\pm48\%$ fluorescence increase in $AWC^{ON}$ neurons expressing GCaMP3, a ~4-5-fold improvement over GCaMP2 ($113\pm25\%$ $\Delta F/F$) and GCaMP1 ($88\pm19\%$ $\Delta F/F$) (FIGS. 4C and 4D). Variation in sensory expression levels due to the mosaic nature of transgenesis precluded quantitative comparison of indicator baseline brightness.

Imaging Sensory-Evoked Ca2+ Transients in Flies

Figure 5A:
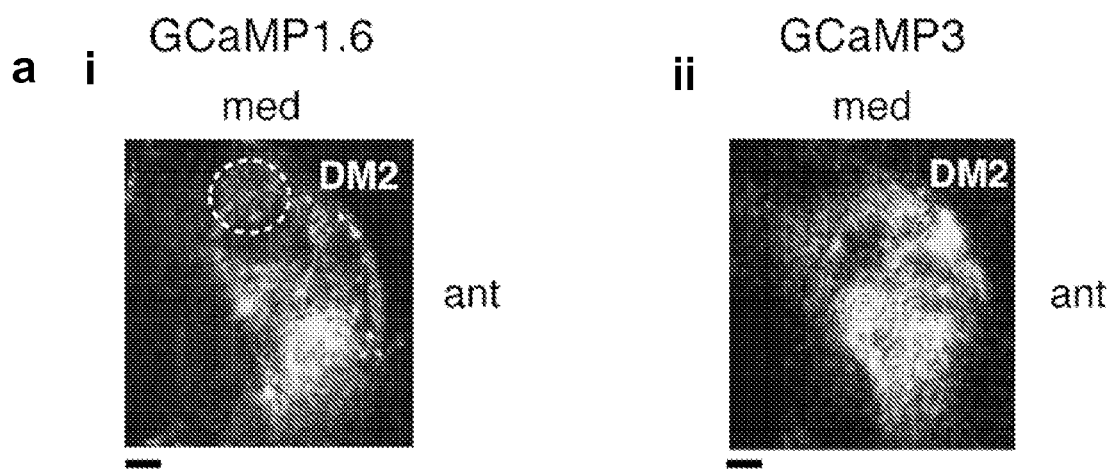
FIGS. 5A-5C show in vivo images of sensory-evoked $Ca^{2+}$ transients with GCaMPs in *Drosophila* antennal lobe (AL) projection neurons of odour-evoked responses of GCaMP1.6 and GCaMP3.
Figure 5B:
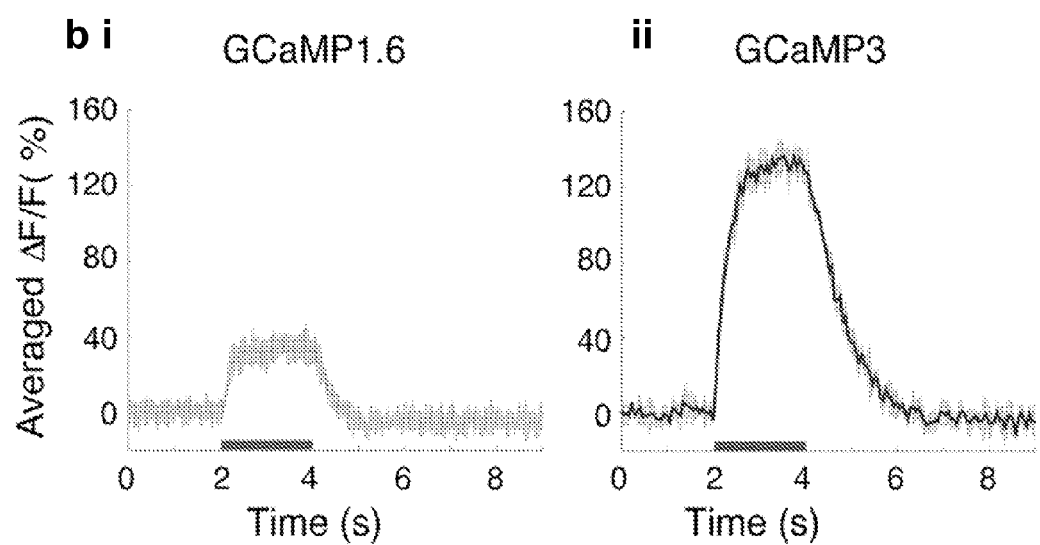
Figure 5C:
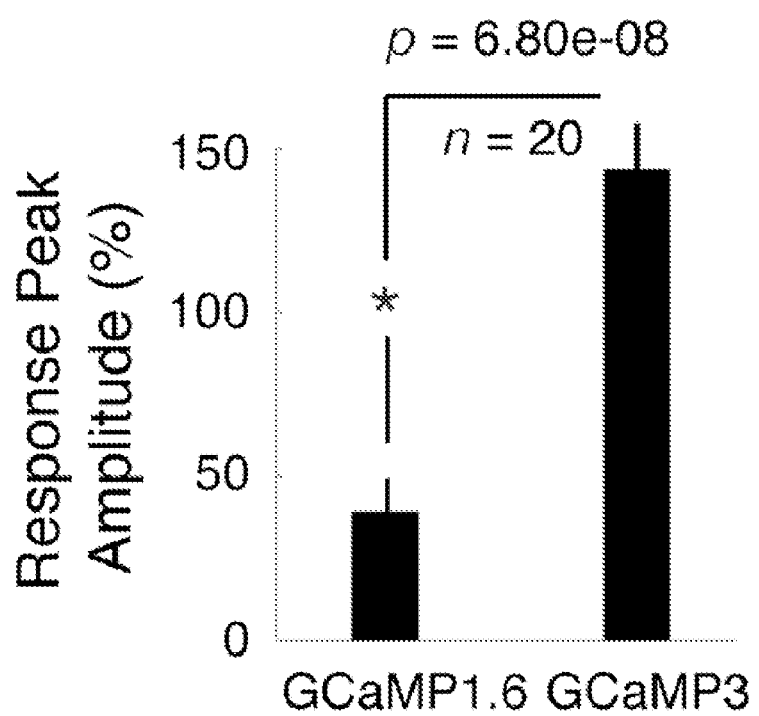

GCaMP1.6 and GCaMP3 were expressed in a broad subset of Drosophila olfactory projection neurons (PNs) in the antennal lobe (AL) and their responses to odour application were compared (GCaMP2 does not express well in Drosophila). Single copies of GCaMP were sufficient to produce visible fluorescence in glomeruli of the antennal lobe (AL), but two copies were used to allow imaging at low laser intensities. Neural activity was imaged in an identified glomerulus, DM2 (FIG. 5A) in response to the presentation of two odours, vinegar and isoamyl acetate. A ~4-fold increased fluorescence change in DM2 for GCaMP3 resulted as compared to GCaMP1.6, as measured by frame-scans (FIGS. 5B and 5C)

in response to vinegar (average ΔF/F of GCaMP3 is 143.7±16.7%; average ΔF/F of GCaMP1.6 is 39.3±10.9%). Similar results were obtained with glomerulus DM2 when the fly was stimulated with isoamyl acetate odour. These data show that GCaMP3 is a major improvement over existing GCaMPs for measuring sensory-evoked $Ca^{2+}$ transients in invertebrates.

Imaging Evoked and Spontaneous Ca2+ Transients in the Mouse Cortex In Vivo

Figure 6A:
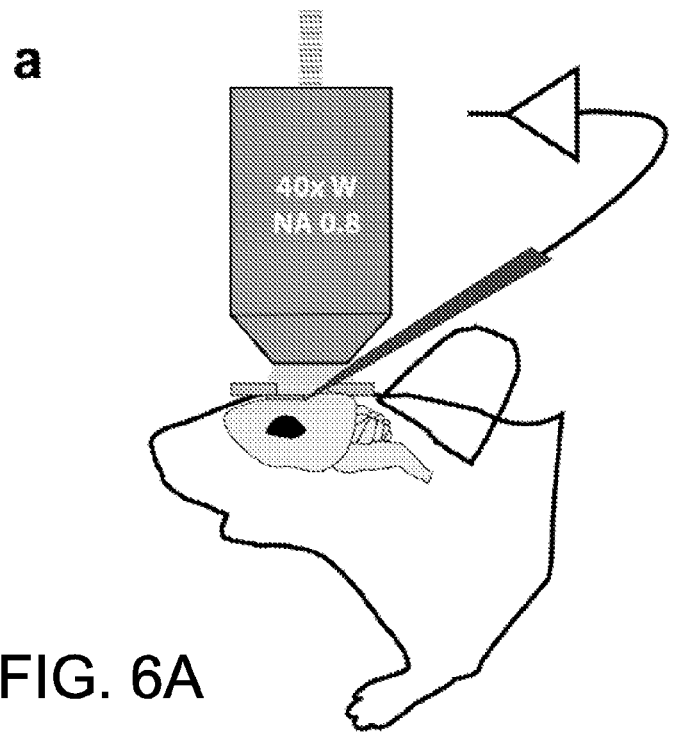
FIGS. 6A-6F show in vivo Ca2+ imaging of evoked and spontaneous activity with GCaMP3 in awake, behaving mice.

GCaMP3 was delivered to layer 2/3 somatosensory or motor cortical neurons via infection with adeno-associated virus (AAV2/1; synapsin-1 promoter). Twelve days after infection, robust expression was observed of GCaMP3 in layer 2/3 pyramidal neurons (FIG. 1E). Two-photon microscopy was used to image labeled cell bodies while simultaneously recording action potentials in whole-cell or cell-attached configurations (FIG. 6A).

Figure 6B:
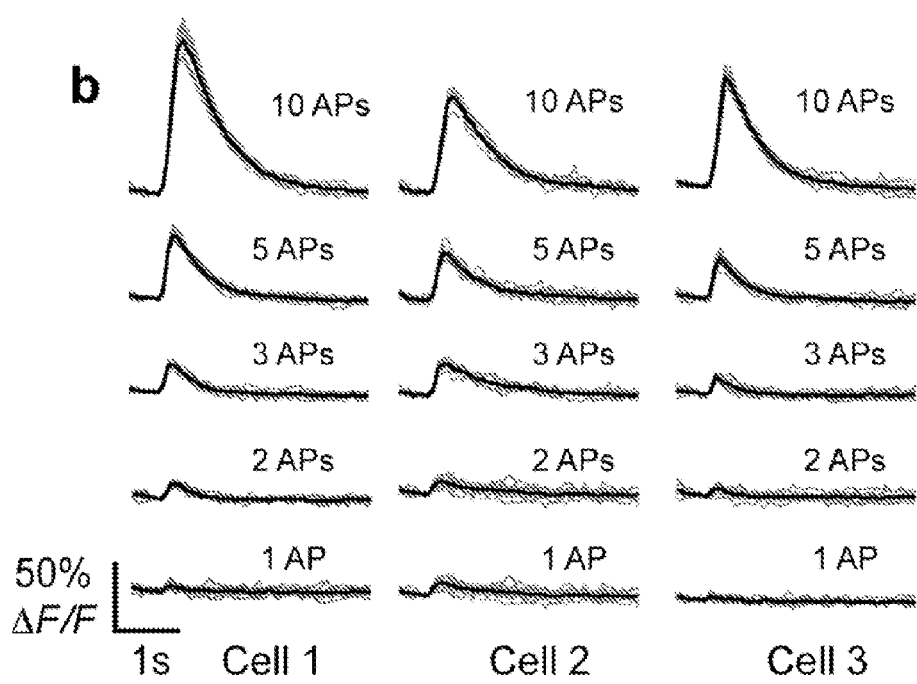
Figure 6C:
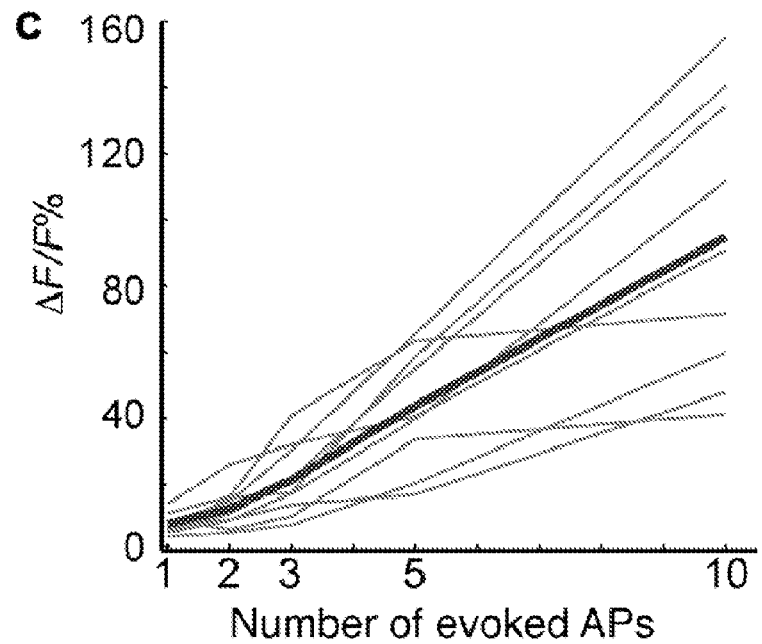

Fluorescence changes were tested using GCaMP3 and evoked action potentials that were triggered by brief current pulses in anesthetized mice. The average fluorescence response of GCaMP3 was nearly linearly related to the number of action potentials in trains of 1, 2, 3, 5 or 10 at 50 Hz (FIGS. 6B and 6C). A single AP caused a fluorescence increase of 7.9±2.8% (n=9 cells) (FIG. 6C). For bursts of 2, 3, 5 and 10 AP, the corresponding responses were 12.5±6.4%, 21.2±6.4%, 43.7±18.0% and 94.7±42.5%, respectively (n=9 cells) (FIG. 6C). The detection rate was 70% for single pulses, 90% for trains of 3 AP, and 100% for longer trains. Consistent with rapid calcium extrusion at physiological temperature (37° C.), GCaMP3 showed faster kinetics in vivo (decay $T_{1/2}$ at 10 pulses: 384±76 ms) compared to slice preparations (p=0.0015, paired t-test).

Fluorescence changes were imaged of GCaMP3 in response to sensory-evoked and spontaneous calcium transients in the primary motor cortex of awake mice running on a treadmill. Action potentials were recorded in a loose seal cell-attached configuration. The fluorescence change of GCaMP3 was linearly correlated with the number of action potentials from 3 APs up to 20 APs per 0.5 s (n=6 cells from 3 animals). Single and double action potentials were not reliably detected, likely due to movement noise and elevated baseline calcium levels in the awake brain.

Chronic Imaging with GCaMP3 in Mice

Long-term expression of GECIs in cortical neurons introduced via in utero electroporation caused altered physiology in some cells. It was found that ~8.3% of GCaMP3−, 13% of D3cpV− and 5% of TN-XXL-labeled L2/3 pyramidal neurons showed bright nuclear fluorescence at P25-P28. Neurons with filled nuclei had attenuated GCaMP fluorescence responses and reduced calcium changes evoked by neural activity. Anti-$His_6$ immuno-staining detected predominantly cytosolic GCaMP3, suggesting that the nuclei were filled with N-terminally cleaved GCaMP3. These results suggested that both calcium homeostasis and GECI function were impaired in neurons with labeled nuclei.

Figure 6D:
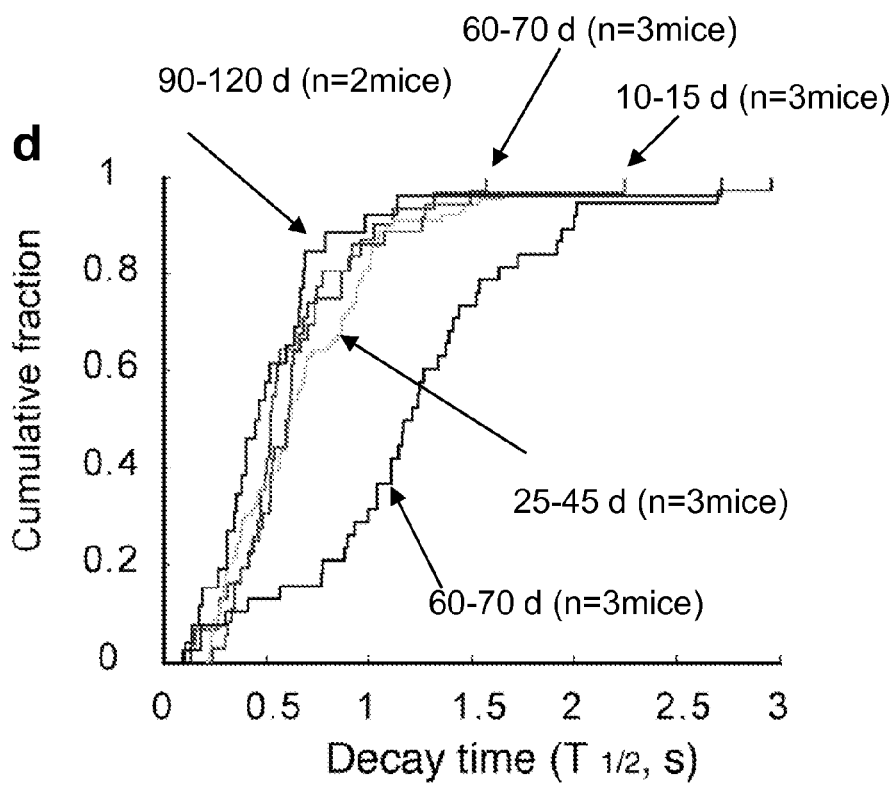

When GCaMP3 was introduced post-natally via viral transduction (under the control of the synapsin-1 promoter), some neurons near the injection site were bright and nuclear-filled. The spontaneous fluorescence transients of nuclear-filled neurons had long decay times, another signature of abnormal physiology (FIG. 6D). These perturbed cells were easily visually identified for exclusion. Basal fluorescence decreased with distance from the injection site and was nuclear-excluded over large areas of the brain, even after 120 days of expression (FIG. 6D). A variety of physiological methods were used to test for altered properties of nuclear-excluded, GCaMP3-positive neurons. Recoding was performed in brain slices from neurons expressing GCaMP3 for 2-3 weeks. GCaMP3-positive neurons had similar resting potential and excitability compared to GCaMP3-negative cells. Laser scanning photostimulation circuit mapping was used to test for changes in synaptic properties of GCaMP3-positive neurons. It was found that GCaMP3-positive and GCaMP3-negative neurons had indistinguishable total synaptic input. Thus, broad swathes of cortical surface expressed G-CaMP3 at levels suitable for quantitative optical physiology.

Figure 6E:
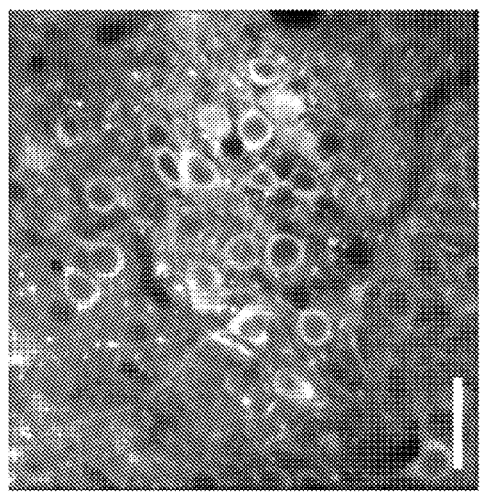
Figure 6E:
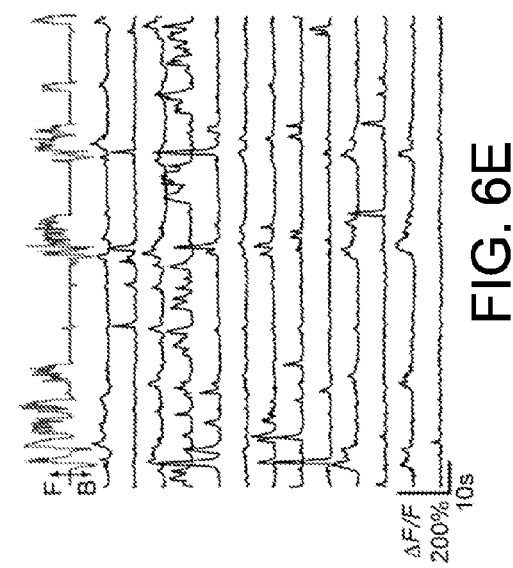
Figure 6F:
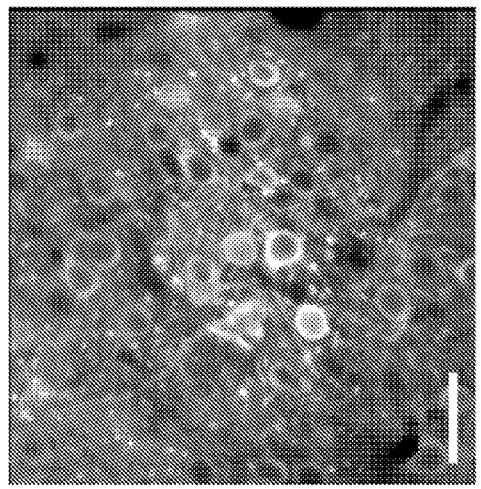
Figure 6F:
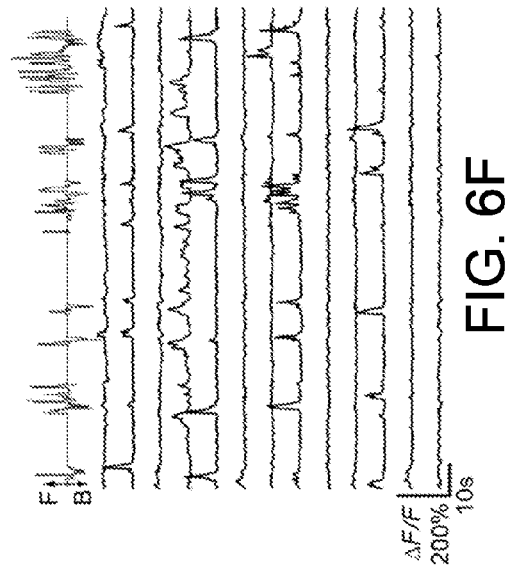

GCaMP3 was used to image the in vivo calcium activity of motor cortical neurons repeatedly through a cranial window (FIG. 6E). Numerous neurons displayed large-amplitude fluorescence transients during a 140 second imaging period while head-fixed mice ran on a treadmill (FIG. 6E). Population activity in the motor cortex was correlated with locomotor activity (FIG. 6E). The fluorescence decay rates of spontaneous calcium transients in imaged cells with nuclear exclusion were stable 120 days post-infection (FIG. 6D). Repeated imaging of the same neuronal population at 72 and 120 days post-infection showed remarkably constant GCaMP3 expression and signal change (FIG. 6F). These results demonstrate that GCaMP3 is suitable for long-term imaging of behaviorally correlated activity in large neuronal populations over extended periods of time.

Example 2

Use of GECIs to Screen for GPCR Agonists and Antagonists

Figure 7:
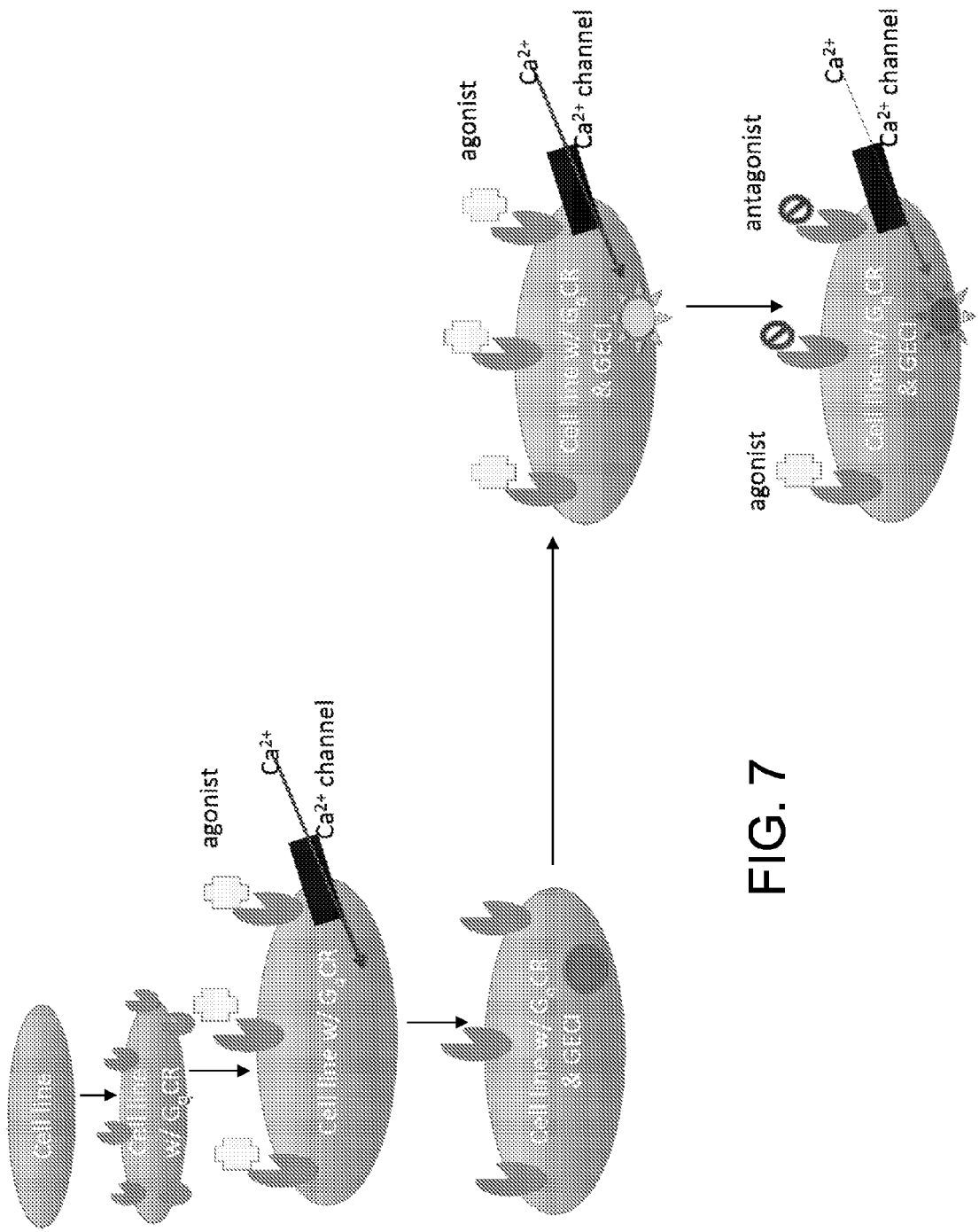
FIG. 7 is a schematic showing an example method of screening for modulators of GPCR. The top cartoon shows a cell line. The second cartoon (from the top) shows a cell line expressing a target protein either by genomic integration or transient transfection. The third cartoon shows a cell line expressing a target protein following the addition of a GPCR agonist, which results in Ca2+ ion uptake through Ca2+ channels. The fourth cartoon shows a cell line expressing a target protein and a GECI. The fifth cartoon shows the cell line expressing the target protein and GECI after the addition of a GPCR agonist resulting in Ca2+ ions entering the cell. The Ca2+ ions are detected by the GECI resulting in fluorescence increase. The last cartoon shows the cell line after addition of an antagonist, which competes the agonist off the target protein resulting in decreased GECI fluorescence.

As described in Example 1, GCaMP3, with superior fluorescence change, relative to all previous protein-encoded sensors, was developed. An example of using the GCaMP3 is shown in the schematic in FIG. 7.

The amino acid and nucleic acid sequences of GCaMP3 are provided as SEQ ID NO:2 and SEQ ID NO:1, respectively.

The nucleic acid sequence was cloned into a mammalian expression vector driving from the CAG promoter (pCAG). The vector was transfected into human HEK293 cells, which resulted in bright green fluorescence of the GCaMP3 sensor in the human cells.

Next a gene encoding mammalian codon-optimized histamine 1 receptor H1R was synthesized. The amino acid and nucleic acid sequences of the H1R are provided as SEQ ID NO:3 and SEQ ID NO:4, respectively.

Figure 8A:
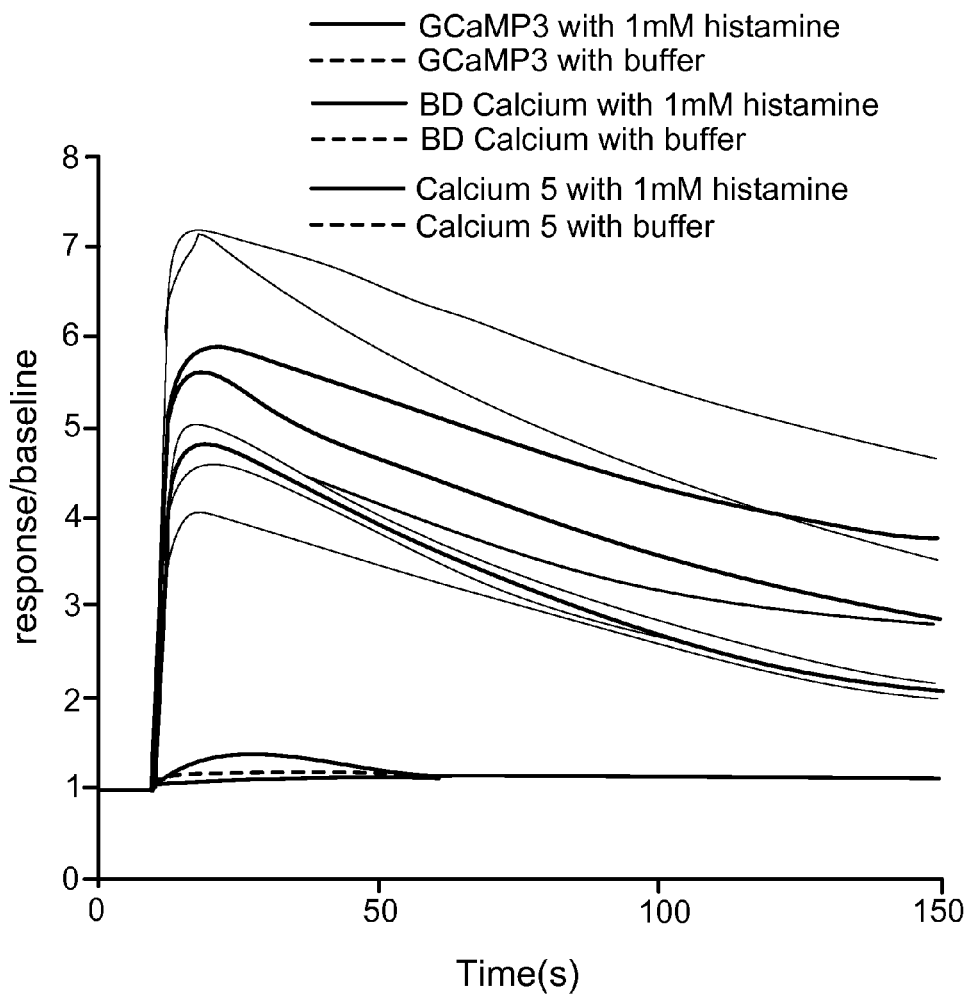
Figure 8B:
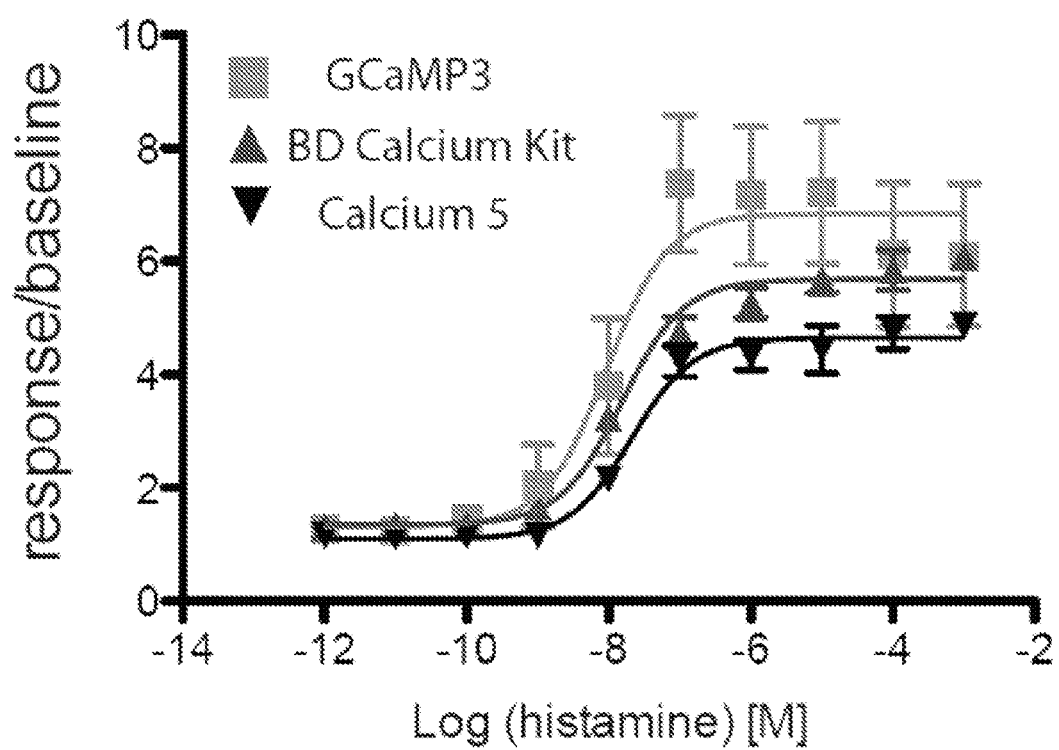
Figure 9A:
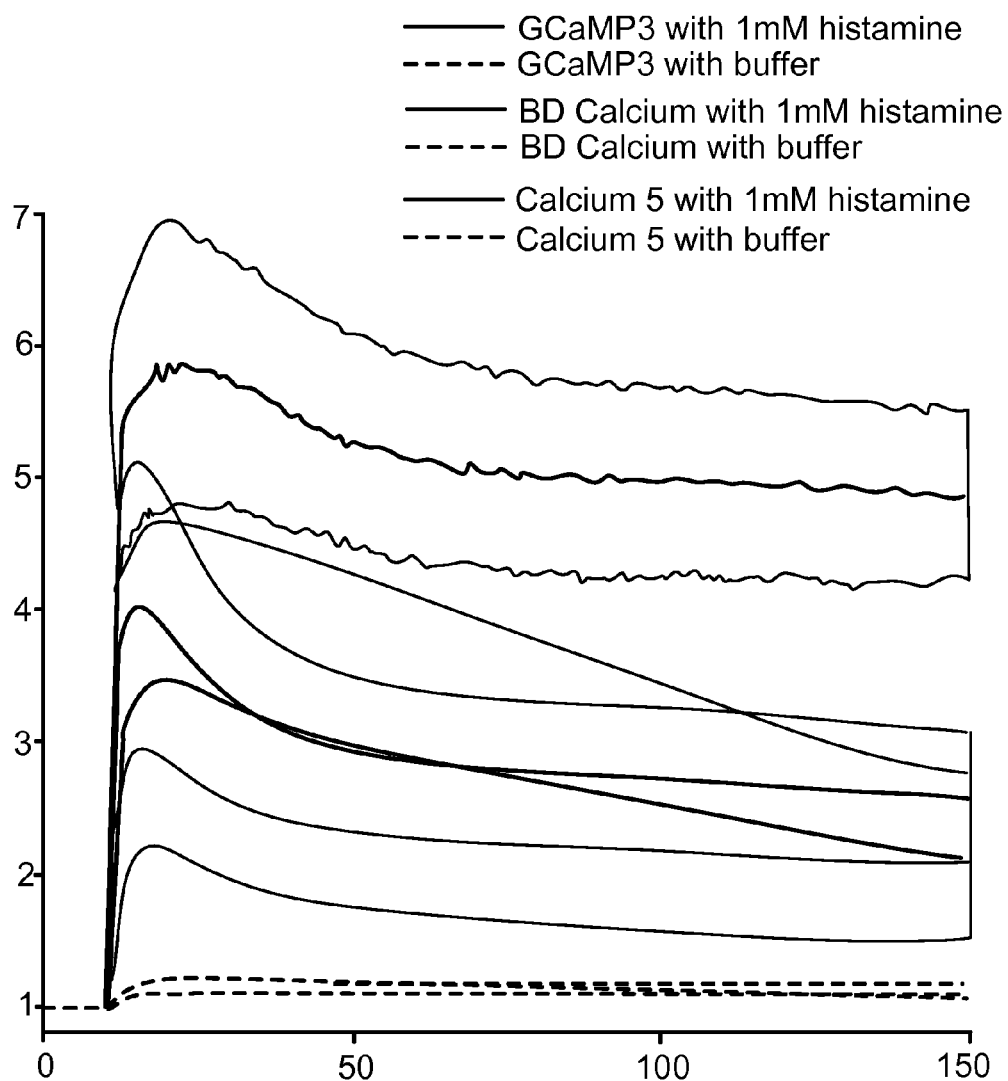
Figure 9B:
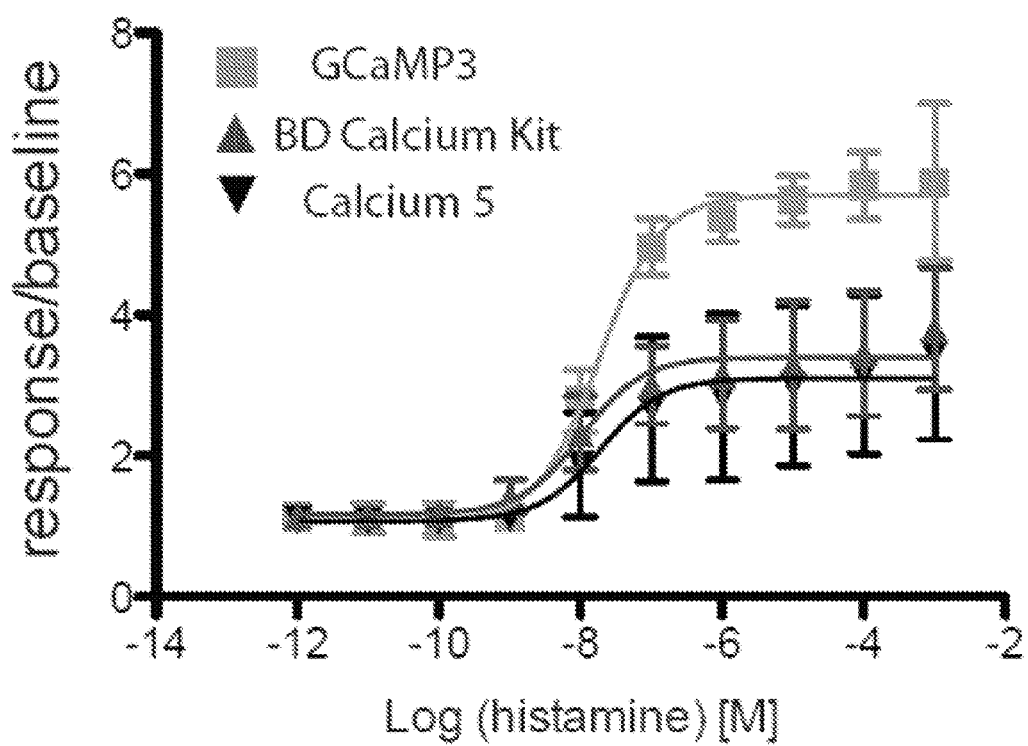
Figure 10A:
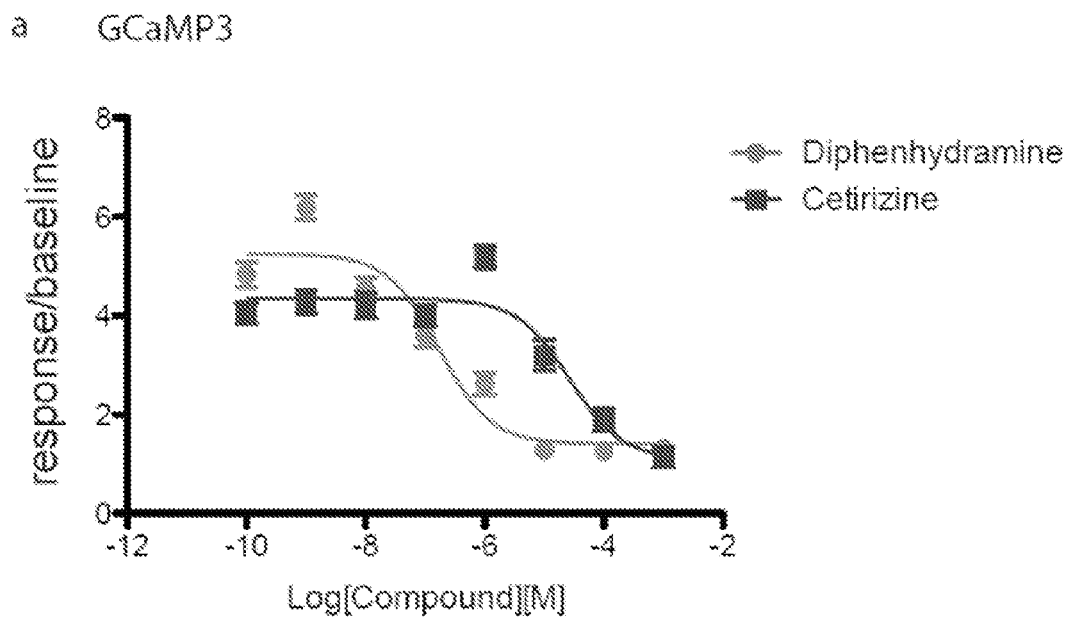
FIGS. 10A-10C show GCaMP3 outperformed the BD calcium-kit ("BD Calcium Kit") and the FLIPR calcium-5-kit ("Calcium 5") in HEK293 cells in the presence of histamine and two H1R antagonists.
Figure 10B:
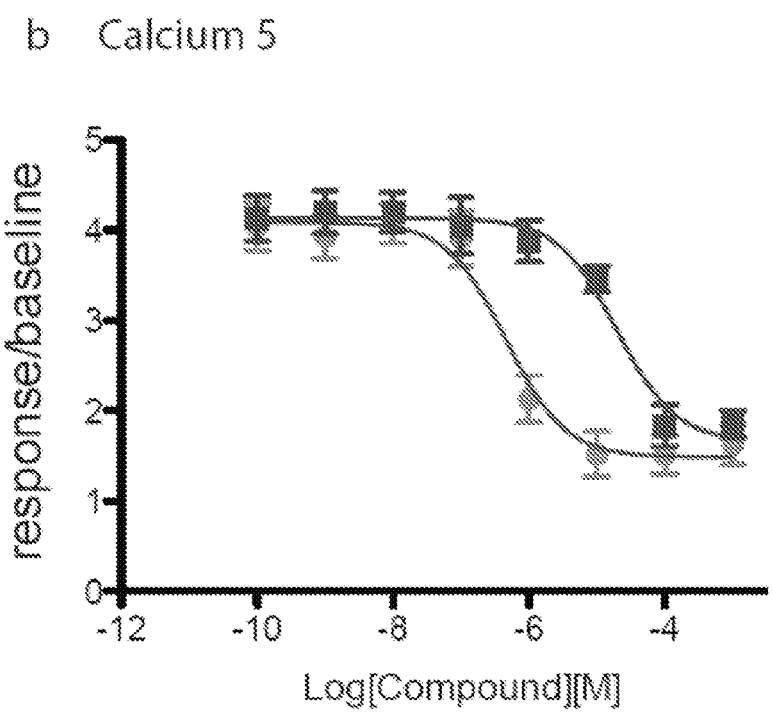
Figures 10C, 10D:
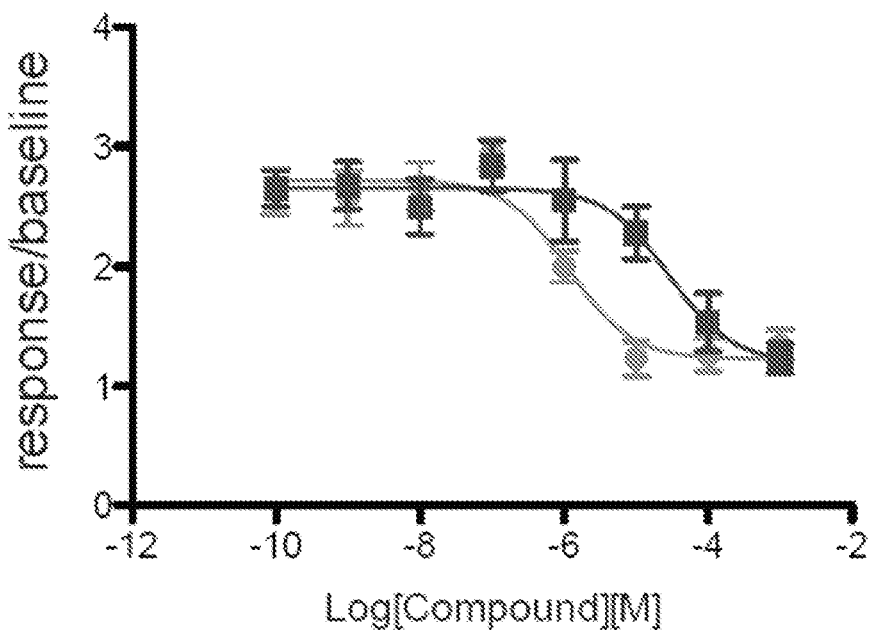
FIG. 10D is a table showing the EC50 values and Z' factor measured from the data of FIGS. 10A-10C.
Figure 11A:
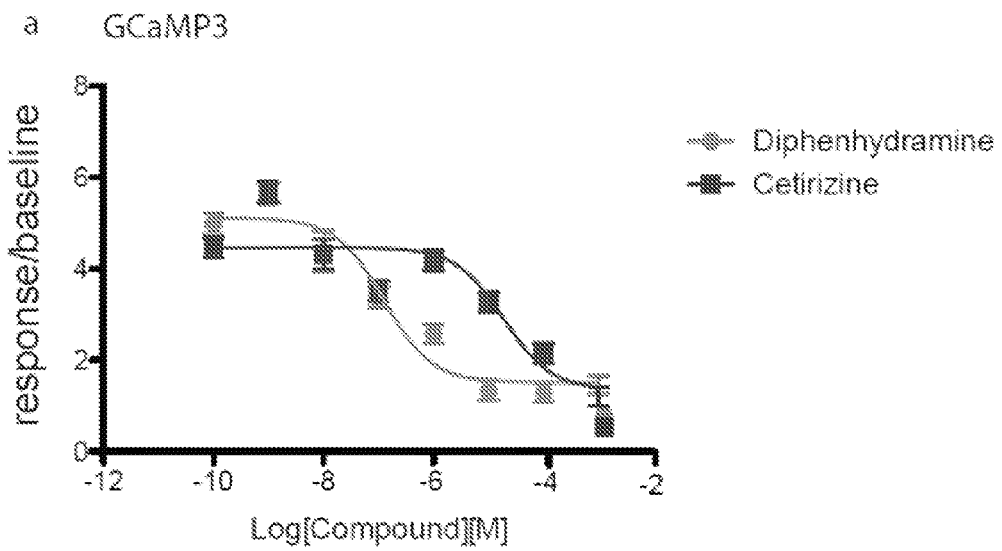
FIGS. 11A-11C show GCaMP3 outperformed the BD calcium-kit ("BD Calcium Kit") and the FLIPR calcium-5-kit ("Calcium 5") in HeLa cells in the presence of histamine and two H1R antagonists.
Figure 11B:
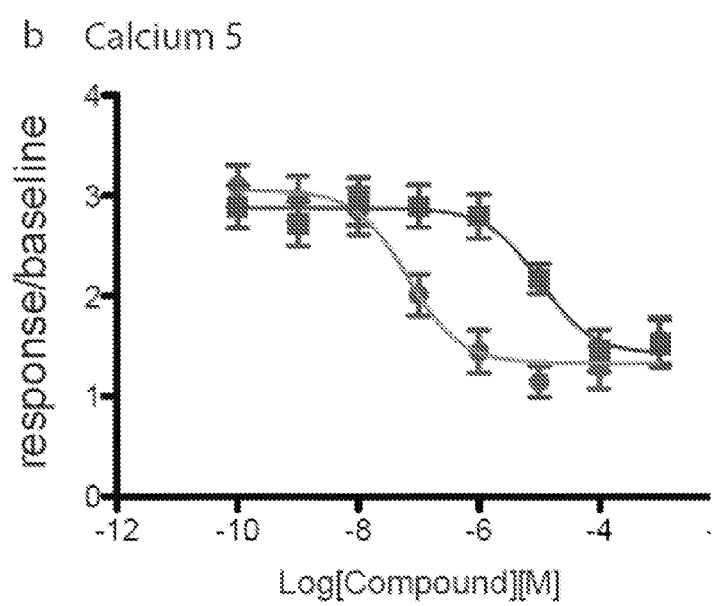
Figures 11C, 11D:
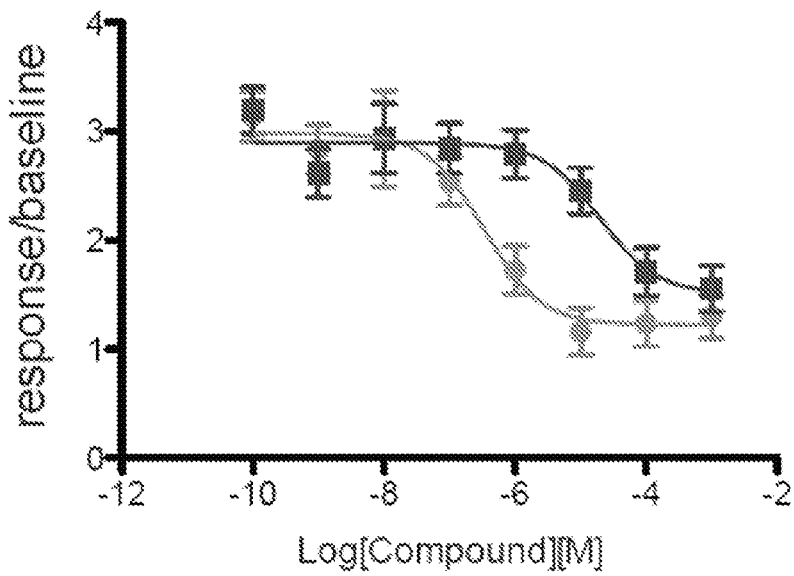
FIG. 11D is a table showing the EC50 values and Z' factor measured from the data of FIGS. 11A-11C.

The H1R was cloned into the pCAG mammalian expression vector. Co-transfection of both pCAG-GCaMP3 and pCAG-H1R into HEK293 cells gave bright green cells as before. In parallel, HEK293 cells were transfected with pCAG-H1R and incubated with either of the two best-performing small molecule dye calcium kits (the BD Calcium Kit from BD Biosciences and the FLIPR Calcium-5 Kit from Molecular Devices). Addition of histamine to the HEK293 cells prepared under the three conditions (transfected with GCaMP3, incubated with BD Calcium Kit, incubated with FLIPR Calcium-5 kit) each gave a titratable increase in fluorescence, with the GCaMP3 cells giving a greater response than the BD Calcium Kit-incubated cells, which gave a greater response than the FLIPR Calcium-5 kit-incubated cells (FIGS. 8A-8C). This experiment was then repeated with another common human cell line, HeLa cells, with similar results (FIGS. 9A-9C). For both cell types and all three assay conditions, the observed affinity of histamine for the H1R receptor are close to published values (reported as 24.0+/−1.7 nM in human COS-7 cells (Debacker et al., Biochem. Biophys. Res. Commun 197(3): 1601-1608 (1993)). In both cell types, GCaMP3 outperformed the two commercial small molecule dye kits in terms of fluorescence increase. All Z' factors were high, and response of the three Ca2+ indicators to buffer (with no histamine) was negligible.

These experiments were then repeated in both cell types, with both small molecule dye kits and GCaMP3-transfected cells, with the addition of both 10 nM histamine (~half-saturating) and different concentrations of the two H1R antagonists diphenhydramine and cetirizine. In all cases, the H1R antagonists compete off the effect of the histamine, with the response-to-baseline ratio dropping almost to 1.0, indicating near complete inhibition of the H1R receptor by the compounds (FIGS. 10A-10D and 11A-11D). The IC50 values determined by antagonist titration for the two cell types and two antagonists are similar between the three detection methods.

Together, these experiments and results demonstrate a protocol for studying the effect of small molecules, proteins, peptides, and other biomolecules on receptor activity in human cell lines. The method described herein is easily amenable to classes of target proteins whose activity results in an observable modulation of Ca2+ flux. The assay is simple, robust, cheap, and produces data of greater signal-to-noise quality than commercially available (expensive) kits. Cell lines that incorporate the GCaMP3 construct decrease assay-to-assay variability and make the assay protocol easy to run.

A number of embodiments have been described. Nevertheless, it will be understood that various modifications may be made. Accordingly, other embodiments are within the scope of the following claims.

What is claimed is:

1. An isolated nucleic acid sequence encoding a genetically encoded calcium indicator (GECI), wherein the GECI comprises SEQ ID NO: 2.

2. A vector comprising the isolated GECI-encoding nucleic acid sequence of claim 1.

3. An isolated cell comprising the isolated GECI-encoding nucleic acid sequence of claim 1.

4. The isolated cell of claim 3, wherein the GECI-encoding nucleic acid sequence is located in the genome of the cell.

5. An isolated polypeptide comprising a GECI, wherein the GECI comprises SEQ ID NO: 2.

6. An isolated cell comprising the isolated polypeptide of claim 5.

7. The isolated cell of claim 3, wherein the cell further comprises a G-protein coupled receptor (GPCR).

8. The isolated cell of claim 7, wherein the cell comprises a nucleic acid sequence encoding the GPCR.

9. The isolated cell of claim 8, wherein the nucleic acid sequence encoding the GPCR is located on a vector or in the genome of the cell.

10. The isolated cell of claim 7, wherein the GPCR is selected from the group consisting of alpha-1 adrenegic receptors (I1-AR), urotensin (UT) receptors, 5-HT2, 5-HT6 and 5-HT7 serotonin receptors, hypocretic (orexin) receptors, histamine H1 receptors, bradykinin receptors, bombesin receptors, purinergic receptors, acetycholine receptors, mGluR5 glutamate receptors, vasopressin receptors, angiotensin receptors, cholecystokinin receptors, endothelin receptors, ghrelin receptors, melatonin receptors, neurotensin receptors, platelet-activating factor receptors, prolactin releasing peptide receptors, GABA-B receptors, histamine receptors, and glutamate receptors.

11. The isolated cell of claim 3, wherein the cell is a Hela cell or a human embryonic kidney (HEK) cell.

12. The isolated cell of claim 11, wherein the HEK cell is a HEK293 cell.

13. The isolated cell of claim 6, wherein the cell further comprises a G-protein coupled receptor (GPCR).

14. The isolated cell of claim 13, wherein the cell comprises a nucleic acid sequence encoding the GPCR.

15. The isolated cell of claim 14, wherein the nucleic acid sequence encoding the GPCR is located on a vector or in the genome of the cell.

16. The isolated cell of claim 13, wherein the GPCR is selected from the group consisting of alpha-1 adrenegic receptors (I1-AR), urotensin (UT) receptors, 5-HT2, 5-HT6 and 5-HT7 serotonin receptors, hypocretic (orexin) receptors, histamine H1 receptors, bradykinin receptors, bombesin receptors, purinergic receptors, acetycholine receptors, mGluR5 glutamate receptors, vasopressin receptors, angiotensin receptors, cholecystokinin receptors, endothelin receptors, ghrelin receptors, melatonin receptors, neurotensin receptors, platelet-activating factor receptors, prolactin releasing peptide receptors, GABA-B receptors, histamine receptors, and glutamate receptors.

17. The isolated cell of claim 6, wherein the cell is a Hela cell or a human embryonic kidney (HEK) cell.

18. The isolated cell of claim 17, wherein the HEK cell is a HEK293 cell.

* * * * *